(12) United States Patent
Ajito et al.

(10) Patent No.: US 6,451,800 B1
(45) Date of Patent: Sep. 17, 2002

(54) PHENYLPIPERAZINE DERIVATIVES AS INTEGRIN $\alpha_V\beta_3$ ANTAGONISTS

(75) Inventors: Keiichi Ajito; Shoichi Murakami; Minoru Ishikawa; Mikio Yamamoto; Dai Kubota; Shuichi Gomi; Mitsugu Hachisu; Kiyoaki Katano, all of Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/601,176

(22) PCT Filed: Feb. 1, 1999

(86) PCT No.: PCT/JP99/00415

§ 371 (c)(1),
(2), (4) Date: Jul. 28, 2000

(87) PCT Pub. No.: WO99/38849

PCT Pub. Date: Aug. 5, 1999

(30) Foreign Application Priority Data

Jan. 30, 1998 (JP) ............................ 10-019282

(51) Int. Cl.$^7$ ................. A61K 31/497; A61K 31/4965; C07D 403/00; C07D 239/02; C07D 295/00
(52) U.S. Cl. ......................... 514/252.14; 514/254.06; 514/255.03; 544/295; 544/370; 544/393
(58) Field of Search ................. 544/295, 370, 544/393; 514/252.14, 254.06, 255.03

(56) References Cited

U.S. PATENT DOCUMENTS 4,532,240 A 7/1985 Werbel et al. ............... 514/252
5,356,559 A * 10/1994 Kelly et al. ............ 252/299.61

FOREIGN PATENT DOCUMENTS

JP 59-73573 4/1984

OTHER PUBLICATIONS

Engleman, V. W. "Cell Adhesion Integrins as Pharmaceutical Targets" in Annual Reports in Medicinal Chemistry, vol. 31, 1996, pp. 191–200.*
K. C. Nicolaou et al., Bioorganic & Medicinal Chemistry, vol. 6, pp. 1185–1208 (1998).
Srivatsa et al., Cardiovascular Research, 36, pp. 408–428 (1997).
Friedlander et al., Proc. Natl. Acad. Sci. USA, 93, pp. 9764–9769 (1996).
Carron et al., Cancer Research 58, pp. 1930–1935 (1998).
Storgard et al., The Journal of Clinical Investigation, 103(1), pp. 47–54 (1999).
Crippes et al., Endocrinology, 137(3), pp. 918–924 (1996).
Okada et al., American Journal of Pathology, 149(1), pp. 37–44 (1996).
Racanelli et al., Journal of Cardiac Society of U.S.A., Circulation, I–668, 3731, (1997).
Brooks, DN&P, 10(8), pp. 456–461 (1997).
Okada et al., Gendai Iryo, 29(11), pp. 2753–2758 (1997).
Kouns et al., Blood, 80(10), pp. 2539–2547 (1992).
Pytela et al., Methods in Enzymology, 144, pp. 475–489 (1987).
Liaw et al., Circulation Research, 74(2), pp. 214–224 (1994).
Engvall et al., J. Exp. Med., 147, pp. 1584–1595 (1978).
Gawaz et al.; Circulation, 96(6), pp. 1809–1818 (1997).
Brooks, DN&P, 10(8), pp. 456–461 (1997).
Choi et al., Journal of Vascular Surgery, 19(1), pp. 125–134 (1994).
Matsuno et al., Circulation, 90(5), pp. 2203–2206 (1994).
Racanelli et al., Abstracts from the 70$^{th}$ Scientific Sessions, Abstract No. 3734, p. I–668 (1997).
Mousa et al., Abstracts from the 70$^{th}$ Scientific Sessions, Abstract No. 623, p. I–111 (1997).
Byzova et al.; Thromb Haemost, 80, pp. 726–734 (1998).
Hammes et al., Nature Medicine, 2(5), pp. 529–533 (1996).
Okada et al., American Journal of Pathology, 149(1), pp. 37–44 (1996).
Kerr et al., Exp. Opin. Invest. Drugs, 9(6), pp. 1271–1279 (2000).
Storgard et al., The Journal of Clinical Investigation, 103(1), pp. 47–54 (1999).

* cited by examiner

Primary Examiner—Mukund J. Shah
Assistant Examiner—Tamthom N. Truong
(74) Attorney, Agent, or Firm—Wenderoth, Lind & Ponack, LLP

(57) ABSTRACT

An objective of the present invention is to provide compounds having integrin $\alpha_V\beta_3$ antagonistic activity, GP IIb/IIIa antagonistic activity, and/or human platelet aggregation inhibitory activity, and therapeutic agents for treating integrin $\alpha_V\beta_3$-mediated diseases and for inhibiting platelet aggregation. The derivatives according to the present invention are compounds represented by formula (I) or pharmaceutically acceptable salts or solvates thereof:

(I)

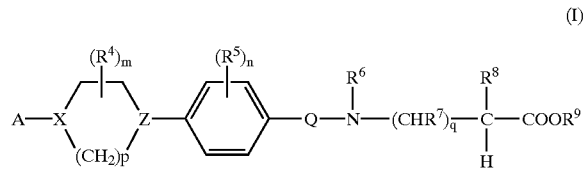

wherein A represents a five- to seven-membered heterocyclic ring containing two nitrogen atoms or the like; X and Z represent CH or a nitrogen atom; $R^4$ and $R^5$ represent alkyl, halogen or the like; Q represents >C=O, >CH$_2$ or the like; $R^6$ represents H, alkyl, aralkyl or the like; $R^7$ represents H, alkynyl or the like; $R^8$ represents H, substituted amino or the like; $R^9$ represents H or alkyl; m is 0 to 5; n is 0 to 4; p is 2 or 3; and q is 0 or 1.

24 Claims, No Drawings

PHENYLPIPERAZINE DERIVATIVES AS INTEGRIN $\alpha_v\beta_3$ ANTAGONISTS

BACKGROUND OF THE INVENTION

1. Field of the Invention

The present invention relates to phenylpiperazine derivatives and phenylpiperidine derivatives having integrin $\alpha_v\beta_3$ antagonistic activity, and pharmaceuticals comprising the same.

2. Background Art

In recent years, cell adherent proteins have been enthusiastically studied to apply proteins or the like involved in the mechanism of the regulation of cell adhesion to pharmaceuticals. Regarding interaction between platelet membrane glycoprotein GP IIb/IIIa and fibrinogen which plays an important role in platelet aggregation, extensive studies have already been carried out in various countries of the world, with consideration of clinical tests. For example, ReoPro having platelet aggregation activity has been clinically used.

Integrin $\alpha_v\beta_3$ which interacts with various extracellular matrix or cell adhesive proteins, has been proved to play an important role in the progress of arterial sclerosis, arterialization, and solid tumors. For this reason, regarding integrin $\alpha_v\beta_3$ antagonist as well, animal experiments have been initiated with consideration of clinical tests in various countries. Attention has been drawn to this by chemical and biochemical researchers, as well as by medical care-related persons engaged in basic research (Journal of Cardiac Society of U.S.A., Circulation, I-668, 1997, DuPont-Merck).

Up to now, small molecules having integrin $\alpha_v\beta_3$ antagonistic activity have been reported (WO 95/32710 (Merck), WO 96/37492 (DuPont-Merck), WO 97/01540 (SKB), WO 97/08145 (Searle & Co.), WO 97/23451 (Merck), WO 7/23480 DuPont-Merck), WO 97/24119(SKB), WO 97/33887 (DuPont-Merck), WO 97/36858 (Searle & Co.), WO 97/36859 (Searle & Co.), WO 97/36860 (Searle & Co.), WO 97/36861 (Searle & Co.), WO 97/36862 (Searle & Co.), and EP 0796855 (Hoechst).

SUMMARY OF THE INVENTION

The present inventors have found that a certain group of derivatives have potent integrin $\alpha_v\beta_3$ antagonistic activity. The present inventors have also found that a certain group of derivatives have potent GP IIb/IIIa antagonistic activity and human platelet aggregation inhibitory activity.

Accordingly, an object of the present invention is to provide a compound having integrin $\alpha_v\beta_3$ antagonistic activity, GP IIb/IIIa antagonistic activity, and/or human platelet aggregation inhibitory activity.

Another object of the present invention is to provide a therapeutic agent for integrin $\alpha_v\beta_3$-mediated diseases and an agent for inhibiting a platelet aggregation.

According to one aspect of the present invention, there is provided a compound represented by formula (I) or a pharmaceutically acceptable salt or solvate thereof:

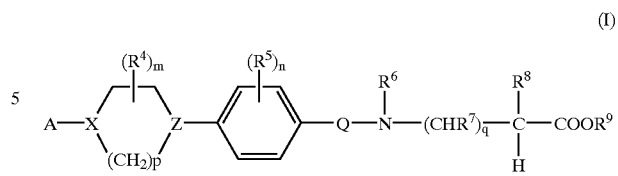

(I)

wherein

A represents a saturated or unsaturated five- to seven-membered heterocyclic group containing two nitrogen atoms, which is optionally substituted by $C_{1-6}$ alkyl or amino optionally substituted by $C_{1-6}$ alkyl, aralkyl, $C_{1-6}$ alkoxycarbonyl, or aralkyloxycarbonyl, or which is optionally condensed with other saturated or unsaturated five- to seven-membered carbocyclic ring or heterocyclic ring to form a bicyclic group, wherein the carbocyclic group and the heterocyclic group are optionally substituted by $C_{1-6}$ alkyl or amino optionally substituted by $C_{1-6}$ alkyl, aralkyl, $C_{1-6}$ alkoxycarbonyl, or aralkyloxycarbonyl, or a group represented by formula

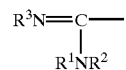

wherein $R^1$, $R^2$, and $R^3$, which may be the same or different, represent a hydrogen atom, $C_{1-6}$ alkyl, $C_{2-6}$ alkenyl, $C_{2-6}$ alkynyl, aralkyl, or nitrile, or $R^1$ and $R^2$ may together form group —$(CH_2)_r$—, wherein r is 4 or 5, or group —$(CH_2)_2$—O—$(CH_2)_2$—, wherein $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl;

X and Z, which may be the same or different, represent CH or N;

$R^4$ represents $C_{1-6}$ alkyl, $C_{1-6}$ alkoxy, a halogen atom, amino, nitro, hydroxyl, or an oxygen atom, wherein $C_{1-6}$ alkyl and $C_{1-6}$ alkoxy are optionally substituted by a halogen atom, $C_{1-6}$ alkoxy, amino, or hydroxyl;

$R^5$ represents $C_{1-6}$ alkyl, $C_{1-6}$ alkoxy, a halogen atom, amino, nitro, or hydroxyl, wherein $C_{1-6}$ alkyl and $C_{1-6}$ alkoxy are optionally substituted by a halogen atom, $C_{1-6}$ alkoxy, amino, or hydroxyl;

Q represents >C=O, >$CH_2$, >$CHR^{10}$, or >$CHOR^{10}$ wherein $R^{10}$ represents $C_{1-6}$ alkyl;

$R^6$ represents a hydrogen atom, $C_{1-6}$ alkyl, $C_{2-6}$ alkenyl, $C_{2-6}$ alkynyl, or aralkyl, wherein $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl;

$R^7$ represents a hydrogen atom, $C_{1-6}$ alkyl, $C_{2-6}$ alkenyl, $C_{2-6}$ alkynyl, aralkyl, or amino, wherein $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl, and amino is optionally substituted by $C_{1-6}$ alkyl, $C_{1-6}$ alkoxycarbonyl, benzenesulfonyl in which the phenyl portion is optionally substituted by $C_{1-6}$ alkyl, or aralkyloxycarbonyl;

$R^8$ represents a hydrogen atom, $C_{1-6}$ alkyl, $C_{2-6}$ alkenyl, $C_{2-6}$ alkynyl, aralkyl, or amino, wherein $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl, and the amino is optionally substituted by $C_{1-6}$ alkyl, $C_{1-6}$ alkoxycarbonyl, alkylsulfonyl, benzenesulfonyl in which the phenyl portion is optionally substituted by $C_{1-6}$ alkyl, phenyl optionally condensed with the phenyl portion, carboxyl, hydroxyl, nitro, amino, saturated or unsaturated five- to seven-membered carbocyclic group or heterocyclic group, $C_{1-6}$ alkylamino or a halogen atom, aralkyloxycarbonyl, or group —C(=O)—(CH$_2$)$_s$—C(=O)—NHR$^{11}$ wherein s is an integer of 0 to 4 and R$^{11}$ represents a hydrogen atom or hydroxyl;

R$^9$ represents a hydrogen atom or $C_{1-6}$ alkyl;

m is an integer of 0 to 5;

n is an integer of 0 to 4;

p is 2 or 3; and q is 0 or 1.

The compounds according to the present invention are useful in the treatment of integrin $\alpha_v\beta_3$-mediated diseases. The compounds according to the present invention are also useful as an agent for inhibiting platelet aggregation.

DETAILED DESCRIPTION OF THE INVENTION

Compound

As used herein, the term "$C_{1-6}$ alkyl" and "$C_{1-6}$ alkoxy" as a group or a part of a group respectively mean straight chain, branched chain, or cyclic alkyl and alkoxy having 1 to 6, preferably 1 to 4 carbon atoms.

As used herein, the term "$C_{2-6}$ alkenyl" and "$C_{2-6}$ alkynyl" as a group or a part of a group respectively mean straight chain, branched chain, or cyclic alkenyl or alkynyl having 2 to 6, preferably 2 to 4 carbon atoms.

Examples of $C_{1-6}$ alkyl include methyl, ethyl, n-propyl, isopropyl, cyclopropyl, cyclopropylmethyl, n-butyl, i-butyl, s-butyl, t-butyl, n-pentyl, cyclopentyl, n-hexyl, and cyclohexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$-alkenyl include allyl.

Examples of $C_{2-6}$ alkynyl include 2-propynyl and ethinyl.

Examples of saturated or unsaturated five- to seven-membered carbocyclic groups include phenyl.

As used herein, the term "saturated or unsaturated five- to seven-membered heterocyclic ring" means a five- to seven-membered heterocyclic ring containing at least one heteroatom selected from oxygen, nitrogen, and sulfur atoms, preferably a five- to seven-membered heterocyclic ring containing one nitrogen atom, more preferably a five- or six-membered heterocyclic ring containing one nitrogen atom. The term "hetero-atom" used herein means an oxygen, nitrogen, or sulfur atom. Examples of saturated or unsaturated five- to seven-membered heterocyclic groups include pyrimidyl, 1,4,5,6-tetrahydropyrimidyl, imidazolyl, tetrahydro-[1,3]diazepinyl, and imidazolidinyl.

The saturated or unsaturated heterocyclic group may be condensed with another saturated or unsaturated heterocyclic ring to form a bicyclic ring. Such condensed cyclic groups include benzimidazolyl, naphthyl, and azabenzimidazolyl.

As used herein, the term "aralkyl" as a group or a part of a group means a $C_{1-6}$ alkyl, preferably $C_{1-4}$ alkyl, substituted by a saturated or unsaturated five- to seven-membered carbocyclic group or heterocyclic group. Examples of aralkyls include benzyl and phenethyl.

The term "halogen atom" means a fluorine, chlorine, bromine, or iodine atom.

Both X and Z preferably represent nitrogen.

The five- to seven-membered heterocyclic group represented by A is preferably a five- or six-membered heterocyclic group.

The bicyclic heterocyclic group represented by A is preferably a nine- or ten-membered heterocyclic group, more preferably a nine- or ten-membered heterocyclic group containing two or three nitrogen atoms.

Preferably, A is a group represented by formula $$\text{Het}\begin{array}{c}N\\ \diagdown\\ C—\\ \diagup\\ N\end{array}$$

wherein

Het represents a saturated or unsaturated five- to seven-membered heterocyclic group containing two nitrogen atoms, which is optionally substituted by $C_{1-6}$ alkyl or amino optionally substituted by $C_{1-6}$ alkyl, aralkyl, $C_{1-6}$ alkoxycarbonyl, or aralkyloxycarbonyl, or which is optionally condensed with another saturated or unsaturated five- to seven-membered carbocyclic ring or heterocyclic ring, preferably another saturated or unsaturated five- to seven-membered carbocyclic ring or heterocyclic ring containing one nitrogen atom, to form a bicyclic group, wherein the carbocyclic group and the heterocyclic group are optionally substituted by $C_{1-6}$ alkyl or amino optionally substituted by $C_{1-6}$ alkyl, aralkyl, $C_{1-6}$ alkoxycarbonyl or aralkyloxycarbonyl.

$$R^{23}N=C—\\ |\\ R^{21}NR^{22}$$

wherein $R^{21}$, $R^{22}$, and $R^{23}$, which may be the same or different, represent a hydrogen atom, $C_{1-6}$ alkyl, $C_{2-6}$ alkenyl, or aralkyl, wherein $C_{1-6}$ alkyl, $C_{2-6}$ alkenyl, and aralkyl are optionally substituted by a halogen atom, $C_{1-6}$ alkoxy, amino, or hydroxyl, or $R^{21}$ and $R^{23}$ may together form group —(CH$_2$)$_4$—, group —(CH$_2$)$_3$—, group —CHR$^{24}$CH$_2$CH$_2$— wherein R$^{24}$ represents $C_{1-6}$ alkyl or amino optionally substituted by $C_{1-6}$ alkyl, $C_{1-6}$ alkoxycarbonyl, aralkyl, or aralkyloxycarbonyl, group —CH$_2$CHR$_{24}$CH$_2$— wherein R$^{24}$ is as defined above, group —CH$_2$CH$_2$—, group —CHR$^{24}$CH$_2$— wherein R$^{24}$ is as defined above, group —CR$^{25}$=CR$^{26}$— wherein R$^{25}$ and R$^{26}$, which may be the same or different, represent a hydrogen atom or $C_{1-6}$ alkyl, or R$^{25}$ and R$^{26}$ may together form —CH=CH—CH=CH—, —N=CH—CH=CH—, or —CH=N—CH=CH—, or $R^{21}$ and $R^{23}$ may together form group =CH—CH=CH—, group =CH—CH=N—, or group =CH—N=CH—, and $R^{22}$ may represent a single bond between $R^{21}$ and the nitrogen atom attached to $R^{21}$.

In the compound represented by formula (I), one or more hydrogen atoms in the following portion may be substituted by $R^4$.

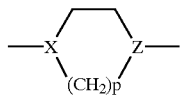

When m is zero (0), $R^4$ is absent. When m is 1, one hydrogen atom in the above portion is substituted by $R^4$. When m is 2 or more, two or more hydrogen atoms in the above portion are substituted by $R^4$. In this case, the substituents may be the same or different. When $R^4$ represents an oxygen atom, the bond between the $R^4$ and the above portion is a double bond. m is preferably an integer of 0 to 2.

In the compound represented by formula (I), one or more hydrogen atoms in the phenylene portion may be substituted by $R^5$.

When n is zero (0), $R^5$ is absent. When n is 1, one hydrogen atom in the phenylene portion is substituted by $R^5$. When n is 2 or more, two or more hydrogen atoms in the phenylene portion are substituted by $R^5$. In this case, the substituents may be the same or different. n is preferably an integer of 0 to 2.

Q preferably represents >C=O or >CH$_2$.

$R^6$ preferably represents a hydrogen atom, $C_{1-6}$ alkyl, preferably methyl, propyl, or cyclopropylmethyl, or aralkyl, preferably benzyl or phenethyl.

$R^7$ preferably represents a hydrogen atom, $C_{2-6}$ alkynyl, or optionally substituted amino, more preferably a hydrogen atom or $C_{2-6}$ alkynyl.

When q is zero (0), —(CHR$^7$)$_q$— represents a single bond. q is preferably 1.

$R^8$ preferably represents a hydrogen atom, $C_{2-6}$ alkynyl, or optionally substituted amino, more preferably a hydrogen atom or optionally substituted amino.

The phenyl portion of benzenesulfonyl as a substituent of amino represented by $R^7$ and $R^8$ may be substituted by 1 to 3 $C_{1-6}$alkyl which may be the same or different.

The aralkyl portion of aralkyloxycarbonyl as a substituent of amino represented by $R^7$ and $R^8$ may be benzyl or phenethyl.

s in group —C(=O)—(CH$_2$)$_s$—C(=O)—NHR$^{11}$ as a substituent of amino represented by $R^7$ and $R^8$ is preferably an integer of 1 to 3, more preferably 1 or 2.

A group of preferred compounds represented by formula (I) are those wherein

X and Z both represent N;

A represents a group of formula

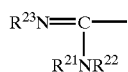

wherein $R^{21}$, $R^{22}$, and $R^{23}$ are as defined above;

Q represents >C=O or >CH$_2$;

$R^6$ represents a hydrogen atom, $C_{1-6}$ alkyl, or aralkyl, wherein $C_{1-6}$ alkyl and aralkyl are optionally substituted by a halogen atom, $C_{1-6}$ alkoxy, amino, or hydroxyl;

$R^7$ represents a hydrogen atom or $C_{2-6}$ alkynyl;

$R^8$ represents a hydrogen atom or amino optionally substituted by $C_{1-6}$ alkyl; $C_{1-6}$ alkoxycarbonyl; benzenesulfonyl in which the phenyl portion is optionally substituted by $C_{1-6}$ alkyl; aralkyl; aralkyloxycarbonyl; or group —C(=O)—(CH$_2$)$_s$—C(=O)—NHR$^{11}$ wherein s is an integer of 0 to 4 and $R^{11}$ represents a hydrogen atom or hydroxyl;

m and n are each an integer of 0 to 2; and q is 1.

Of the compounds represented by formula (I), the following compounds are particularly preferred:

(1) t-butyl (2S)-benzenesulfonylamino-3-[4-{4-(pyrimidin-2-yl)-piperazin-1-yl}-benzoylamino]-propionate;

(2) (2S)-benzenesulfonylamino-3-[4-{4-(pyrimidin-2-yl)-piperazin-1-yl}-benzoylamino]-propionic acid;

(3) (2S)-benzenesulfonylamino-3-[4-{4-(1,4,5,6-tetrahydropyrimidin-2-yl)-piperazin-1-yl}-benzoylamino]-propionic acid;

(4) t-butyl (2S)-benzenesulfonylamino-3-[4-{4-(pyrimidin-2-yl)-[1,4]diazepan-1-yl}-benzoylamino]-propionate;

(5) (2S)-benzenesulfonylamino-3-[4-{4-(pyrimidin-2-yl)-[1,4]diazepan-1-yl}-benzoylamino]-propionic acid;

(6) (2S)-benzenesulfonylamino-3-[4-{4-(1,4,5,6-tetrahydropyrimidin-2-yl)-[1,4]diazepan-1-yl}-benzoylamino]-propionic acid;

(7) t-butyl (2S)-benzenesulfonylamino-3-[4-{3-methyl-4-(pyrimidin-2-yl)-piperazin-1-yl}-benzoylamino]-propionate;

(8) (2S)-benzenesulfonylamino-3-[4-{3-methyl-4-(pyrimidin-2-yl)-piperazin-1-yl}-benzoylamino]-propionic acid;

(9) (2S)-benzenesulfonylamino-3-[4-{3-methyl-4-(1,4,5,6-tetrahydropyrimidin-2-yl)-piperazin-1-yl}-benzoylamino]-propionic acid;

(10) t-butyl (2S)-benzenesulfonylamino-3-[4-{(3R)-methyl-4-(pyrimidin-2-yl)-piperazin-1-yl}-benzoylamino]-propionate;

(11) (2S)-benzenesulfonylamino-3-[4-{(3R)-methyl-4-(pyrimidin-2-yl)-piperazin-1-yl}-benzoylamino]-propionic acid;

(12) (2S)-benzenesulfonylamino-3-[4-{(3R)-methyl-4-(1,4,5,6-tetrahydropyrimidin-2-yl)-piperazin-1-yl}-benzoylamino]-propionic acid;

(13) t-butyl (2S)-benzenesulfonylamino-3-[4-{(3S)-methyl-4-(pyrimidin-2-yl)-piperazin-1-yl}-benzoylamino]-propionate;

(14) (2S)-benzenesulfonylamino-3-[4-{(3S)-methyl-4-(pyrimidin-2-yl)-piperazin-1-yl}-benzoylamino]-propionic acid;

(15) (2S)-benzenesulfonylamino-3-[4-{(3S)-methyl-4-(1,4,5,6-tetrahydropyrimidin-2-yl)-piperazin-1-yl}-benzoylamino]-propionic acid;

(16) t-butyl (2S)-benzenesulfonylamino-3-[4-{4-(1H-benzimidazol-2-yl)-piperazin-1-yl}-benzoylamino]-propionate;

(17) (2S)-benzenesulfonylamino-3-[4-{4-(1H-benzimidazol-2-yl)-piperazin-1-yl}-benzoylamino]-propionic acid;

(18) ethyl (3S)-[4-{4-(pyrimidin-2-yl)-piperazin-1-yl}-benzoylamino]-pent-4-ynate;

(19) (3S)-[4-{4-(pyrimidin-2-yl)-piperazin-1-yl}-benzoylamino]-pent-4-ynic acid;

(20) t-butyl (2S)-benzenesulfonylamino-3-[4-{4-(pyrimidin-2-yl)-piperazin-1-yl}-benzylamino]-propionate;

(21) (2S)-benzenesulfonylamino-3-[4-{4-(pyrimidin-2-yl)-piperazin-1-yl}-benzylamino]-propionic acid;

(22) (2S)-benzenesulfonylamino-3-{4-[4-(1,4,5,6-tetrahydropyrimidin-2-yl)-piperazin-1-yl]-benzylamino}-propionic acid;

(23) (2S)-benzenesulfonylamino-3-[methyl-[4-{4-(pyrimidin-2-yl)-piperazin-1-yl}-benzyl]-amino]-propionic acid;

(24) (2S)-benzenesulfonylamino-3-[methyl-[4-{4-(1,4,5,6-tetrahydropyrimidin-2-yl)-piperazin-1-yl}-benzyl]-amino]-propionic acid;

(25) (2S)-benzenesulfonylamino-3-[benzyl-[4-{4-(pyrimidin-2-yl)-piperazin-1-yl}-benzyl]-amino]-propionic acid;

(26) (2S)-benzenesulfonylamino-3-[benzyl-[4-{4-(1,4,5,6-tetrahydropyrimidin-2-yl)-piperazin-1-yl}-benzyl]-amino]-propionic acid;

(27) t-butyl (2S)-benzyloxycarbonylamino-3-[4-{4-(pyrimidin-2-yl)-piperazin-1-yl}-benzoylamino]-propionate;

(28) (2S)-benzyloxycarbonylamino-3-[4-{4-(pyrimidin-2-yl)-piperazin-1-yl}-benzoylamino]-propionic acid;

(29) (2S)-amino-3-[4-{4-(1,4,5,6-tetrahydropyrimidin-2-yl)-piperazin-1-yl}-benzoylamino]-propionic acid;

(30) (2S)-benzyloxycarbonylamino-3-[4-{4-(1,4,5,6-tetrahydropyrimidin-2-yl)-piperazin-1-yl}-benzoylamino]-propionic acid;

(31) t-butyl (2S)-benzenesulfonylamino-3-[cyclopropylmethyl-[4-{4-(pyrimidin-2-yl)-piperazin-1-yl}-benzoyl]-amino]-propionate;

(32) (2S)-benzenesulfonylamino-3-[cyclopropylmethyl-[4-{4-(pyrimidin-2-yl)-piperazin-1-yl}-benzoyl]-amino]-propionic acid;

(33) (2S)-benzenesulfonylamino-3-[cyclopropylmethyl-[4-{4-(1,4,5,6-tetrahydropyrimidin-2-yl)-piperazin-1-yl}-benzoyl]-amino]-propionic acid;

(34) (2S)-benzenesulfonylamino-3-[4-{4-(amidino)-piperazin-1-yl}-benzoylamino]-propionic acid;

(35) t-butyl (2S)-benzenesulfonylamino-3-[4-{cis-3,5-dimethyl-4-(pyrimidin-2-yl)-piperazin-1-yl}-benzoylamino]-propionate;

(36) (2S)-benzenesulfonylamino-3-[4-{cis-3,5-dimethyl-4-(pyrimidin-2-yl)-piperazin-1-yl}-benzoylamino]-propionic acid;

(37) (2S)-benzenesulfonylamino-3-[4-{cis-3,5-dimethyl-4-(1,4,5,6-tetrahydropyrimidin-2-yl)-piperazin-1-yl}-benzoylamino]-propionic acid;

(38) t-butyl 3-[4-{4-(1H-benzimidazol-2-yl)-piperazin-1-yl}-benzoylamino]-(2S)-benzyloxycarbonylamino-propionate;

(39) 3-[4-{4-(1H-benzimidazol-2-yl)-piperazin-1-yl}-benzoylamino]-(2S)-benzyloxycarbonylamino-propionic acid;

(40) t-butyl (2S)-benzenesulfonylamino-3-[propyl-[4-{4-(pyrimidin-2-yl)-piperazin-1-yl}-benzoyl]-amino]-propionate;

(41) (2S)-benzenesulfonylamino-3-[propyl-[4-{4-(pyrimidin-2-yl)-piperazin-1-yl}-benzoyl]-amino]-propionic acid;

(42) (2S)-benzenesulfonylamino-3-[propyl-[4-{4-(1,4,5,6-tetrahydropyrimidin-2-yl)-piperazin-1-yl}-benzoyl]-amino]-propionic acid;

(43) (2S)-t-butoxycarbonylamino-3-[4-{4-(1,4,5,6-tetrahydropyrimidin-2-yl)-piperazin-1-yl}-benzoylamino]-propionic acid;

(44) t-butyl 2-(benzenesulfonyl-methyl-amino)-3-[4-{4-(pyrimidin-2-yl)-piperazin-1-yl}-benzoylamino]-propionate;

(45) 2-(benzenesulfonyl-methyl-amino)-3-[4-{4-(pyrimidin-2-yl)-piperazin-1-yl}-benzoylamino]-propionic acid;

(46) 2-(benzenesulfonyl-methyl-amino)-3-[4-{4-(1,4,5,6-tetrahydropyrimidin-2-yl)-piperazin-1-yl}-benzoylamino]-propionic acid;

(47) t-butyl 2-(benzenesulfonyl-hexyl-amino)-3-[4-{4-(pyrimidin-2-yl)-piperazin-1-yl}-benzoylamino]-propionate;

(48) 2-(benzenesulfonyl-hexyl-amino)-3-[4-{4-(pyrimidin-2-yl)-piperazin1-yl}-benzoylamino]-propionic acid;

(49) 2-(benzenesulfonyl-hexyl-amino)-3-[4-{4-(1,4,5,6-tetrahydropyrimidin-2-yl)-piperazin-1-yl}-benzoylamino]-propionic acid;

(50) (2S)-(3-hydroxycarbamoyl-propionylamino)-3-[4-{(1,4,5,6-tetrahydropyrimidin-2-yl)-piperazin-1-yl}-benzoylamino]-propionic acid;

(51) t-butyl (2S)-benzenesulfonylamino-3-[3-fluoro-4-{4-(pyrimidin-2-yl)-piperazin-1-yl}-benzoylamino]-propionate;

(52) (2S)-benzenesulfonylamino-3-[3-fluoro-4-{4-(pyrimidin-2-yl)-piperazin-1-yl}-benzoylamino]-propionic acid;

(53) (2S)-benzenesulfonylamino-3-[3-fluoro-4-{4-(1,4,5,6-tetrahydropyrimidin-2-yl)-piperazin-1-yl}-benzoylamino]-propionic acid;

(54) t-butyl (2S)-benzenesulfonylamino-3-[2-fluoro-4-{4-(pyrimidin-2-yl)-piperazin-1-yl}-benzoylamino]-propionate;

(55) (2S)-benzenesulfonylamino-3-[2-fluoro-4-{4-(pyrimidin-2-yl)-piperazin-1-yl}-benzoylamino]-propionic acid;

(56) (2S)-benzenesulfonylamino-3-[2-fluoro-4-{4-(1,4,5,6-tetrahydropyrimidin-2-yl)-piperazin-1-yl}-benzoylamino]-propionic acid;

(57) t-butyl (2S)-benzenesulfonylamino-3-[3-chloro-4-{4-(pyrimidin-2-yl)-piperazin-1-yl}-benzoylamino]-propionate;

(58) (2S)-benzenesulfonylamino-3-[2-chloro-4-{4-(pyrimidin-2-yl)-piperazin-1-yl}-benzoylamino]-propionic acid;

(59) (2S)-benzenesulfonylamino-3-[3-chloro-4-{4-(1,4,5,6-tetrahydropyrimidin-2-yl)-piperazin-1-yl}-benzoylamino]-propionic acid;

(60) t-butyl (2S)-benzenesulfonylamino-3-[2-chloro-4-{4-(pyrimidin-2-yl)-piperazin-1-yl}-benzoylamino]-propionate;

(61) (2S)-benzenesulfonylamino-3-[2-chloro-4-{4-(pyrimidin-2-yl)-piperazin-1-yl}-benzoylamino]-propionic acid;

(62) (2S)-benzenesulfonylamino-3-[2-chloro-4-{4-(1,4,5,6-tetrahydropyrimidin-2-yl)-piperazin-1-yl}-benzoylamino]-propionic acid;

(63) t-butyl (2S)-benzenesulfonylamino-3-[3-nitro-4-{4-(pyrimidin-2-yl)-piperazin-1-yl}-benzoylamino]-propionate;

(64) (2S)-benzenesulfonylamino-3-[2-nitro-4-{4-(pyrimidin-2-yl)-piperazin-1-yl}-benzoylamino]-propionic acid;

(65) 3-[3-amino-2-chloro-4-{4-(1,4,5,6-tetrahydropyrimidin-2-yl)-piperazin-1-yl}-benzoylamino]-(2S)-benzenesulfonylamino-propionic acid;

(66) t-butyl (2S)-benzyloxycarbonylamino-3-[4-{(3S)-methyl-4-(pyrimidin-2-yl)-piperazin-1-yl}-benzoylamino]-propionate;

(67) (2S)-benzyloxycarbonylamino-3-[4-{(3S)-methyl-4-(pyrimidin-2-yl)-piperazin-1-yl}-benzoylamino]-propionic acid;

(68) (2S)-amino-3-[4-{(3S)-methyl-4-(1,4,5,6-tetrahydropyrimidin-2-yl)-piperazin-1-yl}-benzoylamino]-propionic acid;

(69) (2S)-benzyloxycarbonylamino-3-[4-{(3S)-methyl-4-(1,4,5,6-tetrahydropyrimidin-2-yl)-piperazin-1-yl}-benzoylamino]-propionic acid;

(70) t-butyl (2S)-benzenesulfonylamino-3-[3-fluoro-4-{(3S)-methyl-4-(pyrimidin-2-yl)-piperazin-1-yl}-benzoylamino]-propionate;
(71) (2S)-benzenesulfonylamino-3-[3-fluoro-4-{(3S)-methyl-4-(pyrimidin-2-yl)-piperazin-1-yl}-benzoylamino]-propionic acid;
(72) (2S)-benzenesulfonylamino-3-[3-fluoro-4-{(3S)-methyl-4-(1,4,5,6-tetrahydropyrimidin-2-yl)-piperazin-1-yl}-benzoylamino]-propionic acid;
(73) t-butyl (2S)-benzyloxycarbonylamino-3-[3-fluoro-4-{4-(pyrimidin-2-yl)-piperazin-1-yl}-benzoylamino]-propionate;
(74) (2S)-benzyloxycarbonylamino-3-[3-fluoro-4-{4-(pyrimidin-2-yl)-piperazin-1-yl}-benzoylamino]-propionic acid;
(75) (2S)-amino-3-[3-fluoro-4-{4-(1,4,5,6-tetrahydropyrimidin-2-yl)-piperazin-1-yl}-benzoylamino]-propionic acid;
(76) (2S)-benzyloxycarbonylamino-3-[3-fluoro-4-{4-(1,4,5,6-tetrahydropyrimidin-2-yl)-piperazin-1-yl}-benzoylamino]-propionic acid;
(77) t-butyl (2S)-ethylamino-3-[3-fluoro-4-{4-(pyrimidin-2-yl)-piperazin-1-yl}-benzoylamino]-propionate;
(78) (2S)-ethylamino-3-[3-fluoro-4-{4-(pyrimidin-2-yl)-piperazin-1-yl}-benzoylamino]-propionic acid;
(79) (2S)-ethylamino-3-[3-fluoro-4-{4-(1,4,5,6-tetrahydropyrimidin-2-yl)-piperazin-1-yl}-benzoylamino]-propionic acid;
(80) t-butyl (2S)-amino-3-[3-fluoro-4-{4-(pyrimidin-2-yl)-piperazin-1-yl}-benzoylamino]-propionate;
(81) t-butyl 3-[3-fluoro-4-{4-(pyrimidin-2-yl)-piperazin-1-yl}-benzoylamino]-(2S)-(2,4,6-trimethyl-benzenesulfonylamino)-propionate;
(82) 3-[3-fluoro-4-{4-(pyrimidin-2-yl)-piperazin-1-yl}-benzoylamino]-(2S)-(2,4,6-trimethyl-benzenesulfonylamino)-propionic acid;
(83) 3-[3-fluoro-4-{4-(1,4,5,6-tetrahydropyrimidin-2-yl)-piperazin-1-yl}-benzoylamino]-(2S)-(2,4,6-trimethyl-benzenesulfonylamino)-propionic acid;
(84) t-butyl (2S)-amino-3-[4-{4-(pyrimidin-2-yl)-piperazin1-yl}-benzoylamino]-propionate;
(85) (2S)-amino-3-[4-{4-(pyrimidin-2-yl)-piperazin-1-yl}-benzoylamino]-propionic acid;
(86) ethyl 3-[4-{4-(pyrimidin-2-yl)-piperazin-1-yl}-benzoylamino]-propionate; and
(87) 3-[4-{4-(pyrimidin-2-yl)-piperazin-1-yl}-benzoylamino]-propionic acid.

The compounds according to the present invention may form pharmacologically acceptable salts thereof. Such salts include non-toxic salts. Preferred salts include hydrohalogenic acid salts such as hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, or maleic acid salts; amino acid salts such as glutamic acid salts or aspartic acid salts; alkali metal or alkaline earth metal salts such as sodium salts, potassium salts, and calcium salts; and organic alkali salts such as pyridine salts or triethylamine salts.

The compounds according to the present invention may form solvates (for example, hydrates or ethanolate).

Production of compounds

Compounds represented by formula (I), wherein X and Z both represent nitrogen, may be produced according to the following scheme:

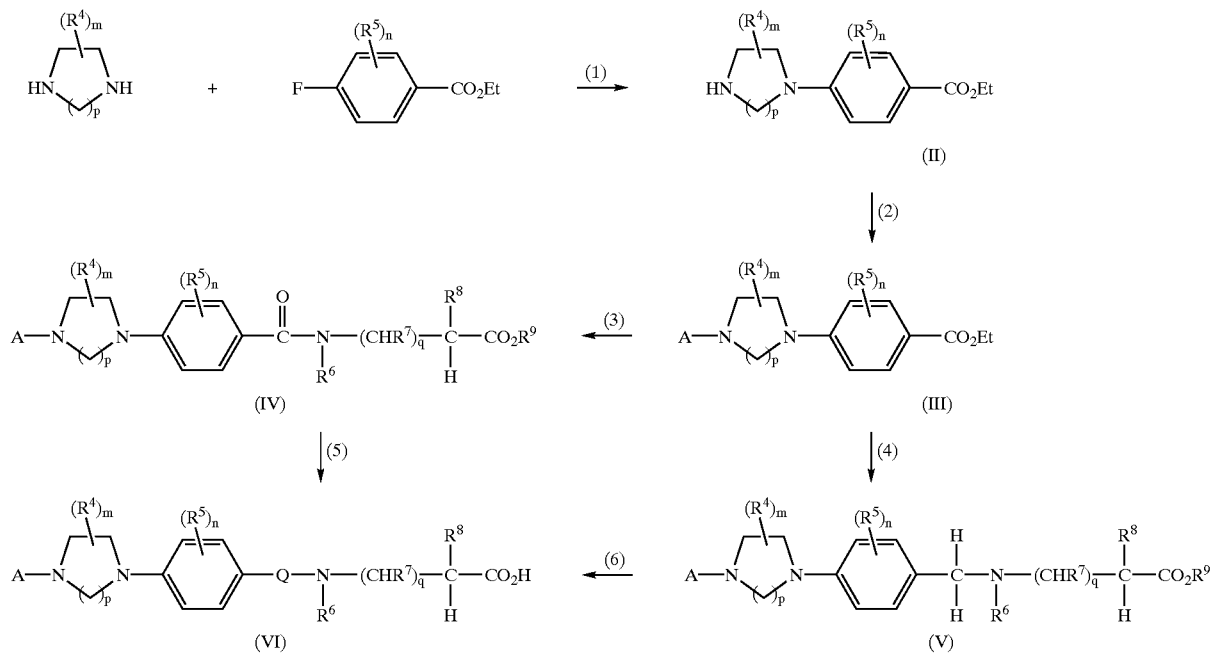

<Step 1>

An optionally substituted ethyl 4-fluorobenzoate may be reacted with piperazine or homopiperazine which is optionally substituted at the carbon atom(s) (hereinafter referred to simply as "piperazine derivative") in the presence of a reaction solvent, such as dimethyl sulfoxide or sulfolane (preferably dimethyl sulfoxide), at 50 to 150° C., preferably 80 to 120° C., to prepare a compound represented by formula (II). In this reaction, an organic base such as diisopropylethylamine may be added as an acid scavenger.

In addition to ethyl 4-fluorobenzoate, other ester compounds, for example, methyl, propyl, butyl, or benzyl ester compounds may be used as the starting compound.

Further, in addition to ethyl 4-fluorobenzoate, other 4-halogenobenzoates which have been substituted at the 4-position, for example, ethyl 4-iodobenzoate and ethyl 4-bromobenzoate, may be used. Among them, the use of ethyl 4-fluorobenzoate is preferred from the viewpoint of yield.

Furthermore, in addition to ethyl 4-fluorobenzoate, optionally substituted 4-fluorobenzonitrile may be used as the starting compound. In this case, in a proper later step, for example, acid hydrolysis or the like may be performed for conversion to a free carboxyl group, thereby producing a compound represented by formula (VI).

In the above scheme, a piperazine derivative, wherein one of the secondary amines has been previously protected, may be used for the production of the compound represented by formula (II). In this case, after a proper reaction step, the protective group may be removed followed by introduction of a new substituent into the secondary amine.

<Step 2>

Group A may be introduced into the free secondary amine in the compound represented by formula (II) to produce a compound represented by formula (III). The N—C bond between the compound represented by formula (II) and group A may be formed by reacting the compound represented by formula (II) with a reagent, such as optionally modified or substituted 2-bromopyrimidine, 2-chlorobenzimidazole, or 2-methylthio-2-imidazoline, in the presence of a reaction solvent, such as dimethylformamide, dimethyl sulfoxide, sulfolane, pyridine, or methanol, preferably dimethylformamide, at 50 to 1500° C., preferably 60 to 120° C.

Reagents usable in this step is not limited to those recited herein, and any reagent may be used so far as a carbon atom attached to two nitrogen atoms finally combines with the nitrogen atom in the secondary amine in the piperazine derivative portion to form a single bond.

An organic base, such as diisopropylethylamine, N-methylmorpholine, dimethylaminopyridine, or triethylamine, is preferably added as an acid scavenger from the viewpoint of improving the yield. The addition of 2 to 10 equivalents of diisopropylethylamine is preferred.

In the scheme, the bonding of the benzoic acid portion to the piperazine derivative is followed by the introduction of a basic atomic group, for example, pyrimidine or benzimidazole, into the secondary amine in the piperazine derivative portion. The production process of the compound represented by formula (III) is not always limited to the above process. The compound represented by formula (III) may also be produced by reacting ethyl 4-fluorobenzoate with a piperazine derivative with a basic atomic group, for example, pyrimidine or beonzimidazole, bonded thereto.

<Step 3>

The carboxylic ester represented by formula (III) may be hydrolyzed, followed by the formation of an amide bond to produce a compound represented by formula (IV). More specifically, a free carboxyl group prepared by hydrolysis with an alkali according to a conventional method is reacted with an amine represented by formula $R^6HNCHR^7CHR^8COOR^9$ wherein $R^6$, $R^7$, $R^{8,}$ and $R^9$ are as defined in formula (I) to perform condensation reaction, thereby producing the amide compound represented by formula (IV).

Among the compounds represented by formula (IV), compounds having an optionally substituted pyrimidine ring may be, if necessary, reduced to a corresponding tetrahydropyrimidine.

In the condensation reaction, a condensing agent, such as dicyclohexylcarbodiimide, diisopropylcarbodiimide, or 1-ethyl-3-(3-dimethylaminopropyl)carbodiimide hdyrochloride, may be used either solely or in combination with a peptide synthesis reagent, such as N-hydroxysuccinimide, 1-hydroxybenzotriazole, or benzotriazol-1-yloxytri(dimethylamino)phosphonium hexafluorophosphate. The combination of these reagents permits the desired condensation reaction to proceed with high efficiency. The use of a combination of 1 to 3 equivalents of 1-ethyl-3-(3-dimethylaminopropyl)carbodiimide hydrochloride with 1 to 2 equivalents of 1-hydroxybenzotriazole is preferred from the viewpoint of optimizing the yield.

Reaction solvents usable in the condensation reaction include dimethylformamide, dioxane, and tetrahydrofuran. Among them, dimethylformamide is preferred. The reaction may be carried out at 0 to 80° C., preferably 20 to 60° C.

In the condensation reaction, a tertiary amine, such as diisopropylethylamine, N-methylmorpholine, dimethylaminopyridine, or triethylamine, may be added as an organic base from the viewpoint of improving the yield. Among these tertiary amines, N-methylmorpholine is preferably added in an amount of 2 to 10 equivalents.

For the production of the compound represented by formula (IV) from the compound represented by formula (II) as the starting compound, the scheme represents, as a representative embodiment, the process which produces the contemplated compound through the compound represented by formula (III). However, the process, which produces the compound represented by formula (IV) from the compound represented by formula (II), is not limited to the above. Specifically, the compound represented by formula (IV) may be produced by previously protecting the secondary amine in the piperazine derivative portion of the compound represented by formula (II), converting the benzoic acid ester to a free carboxyl group, forming an amide bond, removing the protective group in the piperazine derivative portion, and introducing a basic atomic group, for example, pyrimidine or benzimidazole, into the secondary amine (see intermediate 20 and Example 34).

<Step 4>

The carboxylic acid ester represented by formula (III) may be converted to a corresponding aldehyde through one or two steps, followed by reductive amination to produce the compound represented by formula (V). For example, a free aldehyde group prepared through reduction and oxidation is reductively reacted with an amine represented by $R^6HNCHR^7CHR^8COOR^9$ wherein $R^6$, $R^7$, $R^8$, and $R^9$ are as defined in formula (I) to produce the amine represented by formula (V).

In the scheme, the carboxylic acid ester represented by formula (III) may be converted to a corresponding aldehyde by a conventional or novel method. Specifically, the corresponding aldehyde may be produced in one step by a suitable reduction reaction of the carboxylic acid ester. Alternatively, the carboxylic acid ester may be first suitably reduced to prepare a primary alcohol which is then suitably oxidized to produce the contemplated aldehyde. The process for producing the contemplated aldehyde in two steps will be exemplified.

A hydride reducing reagent, for example, two to three equivalents of diisobutylaluminum hydride, is allowed to act on the carboxylic acid ester as the compound represented by formula (III) in an aprotic solvent, for example, methylene chloride, at low temperature to convert the carboxylic acid ester to a corresponding benzyl alcohol. Next, the alcohol may be oxidized with an oxidizing reagent, such as manganese dioxide, chromium oxide, pyridinium chlorochromate, or pyridinium dichromate, in an organic solvent inert to the oxidation reaction to convert the alcohol to the corresponding aldehyde, preferably reacted with active manganese dioxide in ethyl acetate at room temperature, to produce the contemplated aldehyde.

Reducing reagents usable in the reductive amination reaction include sodiumboroncyanohydride, sodiumboronhydride, and sodiumborontriacetoxyhydride. Among them, sodiumboroncyanohydride is preferably used in an amount of 1 to 5 equivalents. Reaction solvents usable herein include dimethylformamide, methylene chloride, methanol, and acetic acid. The addition of a minor amount of acetic acid to a mixed solvent composed of methylene chloride and methanol to adjust the hydrogen ion concentration (pH) of the reaction solution to 3 to 4 is preferred. The reaction temperature is suitably 0 to 30° C., preferably 20 to 25° C.

The compounds represented by formula (V) prepared by the reductive amination, compounds, wherein $R^6$ represents a group other than the hydrogen atom, may be produced by the step of other reaction than described above. Specifically, the free aldehyde group may be reductively reacted with an amine represented by

$H_2NCHR^7CHR^8COOR^9$ wherein $R^7$, $R^8$, and $R^9$ are as defined in formula (I), to produce, among the compounds represented by formula (V), a compound wherein $R^6$ represents a hydrogen atom. Thereafter, the product may be further reductively aminated to introduce an alkyl, alkenyl, or aralkyl group into $R^6$. The introduction of the alkyl, alkenyl, or aralkyl group into $R^6$ is not always carried out for the compound represented by formula (V) in the scheme. Specifically, the introduction of the alkyl, alkenyl, or aralkyl group into $R^6$ may be carried out for the compound represented by formula (VI) in the scheme (see Examples 23, 25, and 26).

In this reaction, $R^9$ in —$COOR^9$ corresponding to the carboxylic acid ester portion of the amine may be a hydrogen atom.

<Steps 5 and 6>

The carboxylic acid ester portion in the compound represented by formula (IV) or (V) in the scheme may be optionally converted to a free carboxyl group to produce the compound represented by formula (VI).

The carboxylic acid ester portion in the compound represented by formula (IV) or (V) may be converted to the contemplated free carboxyl group by a conventional method, for example, by hydrolysis with an alkali, hydrolysis with an acid, or reaction with an acid. The deesterification reaction may be achieved by a novel method without any restriction or limitation.

The compound represented by formula (IV) or (V) as such is an orally administrable integrin $\alpha_v\beta_3$ antagonist and/or GP IIb/IIIa antagonist. Therefore, the step of converting the carboxylic acid ester to the free carboxyl group is not always necessary.

Among the compounds represented by formula (VI), compounds having an optionally substituted pyrimidine ring may be optionally reduced to a corresponding tetrahydropyrimidine. The reduction may be carried by a conventional method. Examples of reduction methods usable herein include catalytic reduction in the presence of a catalyst, such as palladium-carbon, ruthenium-carbon, rhodium-carbon, palladium oxide, platinum oxide, ruthenium oxide, rhodium platinum oxide complex, rhodium aluminum oxide complex, Raney nickel, or palladium black, and a reaction, for example, with metallic sodium or metallic lithium in liquid ammonia. Preferably, the reduction is carried out in an acidic solvent, for example, in acetic acid acidified with hydrochloric acid, in the presence of palladium-carbon with hydrogen under normal or applied pressure.

In the scheme, for example, the compound represented by formula (III) is first converted to the compound represented by formula (IV) to form an amide bond, followed by reduction of an optionally substituted pyrimidine ring in the compound represented by formula (VI). However, for example, a basic functional group, for example, an optionally substituted pyrimidine ring, bonded to the secondary amino group of the piperazine derivative among the compound represented by formula (III) may be reduced followed by amide bond formation.

In the compounds represented by formula (IV), (V), and (VI) in the scheme, functional groups, which have been constructed in the molecule, for example, $R^4$, $R^5$, $R^7$, and $R^8$, may be optionally converted. Regarding the conversion of $R^8$ in the compound represented by formula (VI), reference may be made to Examples 29, 30, 44, 47, 68, 69, 75, 76, 80, 81, and 84.

The compound represented by formula (I), wherein X represents CH and Z represents N, may be produced, for example, by reacting isonipecotic acid with 4-fluorobenzoic acid according to step 1 to prepare the phenylpiperidine derivative corresponding to formula (II) which is then subjected to steps 2 to 5. Group A may be introduced, for example, by reacting, before the reaction of isonipecotic acid with 4-fluorobenzoic acid, isonipecotic acid with 1,2-phenylenediamine under acidic conditions (for example, in the presence of concentrated hydrochloric acid or polyphosphoric acid) at a temperature of 100 to 200° C., preferably 180° C.

The compound represented by formula (I), wherein X represents N and Z represents CH, may be produced from 4-bromobenzyl alcohol with a protected hydroxyl group according to the method described in WO 94/12181. More specifically, the phenylpiperidine derivative corresponding to formula (II) may be produced by (1) reacting 4-bromobenzyl alcohol with lithium introduced thereinto (with a protected hydroxyl group) with N-Boc-4-piperidone to prepare a phenylpiperidine derivative, (2) reductively removing the resultant hydroxyl group, (3) removing the protective group from the protected hydroxyl group, (4) esterifying the deprotected hydroxyl group, and (5) removing the Boc group. The compound represented by formula (I), wherein X represents N and Z represents CH, may be produced from this phenylpiperidine derivative through steps 2 to 5.

Use of compounds/pharmaceutical composition

The compounds according to the present invention have potent integrin $\alpha_v\beta_3$ antagonistic activity, as demonstrated in Pharmacological Test Example 1. The integrin $\alpha_v\beta3$ mediates cardiovascular diseases such as acute myocardial infarction, neointima formation hypertrophy, restenosis after PTCA/stent operation, unstable angina, acute coronary syndrome, angina pectoris after PTCA/stent operation, or arterial sclerosis, particularly atherosclerosis; angiogenesis-related diseases such as diabetic retinopathy, diabetic vascular complication, or vascular grafting; cerebrovascular diseases such as cerebral infarction; cancers such as solid tumors or metastasis thereof; immunological diseases such as arthritis, particularly rheumatic arthritis; and osteopathy such as osteoporosis, hypercalcemia, periodontitis, hyperparathyroidism, periarticular sore, or Paget's diseases (DN & P, 10 (8), 456 (1997)). Accordingly, the compounds according to the present invention can be used in the treatment of these diseases. The term "therapy" or "treatment" as used herein includes "prevention" or "prophylaxis."

As described in Pharmacological Test Example 2, the compounds according to the present invention have GP IIb/IIIa antagonistic activity and human platelet aggregation inhibitory activity. Therefore, the compounds according to the present invention can be used in the treatment of platelet thrombosis and thromboembolism during and after the treatment of thrombolysis and after angioplasty of the coronary artery and other arteries and after bypassing of the coronary artery, the improvement of peripheral circulating blood stream, and the inhibition of blood clotting during extracorporeal circulation. Furthermore, the compounds according to the present invention can be used in the treatment of thrombotic thrombocytopenic purpura and hemolytic uremic syndrome (Gendai Iryo, 29, (11), 2753 (1997)).

Not only compounds represented by formula (I) wherein $R^9$ represents an alkyl group, but also compounds represented by formula (I) wherein $R^9$ represents a hydrogen atom, for example, compounds prepared in Examples 3 and 5, had excellent oral absorption in rats (data not shown). Therefore, any of the compounds, wherein $R^9$ represents an alkyl group or a hydrogen atom, can be used in the treatment of the above diseases.

The compounds according to the present invention and pharmacologically acceptable salts and solvates thereof can be administered orally or parenterally by administration routes, for example, inhalation administration, rhinenchysis, instillation, subcutaneous administration, intravenous injection, intravenous drip infusion, intramuscular injection, rectal administration, or percutaneous administration, and thus may be formed into appropriate various dosage forms depending on oral or parenteral administration routes and administered to human and non-human animals.

The compounds according to the present invention may be formulated into, for example, oral preparation, such as tablets, capsules, granules, powders, pills, particulates, troches, syrups, or emulsions; liquids for external use such as inhalants, nasal drops, or eye drops; injections such as intravenous injections or intramuscular injections; intravenous drip infusions; preparations for rectal administrations; oleaginous suppositories; water-soluble suppositories; and liniments such as ointments depending upon applications thereof.

These various preparations may be prepared by conventional methods with commonly used components, for example, excipients, extenders, binders, humidifiers, disintegrants, surface active agents, lubricants, dispersants, buffers, preservatives, dissolution aids, antiseptics, flavoring agents, analgesic agents, stabilizers and the like. Non-toxic additives usable herein include, for example, lactose, fructose, glucose, starch, gelatin, magnesium carbonate, synthetic magnesium silicate, talc, magnesium stearate, methylcellulose, carboxymethylcellulose or a salt thereof, gum arabic, olive oil, propylene glycol, polyethylene glycol, syrup, petrolatum, glycerin, ethanol, citric acid, sodium chloride, sodium sulfite, sodium phosphate, ascorbic acid, and cyclodextrins.

The content of the compound according to the present invention in the medicament may vary according to the dosage form. In general, however, the content is generally 1 to 70% by weight, preferably 5 to 50% by weight, based on the whole composition. The dose for the treatment and prevention of coronary diseases may be appropriately determined in consideration of, for example, the dosage route and the age, sex and severity of condition of patients, and the preparation may be administered usually in an amount of about 0.1 to 2,000 mg, preferably about 5 to 400 mg per day per adult. This dose is administered at a time daily, divided doses of several times daily, or at a time every several days.

EXAMPLES

The present invention will be described in more detail with reference to the following examples, though it is not limited to these examples only.

Intermediate 1: Ethyl 4-(piperazin-1-yl)-benzoate

Dimethyl sulfoxide (10 ml) was added to 5.2 g of piperazine to prepare a suspension, and 2.5 g of ethyl 4-fluorobenzoate was added to the suspension. The mixture was stirred at 120° C. for 20 hr and was then cooled to room temperature, and the reaction solution was concentrated under the reduced pressure. The residue was purified by column chromatography on silica gel (development system: methylene chloride-methanol-concentrated aqueous ammonia=900:100:1) to prepare 3.3 g of the title compound.

Physicochemical Properties of Intermediate 1

(1) Color and form: Colorless solid
(2) Molecular formula: $C_{13}H_{18}N_2O_2$
(3) Mass spectrum (TSP (thermospray) MS): m/z 235 (M+H)$^+$
(4) $^1$H NMR spectrum (400 MHz, CDCl$_3$) δ (ppm): 1.37 (3H, t, CH$_2$C$\underline{H}_3$), 3.02 (4H, m, piperazine), 3.28 (4H, m, piperazine), 4.32 (2H, q, C$\underline{H}_2$CH$_3$), 6.86 (2H, d, C$_6$H$_4$), 7.92 (2H, d, C$_6$H$_4$)

Intermediate 2: Ethyl 4-{4-(pyrimidin-2-yl)-piperazin-1-yl}-benzoate

Dimethylformamide (4.0 ml) was added to 114 mg of intermediate 1 to prepare a solution, and 76 mg of 2-bromopyrimidine was added to the solution. Diisopropylethylamine (0.4 ml) was added to the mixture. The mixture was stirred at 120° C. for 4.5 hr and was then cooled to room temperature, followed by concentration under the reduced pressure. The residue was purified by column chromatography on silica gel (development system: methylene chloride-methanol-concentrated aqueous ammonia=950:50:1) to prepare 142 mg of the title compound.

Physicochemical Properties of Intermediate 2

(1) Color and form: Colorless solid
(2) Molecular formula: $C_{17}H_{20}N_4O_2$
(3) Mass spectrum (TSPMS): m/z 313 (M+H)$^+$
(4) $^1$H NMR spectrum (400 MHz, CDCl$_3$) δ (ppm): 1.37 (3H, t, CH$_2$C$\underline{H}_3$), 3.43 (4H, m, piperazine), 3.99 (4H, m, piperazine), 4.33 (2H, q, C$\underline{H}_2$CH$_3$), 6.54 (1H, t, pyrimidine), 6.90 (2H, d, C$_6$H$_4$), 7.94 (2H, d, C$_6$H$_4$), 8.34 (2H, d, pyrimidine)

Intermediate 3: 4-{4-(Pyrimidin-2-yl)-piperazin-1-yl}-benzoic acid

Methanol (5.0 ml) and 25 ml of tetrahydrofuran were added to 127 mg of intermediate 2 to prepare a solution, and 25 ml of a 1 N aqueous sodium hydroxide solution was added to the solution. The mixture was stirred at 40° C. for 5 hr, and was then cooled to room temperature. The system was adjusted to pH 6 to 8 by the addition of 1 N hydrochloric acid, and then concentrated under the reduced pressure. The residue was purified by column chromatography on silica gel (development system: methylene chloride-methanol-water-concentrated aqueous ammonia=8:8:1:1) to prepare 128 mg of the title compound.

Physicochemical Properties of Intermediate 3
(1) Color and form: Colorless solid
(2) Molecular formula: $C_{15}H_{16}N_4O_2$
(3) Mass spectrum (TSPMS): m/z 285 (M+H)$^+$
(4) $^1$H NMR spectrum (400 MHz, CD$_3$OD) δ (ppm): 3.35 (4H, m, piperazine), 3.95 (4H, m, piperazine), 6.60 (1H, t, pyrimidine), 6.97 (2H, d, C$_6$H$_4$), 7.87 (2H, d, C$_6$H$_4$), 8.33 (2H, d, pyrimidine)

Example 1 t-Butyl (2S)-benzenesulfonylamino-3-[4-{4-(pyrimidin-2-yl)-piperazin-1-yl}-benzoylamino]-propionate Dimethylformamide (60 ml) was added to 734 mg of intermediate 3 to prepare a solution. t-Butyl (2S)-benzenesulfonyl-2,3-diaminopropionate (860 mg) was added to the solution. Further, 523 mg of 1-hydroxybenzotriazole, 1.5 ml of N-methylmorpholine, and 758 mg of 1-ethyl-3-(3-dimethylaminopropyl) carbodiimide hydrochloride were added thereto, followed by stirring at room temperature for 24 hr. A saturated aqueous sodium hydrogencarbonate solution (500 ml) was added to the mixture to stop the reaction, and 500 ml of methylene chloride was added thereto. The organic layer was separated, dried over anhydrous magnesium sulfate, and then concentrated under the reduced pressure. The residue was purified by column chromatography on silica gel (development system: hexane-ethyl acetate=1:2) to prepare 1.0 g of the title compound.

Physicochemical Properties of Compound Prepared in Example 1
(1) Color and form: Colorless solid
(2) Molecular formula: $C_{28}H_{34}N_6O_5S$
(3) Mass spectrum (TSPMS): m/z 567 (M+H)$^+$
(4) $^1$H NMR spectrum (400 MHz, CDCl$_3$) δ (ppm): 1.27 (9H, s, t-Bu), 3.39 (4H, m, piperazine), 3.57 (1H, m, CONHC$\underline{H}_2$CH), 3.89 (2H, m, CONHC$\underline{H}_2$C$\underline{H}$), 3.99 (4H, m, piperazine), 6.53 (1H, t, pyrimidine), 6.93 (2H, d, C$_6$H$_4$), 7.49 (2H, m, C$_6$H$_5$), 7.57 (1H, m, C$_6$H$_5$), 7.73 (2H, d, C$_6$H$_4$), 7.86 (2H, m, C$_6$H$_5$), 8.33 (2H, d, pyrimidine)

Example 2

(2S)-Benzenesulfonylamino-3-[4-{4-(pyrimidin-2-yl)-piperazin-1-yl}-benzoylamino]-propionic acid Methylene chloride (4.0 ml) was added to 51 mg of the compound prepared in Example 1 to prepare a solution. Trifluoroacetic acid (2.0 ml) was added at room temperature to the solution, and the mixture was stirred at that temperature for 3 hr before the reaction solution was concentrated under the reduced pressure. The concentrate was purified by preparative thin-layer chromatography on silica gel (development system: methylene chloride-ethanol-water-concentrated aqueous ammonia=8:8:1:1), and then purified by Sephadex LH-20 (development system: methanol) to prepare 46 mg of the title compound.

Physicochemical Properties of Compound Prepared in Example 2
(1) Color and form: Colorless solid
(2) Molecular formula: $C_{24}H_{26}N_6O_4S$
(3) Mass spectrum (TSPMS): m/z 511 (M+H)$^+$
(4) Specific rotation: $[\alpha]_D^{25}$+63° (c 0.055, MeOH)
(5) $^1$H NMR spectrum (400 MHz, CD$_3$OD) δ (ppm): 3.30 (4H, m, piperazine), 3.46 (1H, dd, CONC$\underline{H}_2$CH), 3.57 (1H, dd, CONHC$\underline{H}_2$CH), 3.64 (1H, dd, CONHCH$_2$C$\underline{H}$), 3.87 (4H, m, piperazine), 6.52 (1H, t, pyrimidine), 6.92 (2H, d, C$_6$H$_4$), 7.36 (2H, m, C$_6$H$_5$), 7.42 (1H, m, C$_6$H$_5$), 7.63 (2H, d, C$_6$H$_4$), 7.75 (2H, m, C$_6$H$_5$), 8.25 (2H, d, pyrimidine)

Example 3

(2S)-Benzenesulfonylamino-3-[4-{4-(1,4,5,6-tetrahydropyrimidin-2-yl)-piperazin-1-yl}-benzoylamino]-propionic acid Acetic acid (100 ml) and 10 ml of concentrated hydrochloric acid were added to 378 g of the compound prepared in Example 2 to prepare a solution, and 200 mg of 10% palladium-carbon was added to the solution. The mixture was vigorously shaken at room temperature under a hydrogen pressure of 3 atm for 4 hr. The insolubles were collected by filtration, and then washed twice with water. The filtrate was combined with the washings, followed by concentration under the reduced pressure. The residue was purified by preparative thin-layer chromatography on silica gel (development system: methylene chloride-ethanol-water-concentrated aqueous ammonia=8:8:1:1), and then purified by Sephadex LH-20(development system: methanol) to prepare 198 mg of the title compound.

Physicochemical Properties of Compound Prepared in Example 3
(1) Color and form: Colorless solid
(2) Molecular formula: $C_{24}H_{30}N_6O_4S$
(3) Mass spectrum (TSPMS): m/z 515 (M+H)$^+$
(4) Specific rotation: $[\alpha]_D^{25}$ +112° (c 0.048, MeOH)
(5) $^1$H NMR spectrum (400 MHz, CD$_3$OD) δ (ppm): 1.95 (2H, quintet, tetrahydropyrimidine), 3.37 (4H, m, piperazine), 3.40 (4H, m, tetrahydropyrimidine), 3.52 (4H, m, piperazine), 3.57 (1H, dd, CONHC$\underline{H}_2$CH), 3.64 (1H, dd, CONHC$\underline{H}_2$CH), 3.72 (1H, dd, CONHCH$_2$C$\underline{H}$), 6.91 (2H, d, C$_6$H$_4$), 7.47 (2H, m, C$_6$H$_5$), 7.53 (1H, m, C$_6$H$_5$), 7.72 (2H, d, C$_6$H$_4$), 7.85 (2H, m, C$_6$H$_5$)

Intermediate 4: Ethyl 4-([1,4]diazepan-1-yl)-benzoate

Ethyl 4-fluorobenzoate (1.2 g) was added to 1.4 g of homopiperazine to prepare a suspension. The suspension was stirred at 120° C. for 7.5 hr and was then cooled to room temperature, followed by purification by column chromatography on silica gel (development system: methylene chloride-methanol-concentrated aqueous ammonia= 900:100:1) to prepare 1.1 g of the title compound.

Physicochemical Properties of Intermediate 4
(1) Color and form: Colorless solid
(2) Molecular formula: $C_{14}H_{20}N_2O_2$
(3) Mass spectrum (TSPMS): m/z 249 (M+H)$^+$
(4) $^1$H NMR spectrum (400 MHz, CDCl$_3$) δ (ppm): 1.36 (3H, t, CH$_2$C$\underline{H}_3$), 1.89 (2H, m, homopiperazine), 2.82

(2H, m, homopiperazine), 3.03 (2H, m, homopiperazine), 3.61 (4H, m, homopiperazine), 4.31 (2H, q, C$\underline{H}_2$CH$_3$), 6.66 (2H, d, $\underline{C}_6$H$_4$), 7.89 (2H, d, C$_6$H$_4$)

Intermediate 5: Ethyl 4-{4-(pyrimidin-2-yl)-[1,4] diazepan-1-yl}-benzoate

Dimethylformamide (15 ml) was added to 250 mg of intermediate 4 to prepare a solution, and 160 mg of 2-bromopyrimidine was added to the solution. Diisopropylethylamine (2.0 ml) was added to the mixture. The mixture was stirred at 120° C. for 2 hr and was then cooled to room temperature, followed by concentration under the reduced pressure. The residue was purified by column chromatography on silica gel (development system: methylene chloride-methanol=100:1) to prepare 198 mg of the title compound.

Physicochemical Properties of Intermediate 5

(1) Color and form: Colorless solid (2) Molecular formula: C$_{18}$H$_{22}$N$_4$O$_2$ (3) Mass spectrum (APCI (atmospheric chemical ionization) MS): m/z 327 (M+H)$^+$ (4) $^1$H NMR spectrum (400 MHz, CDCl$_3$) δ (ppm): 1.36 (3H, t, CH$_2$C$\underline{H}_3$), 2.10 (2H, quintet, homopiperazine), 3.56 (2H, t, homopiperazine), 3.65 (2H, t, homopiperazine), 3.70 (2H, dd, homopiperazine), 3.99 (2H, dd, homopiperazine), 4.32 (2H, q, C$\underline{H}_2$CH$_3$), 6.47 (1H, t, pyrimidine), 6.70 (2H, d, C$_6$H$_4$), 7.90 (2H, d, C$_6$H$_4$), 8.28 (2H, d, pyrimidine)

Intermediate 6: 4-{4-(Pyrimidin-2-yl)-[1,4] diazepan-1-yl}-benzoic acid

Methanol (4.0 ml) and 20 ml of tetrahydrofuran were added to 103 mg of intermediate 5 to prepare a solution, and 20 ml of a 1 N aqueous sodium hydroxide solution was added to the solution. The mixture was stirred at 40° C. for 5 hr, and was then cooled to room temperature. The system was adjusted to pH 6 to 8 by the addition of 1 N hydrochloric acid, followed by concentration under the reduced pressure. The residue was purified by column chromatography on silica gel (development system: methylene chloride-methanol-water-concentrated aqueous ammonia=8:8:1:1) to prepare 94 mg of the title compound.

Physicochemical Properties of Intermediate 6

(1) Color and form: Colorless solid (2) Molecular formula: C$_{16}$H$_{18}$N$_4$O$_2$ (3) Mass spectrum (TSPMS): m/z 299 (M+H)$^+$ (4) $^1$H NMR spectrum (400 MHz, CDCl$_3$) δ (ppm): 2.12 (2H, quintet, homopiperazine), 3.58 (2H, t,homopiperazine), 3.67 (2H, t, homopiperazine), 3.73 (2H, m, homopiperazine), 4.01 (2H, m, homopiperazine), 6.49 (1H, t, pyrimidine), 6.73 (2H, d, C$_6$H$_4$), 7.95 (2H, d, C$_6$H$_4$), 8.30 (2H, d, pyrimidine)

Example 4 t-Butyl (2S)-benzenesulfonylamino-3-[4-{4-(pyrimidin-2-yl)-[1,4]diazepan-1-yl}-benzoylamino]-propionate Dimethylformamide (9.0 ml) was added to 94 mg of intermediate 6 to prepare a solution, and 125 mg of t-butyl (2S)-benzenesulfonyl-2,3-diaminopropionate was added to the solution. Further, 65 mg of 1-hydroxybenzotriazole, 0.18 ml of N-methylmorpholine, and 97 mg of 1-ethyl-3-(3-dimethylaminopropyl)carbodiimide hydrochloride were added to the mixture, and the mixture was stirred at room temperature for 26 hr. A saturated aqueous sodium hydrogencarbonate solution (100 ml) was added thereto to stop the reaction. Methylene chloride (100 ml) was added to the mixture. The organic layer was then separated, dried over anhydrous magnesium sulfate, and concentrated under the reduced pressure. The residue was purified by column chromatography on silica gel (development system: hexane-ethyl acetate=1:2) to prepare 172 mg of the title compound.

Physicochemical Properties of Compound Prepared in Example 4

(1) Color and form: Colorless solid (2) Molecular formula: C$_{29}$H$_{36}$N$_6$O$_5$S (3) Mass spectrum (APCIMS): m/z 581 (M+H)$^+$ (4) $^1$H NMR spectrum (400 MHz, CDCl$_3$) δ (ppm): 1.29 (9H, s, t-Bu), 2.10 (2H, quintet, homopiperazine), 3.55 (2H, t, homopiperazine), 3.58 (1H, ddd, CONHC$\underline{H}_2$CH), 3.68 (4H, m, homopiperazine), 3.86 (1H, ddd, CONHC$\underline{H}_2$CH), 3.93 (1H, m, CONHCH$_2$C$\underline{H}$), 4.01 (2H, m, homopiperazine), 6.47 (1H, t, pyrimidine), 6.71 (2H, d, C$_6$H$_4$), 7.47 (2H, m, C$_6$H$_5$), 7.54 (1H, m, C$_6$H$_5$), 7.68 (2H, d, C$_6$H$_4$), 7.86 (2H, m, C$_6$H$_5$), 8.29 (2H, d, pyrimidine)

Example 5

(2S)-Benzenesulfonylamino-3-[4-{4-(pyrimidin-2-yl)-[1,4]diazepan-1-yl}-benzoylamino]-propionic acid Methylene chloride (30 ml) was added to 400 mg of the compound prepared in Example 4 to prepare a solution. Trifluoroacetic acid (5.0 ml) was added at room temperature to the solution, and the mixture was stirred at that temperature for 8 hr before the reaction solution was concentrated under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system:methanol) to prepare 210 mg of the title compound.

Physicochemical Properties of Compound Prepared in Example 5

(1) Color and form: Colorless solid (2) Molecular formula: C$_{24}$H$_{28}$N$_6$O$_5$S (3) Mass spectrum (TSPMS): m/z 525 (M+H)$^+$ (4) Specific rotation: $[\alpha]_D^{25}$ +37° (c 0.068, MeOH)

(5) $^1$H NMR spectrum (400 MHz, CD$_3$OD) δ (ppm): 1.96 (2H, quintet, homopiperazine), 3.39 (1H, dd, CONHC$\underline{H}_2$CH), 3.50 (2H, m, homopiperazine), 3.56 (1H, dd, CONHC$\underline{H}_2$CH), 3.60 (2H, m, homopiperazine), 3.66 (2H, m, homopiperazine), 3.91 (2H, m, homopiperazine), 3.99 (1H, dd, CONHCH$_2$C$\underline{H}$), 6.43 (1H, t, pyrimidine), 6.67 (2H, d, C$_6$H$_4$), 7.27 (2H, m, C$_6$H$_5$), 7.32 (1H, m, C$_6$H$_5$), 7.48 (2H, d, C$_6$H$_4$), 7.70 (2H, m, C$_6$H$_5$), 8.17 (2H, d, pyrimidine)

Example 6

(2S)-Benzenesulfonylamino-3-[4-{4-(1,4,5,6-tetrahydropyrimidin-2-yl)-[1,4]diazepan-1-yl}-benzoylamino]-propionic acid Acetic acid (65 ml) and 6.5 ml of concentrated hydrochloric acid were added to 68 mg of the compound prepared in Example 5 to prepare a solution. 10% palladium-carbon (36 mg) was added to the solution, and the mixture was vigorously shaken at room temperature for 5 hr under a hydrogen pressure of 3 atm. The insolubles were collected by filtration, and then washed twice with water. The filtrate was combined with the washings, followed by concentration under the reduced pressure. The residue was dissolved in 2.0 ml of methanol. The solution was added to 200 ml of ice-cold diisopropyl ether to cause precipitation, thereby preparing 34 mg of trihydrochloride of the title compound.
Physicochemical Properties of Compound Prepared in Example 6
(1) Color and form: Pale yellow solid
(2) Molecular formula: $C_{25}H_{32}N_6O_5S$
(3) Mass spectrum (TSPMS): m/z 529 (M+H)$^+$
(4) Specific rotation: $[\alpha]_D^{25}$ +38° (c 0.14, MeOH) (as trihydrochloride)
(5) $^1$H NMR spectrum (400 MHz, CD$_3$OD) (as trihydrochloride) δ (ppm): 1.73 (2H, quintet, tetrahydropyrimidine), 1.97 (2H, quintet, homopiperazine), 3.25 (4H, m, tetrahydropyrimidine), 3.45 (1H, dd, CONHC$\underline{H}$2CH), 3.49 (2H, m, homopiperazine), 3.65 (2H, m, homopiperazine), 3.70 (2H, m, homopiperazine), 3.72 (1H, dd, CONHC$\underline{H}_2$CH), 3.82 (2H, m, homopiperazine), 4.18 (1H, dd, CONHCH$_2$C$\underline{H}$), 6.80 (2H, d, C$_6$H$_4$), 7.43 (2H, m, C$_6$H$_5$), 7.50 (1H, m, C$_6$H$_5$), 7.68 (2H, d, C$_6$H$_4$), 7.82 (2H, m, C$_6$H$_5$)

Intermediate 7: Ethyl 4-{3-methyl-(piperazin-1-yl)}-benzoate

Dimethyl sulfoxide (5.0 ml) was added to 1.2 g of (±)-2-methylpiperazine to prepare a suspension. Ethyl 4-fluorobenzoate (1.0 g) was added to the suspension, and the mixture was stirred at 120° C. for 6.5 hr and was then cooled to room temperature. The reaction solution was concentrated under the reduced pressure. The residue was purified by column chromatography on silica gel (development system: methylene chloride-methanol-concentrated aqueous ammonia=900:100:1) to prepare 1.1 g of the title compound.
Physicochemical Properties of Intermediate 7
(1) Color and form: pale yellow solid
(2) Molecular formula: $C_{14}H_{20}N_2O_2$
(3) Mass spectrum (TSPMS): m/z 249 (M+H)$^+$
(4) $^1$H NMR spectrum (400 MHz, CDCl$_3$) δ (ppm): 1.16 (3H, d, CH$_3$), 1.35 (3H, t, CH$_2$C$\underline{H}_3$), 2.49 (1H, dd, piperazine), 2.85 (1H, dt, piperazine), 2.95 (1H, dq, piperazine), 3.00 (1H, dt, piperazine), 3.14 (1H, dt, piperazine), 3.68 (2H, m, piperazine), 4.33 (2H, q, C$\underline{H}_2$CH$_3$), 6.86 (2H, d, C$_6$H$_4$), 7.92 (2H, d, C$_6$H$_4$)

Intermediate 8: Ethyl 4-{3-methyl-4-(pyrimidin-2-yl)-piperazin-1-yl}-benzoate

Dimethylformamide (20 ml) was added to 570 mg of intermediate 7 to prepare a solution, and 330 mg of 2-bromopyrimidine was added to the solution. Diisopropylethylamine (1.5 ml) was added to the mixture, and the mixture was stirred at 120° C. for 20 hr and was then cooled to room temperature, followed by concentration under the reduced pressure. The residue was purified by column chromatography on silica gel (development system: methylene chloride-methanol-concentrated aqueous ammonia= 200:10:1) to prepare 404 mg of the title compound.
Physicochemical Properties of Intermediate 8
(1) Color and form: pale yellow solid
(2) Molecular formula: $C_{18}H_{22}N_4O_2$
(3) Mass spectrum (TSPMS): m/z 327 (M+H)$^+$
(4) $^1$H NMR spectrum (400 MHz, CDCl$_3$) δ (ppm): 1.31 (3H, d, CH$_3$), 1.37 (3H, t, CH$_2$C$\underline{H}_3$), 3.08 (1H, ddd, piperazine), 3.28 (1H, dd, piperazine), 3.50 (1H, ddd, piperazine), 3.68 (1H, dt, piperazine), 3.79 (1H, ddt, piperazine), 4.33 (2H, q, C$\underline{H}_2$CH$_3$), 4.52 (1H, dt, piperazine), 4.95 (1H, m, piperazine), 6.52 (1H, t, pyrimidine), 6.86 (2H, d, C$_6$H$_4$), 7.94 (2H, d, C$_6$H$_4$), 8.34 (2H, d, pyrimidine)

Intermediate 9: 4-{3-Methyl-4-(pyrimidin-2-yl)-piperazin-2-yl}-benzoic acid

Methanol (2.5 ml) and 10 ml of tetrahydrofuran were added to 100 mg of intermediate 8 to prepare a solution, and 10 ml of a 1 N aqueous sodium hydroxide solution was added to the solution. The mixture was stirred at 50° C. for 5 hr and was then cooled to room temperature. The system was adjusted to pH 6 to 8 by the addition of 1 N hydrochloric acid, followed by concentration under the reduced pressure. The residue was purified by column chromatography on silica gel (development system:methylene chloride-methanol-water-concentrated aqueous ammonia=8:8:1:1) to prepare 68 mg of the title compound.
Physicochemical Properties of Intermediate 9
(1) Color and form: Colorless solid
(2) Molecular formula: $C_{16}H_{18}N_4O_2$
(3) Mass spectrum (TSPMS): m/z 299 (M+H)$^+$
(4) $^1$H NMR spectrum (400 MHz, CD$_3$OD) δ (ppm): 1.19 (3H, d, CH$_3$), 2.92
(1H, ddd, piperazine), 3.12 (1H, dd, piperazine), 3.37 (1H, ddd, piperazine), 3.71
(1H, dt, piperazine), 3.78 (1H, ddt, piperazine), 4.40 (1H, dt, piperazine), 4.81 (1H, m, piperazine), 6.51 (1H, t, pyrimidine), 6.86 (2H, d, C$_6$H$_4$), 7.79 (2H, d, C$_6$H$_4$), 8.25 (2H, d, pyrimidine)

Example 7 t-Butyl (2S)-benzenesulfonylamino-3-[4-{3-methyl-4-(pyrimidin-2-yl)-piperazin-1-yl}-benzoylamino]-propionate Dimethylformamide (2.0 ml) was added to 47 mg of intermediate 9 to prepare a solution, and 55 mg of t-butyl (2S)- benzenesulfonyl-2,3-diaminopropionate was added to the solution. Further, 34 mg of 1-hydroxybenzotriazole, 0.10 ml of N-methylmorpholine, and 58 mg of 1-ethyl-3-(3-dimethylaminopropyl)carbodiimide hydrochloride were added to the mixture, and the mixture was stirred at room temperature for 22 hr. A saturated aqueous sodium hydrogencarbonate solution (20 ml) was added to the mixture to stop the reaction, and 20 ml of methylene chloride was added thereto. The organic layer was then separated, dried over anhydrous magnesium sulfate, and concentrated under the reduced pressure. The residue was purified by column chromatography on silica gel (development system: hexane-ethyl acetate=1:2) to prepare 37 mg of the title compound.
Physicochemical Properties of Compound Prepared in Example 7
(1) Color and form: Colorless solid
(2) Molecular formula: $C_{29}H_{36}N_6O_5S$
(3) Mass spectrum (FABMS): m/z 581 (M+H)$^+$
(4) $^1$H NMR spectrum (400 MHz, CDCl$_3$) δ (ppm):1.29 (9H, s, t-Bu), 1.32 (3H, d, CH$_3$), 3.04 (1H, dt, piperazine), 3.24 (1H, dd, piperazine), 3.48 (1H, dt, piperazine), 3.57 (1H, m, CONHC$\underline{H}_2$CH), 3.66 (1H, dt, piperazine), 3.77 (1H, m, piperazine), 3.91 (2H, m, CONHC$\underline{H}_2$C$\underline{H}$), 4.54 (1H, dt, piperazine), 4.96 (1H, m, piperazine), 6.53 (1H, t, pyrimidine), 6.90 (2H, d, $C_6H_4$), 7.50 (2H, m, $C_6H_5$), 7.57 (1H, m, $C_6H_5$), 7.73 (2H, d, $C_6H_4$), 7.86 (2H, m, $C_6H_5$), 8.35 (2H, d, pyrimidine)

Example 8

(2S)-Benzenesulfonylamino-3-[4-{3-methyl-4-(pyrimidin-2-yl)-piperazin-1-yl}-benzoylamino]-propionic acid Methylene chloride (2.0 ml) was added to 17 mg of the compound prepared in Example 7 to prepare a solution, and 1.0 ml of trifluoroacetic acid was added at room temperature to the solution. The mixture was stirred at that temperature for 4 hr before the reaction solution was concentrated under the reduced pressure. The residue was purified by preparative thin-layer chromatography on silica gel (development system: methylene chloride-methanol-concentrated aqueous ammonia=800:200:1), and then purified by Sephadex LH-20 (development system: methanol) to prepare 4.6 mg of the title compound.

Physicochemical Properties of Compound Prepared in Example 8
(1) Color and form: Colorless solid
(2) Molecular formula: $C_{24}H_{28}N_6O_4S$
(3) Mass spectrum (FABMS): m/z 525 (M+H)$^+$
(4) $^1$H NMR spectrum (400 MHz, CD$_3$OD) δ (ppm): 1.21 (3H, d, CH$_3$), 2.88 (1H, dt, piperazine), 3.08 (1H, dd, piperazine), 3.36 (1H, ddd, piperazine), 3.47 (1H, dd, CONHC$\underline{H}_2$CH), 3.56 (1H, dd, CONHC$\underline{H}_2$CH), 3.63 (1H, dd, CONHCH$_2$C$\underline{H}$), 3.68 (1H, br d, piperazine), 3.76 (1H, br d, piperazine), 4.42 (1H, dt, piperazine), 4.83 (1H, m, piperazine), 6.51 (1H, t, pyrimidine), 6.89 (2H, d, $C_6H_4$), 7.37 (2H, m, $C_6H_5$), 7.43 (1H, m, $C_6H_5$), 7.63 (2H, d, $C_6H_4$), 7.76 (2H, m, $C_6H_5$), 8.25 (2H, d, pyrimidine)

Example 9

(2S)-Benzenesulfonylamino-3-[4-{3-methyl-4-(1,4,5,6-tetrahydropyrimidin-2-yl)-piperazin-1-yl}-benzoylamino]-propionic acid Acetic acid (10 ml) and 1.0 ml of concentrated hydrochloric acid were added to 11 mg of the compound prepared in Example 8 to prepare a solution, and 5.6 mg of 10% palladium-carbon was added to the solution, followed by vigorous stirring at room temperature for 4 hr under a hydrogen pressure of 3 atm. The insolubles were collected by filtration, and then washed twice with water. The filtrate was combined with the washings, followed by concentration under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 5.9 mg of the title compound.

Physicochemical Properties of Compound Prepared in Example 9
(1) Color and form: Colorless solid
(2) Molecular formula: $C_{25}H_{32}N_6O_4S$
(3) Mass spectrum (FABMS): m/z 529 (M+H)$^+$
(4) $^1$H NMR spectrum (400 MHz, CD$_3$OD) δ (ppm): 1.32 (3H, d, CH$_3$), 1.96 (2H, quintet, tetrahydropyrimidine), 2.97 (1H, br t, piperazine), 3.16 (1H, br d, piperazine), 3.41 (4H, br t, tetrahydropyrimidine), 3.46 (1H, br d, piperazine), 3.64 (5H, m, piperazine and CONHC$\underline{H}_2$C$\underline{H}$), 3.78 (1H, br d, piperazine), 4.09 (1H, m, piperazine), 6.72 (2H, d, $C_6H_4$), 7.47 (2H, m, $C_6H_5$), 7.54 (1H, m, $C_6H_5$), 7.72 (2H, d, $C_6H_4$), 7.85 (2H, m, $C_6H_5$)

Intermediate 10: Ethyl 4-{(3R)-methyl-(piperazin-1-yl)}-benzoate

Dimethyl sulfoxide (2.0 ml) was added to 295 mg of (2R)-methylpiperazine to prepare a suspension, and 419 mg of ethyl 4-fluorobenzoate was added to the suspension. The mixture was stirred at 120° C. for 6 hr and was then cooled to room temperature, and the reaction solution was concentrated under the reduced pressure. The residue was purified by column chromatography on silica gel (development system: methylene chloride-methanol-concentrated aqueous ammonia=900:100:1) to prepare 407 mg of the title compound.

Physicochemical Properties of Intermediate 10
(1) Color and form: pale yellow solid
(2) Molecular formula: $C_{14}H_{20}N_2O_2$
(3) Mass spectrum (FABMS): m/z 249 (M+H)$^+$
(4) $^1$H NMR spectrum (400 MHz, CD$_3$OD ) δ (ppm): 0.90 (3H, d, CH$_3$), 1.26 (3H, t, CH$_2$C$\underline{H}_3$), 2.36 (1H, m, piperazine), 2.70 (1H, m, piperazine), 2.81 (2H, m, piperazine), 2.98 (1H, m, piperazine), 3.66 (2H, m, piperazine), 4.20 (2H, q, C$\underline{H}_2$CH$_3$), 6.86 (2H, d, $C_6H_4$), 7.77 (2H, d, $C_6H_4$)

Intermediate 11: Ethyl 4-{(3R)-methyl-4-(pyrimidin-2-yl)-piperazin-1-yl}-benzoate Dimethylformamide (15 ml) was added to 407 mg of intermediate 10 to prepare a solution, and 231 mg of 2-bromopyrimidine was added to the solution. Diisopropylethylamine (1.5 ml) was added to the mixture, and the mixture was stirred at 120° C. for 25 hr and was then cooled to room temperature, followed by concentration under the reduced pressure. The residue was purified by column chromatography on silica gel (development system: hexane-ethyl acetate=1:2) to prepare 290 mg of the title compound.

Physicochemical Properties of Intermediate 11
(1) Color and form: pale yellow solid
(2) Molecular formula: $C_{18}H_{22}N_4O_2$
(3) Mass spectrum (TSPMS): m/z 327 (M+H)$^+$
(4) $^1$H NMR spectrum (400 MHz, CDCl$_3$) δ (ppm): 1.31 (3H, d, CH$_3$), 1.37 (3H, t, CH$_2$CH$_3$), 3.08 (1H, ddd, piperazine), 3.28 (1H, dd, piperazine), 3.50 (1H, ddd, piperazine), 3.68 (1H, dt, piperazine), 3.79 (1H, ddt, piperazine), 4.33 (2H, q, C$\underline{H}_2$CH$_3$), 4.52 (1H, dt, piperazine), 4.95 (1H, m, piperazine), 6.52 (1H, t, pyrimidine), 6.86 (2H, d, $C_6H_4$), 7.94 (2H, d, $C_6H_4$), 8.34 (2H, d, pyrimidine)

Intermediate 12: 4-{(3R)-Methyl-4-(pyrimidin-2-yl)-piperazin-1-yl}-benzoic acid Methanol (2.0 ml) and 8.0 ml of tetrahydrofuran were added to 116 mg of intermediate 11 to prepare a solution, and 8.0 ml of a 1 N aqueous sodium hydroxide solution was added to the solution. The mixture was stirred at 40° C. for 5 hr and was then cooled to room temperature. The system was adjusted to pH 6 to 8 by the addition of 1 N hydrochloric acid, followed by concentration under the reduced pressure.

The residue was purified by column chromatography on silica gel (development system: hexane-ethyl acetate=1:2) to prepare 52 mg of the title compound.

Physicochemical Properties of Intermediate 12

(1) Color and form: Colorless solid
(2) Molecular formula: $C_{16}H_{18}N_4O_2$
(3) Mass spectrum (EIMS): m/z 298
(4) $^1$H NMR spectrum (400 MHz, CDCl$_3$) δ (ppm): 1.31 (3H, d, CH$_3$), 3.14 (1H, ddd, piperazine), 3.34 (1H, dd, piperazine), 3.53 (1H, ddd, piperazine), 3.77 (1H, m, piperazine), 3.83 (1H, m, piperazine), 4.51 (1H, dt, piperazine), 4.95 (1H, m, piperazine), 6.54 (1H, t, pyrimidine), 6.88 (2H, d, C$_6$H$_4$), 8.00 (2H, d, C$_6$H$_4$), 8.36 (2H, d, pyrimidine)

Example 10 t-Butyl (2S)-benzenesulfonylamino-3-[4-{(3R)-methyl-4-(pyrimidin-2-yl)-piperazin-1-yl}-benzoylamino]-propionate Dimethylformamide (3.0 ml) was added to 50 mg of intermediate 12 to prepare a solution, and 54 mg of t-butyl (2S)-benzenesulfonyl-2,3-diaminopropionate was added to the solution. Further, 34 mg of 1-hydroxybenzotriazole, 0.15 ml of N-methylmorpholine, and 70 mg of 1-ethyl-3-(3-dimethylaminopropyl)carbodiimide hydrochloride were added to the mixture, and the mixture was stirred at room temperature for 20 hr. A saturated aqueous sodium hydrogencarbonate solution (30 ml) was added to the mixture to stop the reaction, and 30 ml of methylene chloride was added thereto. The organic layer was then separated, dried over anhydrous magnesium sulfate, and concentrated under the reduced pressure. The residue was purified by column chromatography on silica gel (development system: hexane-ethyl acetate=1:2) to prepare 85 mg of the title compound.

Physicochemical Properties of Compound Prepared in Example 10

(1) Color and form: Colorless solid
(2) Molecular formula: $C_{29}H_{36}N_6O_5S$
(3) Mass spectrum (FABMS): m/z 581 (M+H)$^+$
(4) $^1$H NMR spectrum (400 MHz, CDCl$_3$) δ (ppm): 1.28 (9H, s, t-Bu), 1.32 (3H, d, CH$_3$), 3.03 (1H, dt, piperazine), 3.23 (1H, dd, piperazine), 3.47 (1H, ddd, piperazine), 3.59 (1H, ddd, CONHC$\underline{H}_2$CH), 3.65 (1H, m, piperazine), 3.76 (1H, m, piperazine), 3.89 (1H, ddd, CONHC$\underline{H}_2$CH), 3.94 (1H, dt, CONHCH$_2$C$\underline{H}$), 4.54 (1H, dt, piperazine), 4.96 (1H, m, piperazine), 6.53 (1H, t, pyrimidine), 6.88 (1H, d, C$_6$H$_4$), 7.49 (2H, m, C$_6$H$_5$), 7.56 (1H, m, C$_6$H$_5$), 7.73 (2H, d, C$_6$H$_4$), 7.86 (2H, m, C$_6$H$_5$), 8.35 (2H, d, pyrimidine)

Example 11

(2S)-Benzenesulfonylamino-3-[4-{(3R)-methyl-4-(pyrimidin-2-yl)-piperazin-1-yl}-benzoylamino]-propionic acid Methylene chloride (4.0 ml) was added to 43 mg of the compound prepared in Example 10 to prepare a solution, and 2.0 ml of trifluoroacetic acid was added at room temperature to the solution. The mixture was stirred at that temperature for 4 hr before the reaction solution was concentrated under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 30 mg of the title compound.

Physicochemical Properties of Compound Prepared in Example 11

(1) Color and form: Colorless solid
(2) Molecular formula: $C_{24}H_{28}N_6O_4S$
(3) Mass spectrum (TSPMS): m/z 525 (M+H)$^+$
(4) Specific rotation: $[\alpha]_D^{25}$+55° (c 0.073, MeOH)
(5) $^1$H NMR spectrum (400 MHz, CD$_3$OD) δ (ppm): 1.21 (3H, d, CH$_3$), 2.88 (1H, dt, piperazine), 3.08 (1H, dd, piperazine), 3.36 (1H, ddd, piperazine), 3.47 (1H, dd, CONHC$\underline{H}_2$CH), 3.56 (1H, dd, CONHC$\underline{H}_2$CH), 3.63 (1H, dd, CONHCH$_2$C$\underline{H}$), 3.68 (1H, m, piperazine), 3.76 (1H, m, piperazine), 4.42 (1H, dt, piperazine), 4.79 (1H, m, piperazine), 6.51 (1H, t, pyrimidine), 6.89 (2H, d, C$_6$H$_4$), 7.35 (2H, m, C$_6$H$_5$), 7.43 (1H, m, C$_6$H$_5$), 7.63 (2H, d, C$_6$H$_4$), 7.76 (2H, m, C$_6$H$_5$), 8.25 (2H, d, pyrimidine)

Example 12

(2S)-Benzenesulfonylamino-3-[4-{(3R)-methyl-4-(1,4,5,6-tetrahydropyrimidin-2-yl)-piperazin-1-yl}-benzoylamino]-propionic acid Acetic acid (10 ml) and 1.0 ml of concentrated hydrochloric acid were added to 10 mg of the compound prepared in Example 11 to prepare a solution. 10% Palladium-carbon (5.6 mg) was added to the solution, and the mixture was vigorously shaken at room temperature for 4 hr under a hydrogen pressure of 3 atm. The insolubles were collected by filtration, and then washed twice with water. The filtrate was combined with the washings, followed by concentration under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 2.5 mg of the title compound.

Physicochemical Properties of Compound Prepared in Example 12

(1) Color and form: Colorless solid
(2) Molecular formula: $C_{25}H_{32}N_6O_4S$
(3) Mass spectrum (FABMS): m/z 529 (M+H)$^+$
(4) Specific rotation: $[\alpha]_D^{25}$ +81° (c 0.060, MeOH)$^+$
(5) $^1$H NMR spectrum (400 MHz, CD$_3$OD) δ (ppm): 1.34 (3H, d, CH$_3$), 1.96 (2H, quintet, tetrahydropyrimidine), 2.99 (1H, dt, piperazine), 3.18 (1H, dd, piperazine), 3.42 (4H, br t, tetrahydropyrimidine), 3.47 (1H, m, piperazine), 3.57 (1H, dd, CONHC$\underline{H}_2$CH), 3.60 (1H, m, piperazine), 3.65 (1H, dd, CONHC$\underline{H}_2$CH), 3.71 (1H, dd, CONHCH$_2$C$\underline{H}$), 3.73 (1H, m, piperazine), 3.80 (1H, m, piperazine), 4.09 (1H, m, piperazine), 6.95 (2H, d, C$_6$H$_4$), 7.48 (2H, m, C$_6$H$_5$), 7.55 (1H, m, C$_6$H$_5$), 7.74 (2H, d, C$_6$H$_4$), 7.86 (2H, m, C$_6$H$_5$)

Intermediate 13

Ethyl 4-{(3S)-methyl-(piperazin-1-yl)}-benzoate

Dimethyl sulfoxide (2.0 ml) was added to 307 mg of (2S)-methylpiperazine to prepare a suspension, and 526 mg of ethyl 4-fluorobenzoate was added to the suspension. The mixture was stirred at 120° C. for 21 hr and was then cooled to room temperature. The reaction solution was concentrated under the reduced pressure. The residue was purified by column chromatography on silica gel (development system: methylene chloride-methanol-concentrated aqueous ammonia=1900:100:1) to prepare 449 mg of the title compound.

Physicochemical Properties of Intermediate 13
(1) Color and form: pale yellow solid
(2) Molecular formula: $C_{14}H_{20}N_2O_2$ Intermediate 14: Ethyl 4-{(3S)-methyl-4-(pyrimidin-2-yl)-piperazin-1-yl}-benzoate Dimethylformamide (10 ml) was added to 449 mg of intermediate 13 to prepare a solution, and 476 mg of 2-bromopyrimidine was added to the solution. Diisopropylethylamine (1.5 ml) was added to the mixture. The mixture was stirred at 120° C. for 10 hr and was then cooled to room temperature, followed by concentration under the reduced pressure. The residue was purified by column chromatography on silica gel (development system: hexane-ethyl acetate=1:2) to prepare 331 mg of the title compound.

Physicochemical Properties of Intermediate 14
(1) Color and form: pale yellow solid
(2) Molecular formula: $C_{18}H_{22}N_4O_2$
(3) Mass spectrum (FABMS): m/z 327 (M+H)$^+$
(4) $^1$H NMR spectrum (400 MHz, CDCl$_3$) δ (ppm): 1.31 (3H, d, CH$_3$), 1.37 (3H, t, CH$_2$C$\underline{H}_3$), 3.08 (1H, ddd, piperazine), 3.28 (1H, dd, piperazine), 3.50 (1H, ddd, piperazine), 3.68 (1H, dt, piperazine), 3.79 (1H, ddt, piperazine), 4.33 (2H, q, C$\underline{H}_2$CH$_3$), 4.52 (1H, dt, piperazine), 4.95 (1H, m, piperazine), 6.52 (1H, t, pyrimidine), 6.86 (2H, d, C$_6$H$_4$), 7.94 (2H, d, C$_6$H$_4$), 8.34 (2H, d, pyrimidine)

Intermediate 15: 4-{(3S)-Methyl-4-(pyrimidin-2-yl)-piperazin-1-yl}-benzoic acid

Methanol (2.0 ml) and 8.0 ml of tetrahydrofuran were added to 209 mg of intermediate 14 to prepare a solution, and 8.0 ml of a 1 N aqueous sodium hydroxide solution was added to the solution. The mixture was stirred at 40° C. for 27 hr and was then cooled to room temperature. The system was adjusted to pH 6 to 8 by the addition of 1 N hydrochloric acid, followed by concentration under the reduced pressure. The residue was purified by column chromatography on silica gel (development system: methylene chloride-ethanol-water-concentrated aqueous ammonia=8:8:1:1) to prepare 155 mg of the title compound.

Physicochemical Properties of Intermediate 15
(1) Color and form: Colorless solid
(2) Molecular formula: $C_{16}H_{18}N_4O_2$
(3) Mass spectrum (TSPMS): m/z 299 (M+H)$^+$
(4) $^1$H NMR spectrum (400 MHz, CD$_3$OD) δ (ppm): 1.19 (3H, d, CH$_3$), 2.92 (1H, ddd, piperazine), 3.12 (1H, dd, piperazine), 3.37 (1H, ddd, piperazine), 3.71 (1H, dt, piperazine), 3.78 (1H, ddt, piperazine), 4.40 (1H, dt, piperazine), 4.81 (1H, m, piperazine), 6.51 (1H, t, pyrimidine), 6.86 (2H, d, C$_6$H$_4$), 7.79 (2H, d, C$_6$H$_4$), 8.25 (2H, d, pyrimidine)

Example 13 t-Butyl (2S)-benzenesulfonylamino-3-[4-{(3S)-methyl-4-(pyrimidin-2-yl)-piperazin-1-yl}-benzoylamino]-propionate Dimethylformamide (2.0 ml) was added to 50 mg of intermediate 15 to prepare a solution, and 54 mg of t-butyl (2S)-benzenesulfonyl-2,3-diaminopropionate was added to the solution. Further, 34 mg of 1-hydroxybenzotriazole, 0.18 ml of N-methylmorpholine, and 65 mg of 1-ethyl-3-(3-dimethylaminopropyl)carbodiimide hydrochloride were added to the mixture. The mixture was stirred at room temperature for 5.5 hr. A saturated aqueous sodium hydrogencarbonate solution (20 ml) was added to the mixture to stop the reaction, and 20 ml of methylene chloride was added thereto. The organic layer was then separated, dried over anhydrous magnesium sulfate, and concentrated under the reduced pressure. The residue was purified by column chromatography on silica gel (development system: hexane-ethyl acetate=1:2) to prepare 98 mg of the title compound.

Physicochemical Properties of Compound Prepared in Example 13
(1) Color and form: Colorless solid
(2) Molecular formula: $C_{29}H_{36}N_6O_5S$
(3) Mass spectrum (APCIMS): m/z 581 (M+H)$^+$
(4) $^1$H NMR spectrum (400 MHz, CDCl$_3$) δ (ppm): 1.28 (9H, s, t-Bu), 1.33 (3H, d, CH$_3$), 3.04 (1H, dt, piperazine), 3.23 (1H, dd, piperazine), 3.47 (1H, dd, piperazine), 3.58 (1H, ddd, CONHC$\underline{H}_2$CH), 3.66 (1H, br d, piperazine), 3.77 (1H, br d, piperazine), 3.91 (2H, m, CONHC$\underline{H}_2$C$\underline{H}$), 4.53 (1H, dt, piperazine), 4.96 (1H, m, piperazine), 6.53 (1H, t, pyrimidine), 6.89 (2H, d, C$_6$H$_4$), 7.49 (2H, t, C$_6$H$_5$), 7.57 (1H, t, C$_6$H$_5$), 7.73 (2H, d, C$_6$H$_4$), 7.86 (2H, br d, C$_6$H$_5$), 8.35 (2H, d, pyrimidine)

Example 14

(2S)-Benzenesulfonylamino-3-[4-{(3S)-methyl-4-(pyrimidin-2-yl)-piperazin-1-yl}-benzoylamino]-propionic acid Methylene chloride (6.0 ml) was added to 98 mg of the compound prepared in Example 13 to prepare a solution, and 2.0 ml of trifluoroacetic acid was added at room temperature to the solution. The mixture was stirred at that temperature for 4.5 hr before the reaction solution was concentrated under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 39 mg of the title compound.

Physicochemical Properties of Compound Prepared in Example 14
(1) Color and form: Colorless solid
(2) Molecular formula: $C_{24}H_{28}N_6O_4S$
(3) Mass spectrum (TSPMS): m/z 525 (M+H)$^+$
(4) Specific rotation: $[\alpha]_D^{25}$ +36° (c 0.073, MeOH)
(5) $^1$H NMR spectrum (400 MHz, CD$_3$OD) δ (ppm): 1.21 (3H, d, CH$_3$), 2.89 (1H, dt, piperazine), 3.08 (1H, dd, piperazine), 3.38 (2H, m, piperazine and CONHC$\underline{H}_2$CH), 3.59 (1H, dd, CONHC$\underline{H}_2$CH), 3.68 (1H, br d, CONHCH$_2$C$\underline{H}$), 3.76 (1H, br d, piperazine), 3.95 (1H, m, piperazine), 4.41 (1H, dt, piperazine), 4.82 (1H, m, piperazine), 6.51 (1H, t, pyrimidine), 6.87 (2H, d, C$_6$H$_4$), 7.33 (2H, t, C$_6$H$_5$), 7.40 (1H, t, C$_6$H$_5$), 7.58 (2H, d, C$_6$H$_4$), 7.74 (2H, d, C$_6$H$_5$), 8.25 (2H, d, pyrimidine)

Example 15

(2S)-Benzenesulfonylamino-3-[4-{(3S)-methyl-4-(1,4,5,6-tetrahydropyrimidin-2-yl)-piperazin-1-yl}-benzoylamino]-propionic acid Acetic acid (7.0 ml) and 0.70 ml of concentrated hydrochloric acid were added to 6.9 mg of the compound prepared in Example 14 to prepare a solution. 10% Palladium-carbon (3.5 mg) was added to the solution, and the mixture was vigorously shaken at room temperature for 4 hr under a hydrogen pressure of 3 atm. The insolubles were collected by filtration, and then washed twice with water. The filtrate was combined with the washings, followed by concentration under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 2.2 mg of the title compound.

Physicochemical Properties of Compound Prepared in Example 15

(1) Color and form: Colorless solid
(2) Molecular formula: $C_{25}H_{32}N_6O_4S$
(3) Mass spectrum (FABMS): m/z 529 (M+H)$^+$
(4) Specific rotation: $[\alpha]_D^{25}$ +96° (c 0.085, MeOH)
(5) $^1$H NMR spectrum (400 MHz, CD$_3$OD) δ (ppm): 1.33 (3H, d, CH$_3$), 1.96 (2H, quintet, tetrahydropyrimidine), 2.97 (1H, ddd, piperazine), 3.16 (1H, dd, piperazine), 3.42 (4H, br t, tetrahydropyrimidine), 3.45 (1H, m, piperazine), 3.58 (1H, dd, CONHC$\underline{H}_2$CH), 3.59 (1H, m, piperazine), 3.65 (1H, dd, CONHC$\underline{H}_2$CH), 3.70 (1H, m, piperazine), 3.72 (1H, dd, CONHCH$_2$C$\underline{H}$), 3.79 (1H, m, piperazine), 4.09 (1H, m, piperazine), 6.93 (2H, d, C$_6$H$_4$), 7.48 (2H, m, C$_6$H$_5$), 7.55 (1H, m, C$_6$H$_5$), 7.73 (2H, d, C$_6$H$_4$), 7.86 (2H, m, C$_6$H$_5$)

Intermediate 16: Ethyl 4-{4-(1H-benzimidazol-2-yl)-piperazin-1-yl}-benzoate

Dimethylformamide (2.0 ml) was added to 93 mg of intermediate 1 to prepare a solution, and 37 mg of 2-chlorobenzimidazole was added to the solution. The mixture was stirred at 140° C. for 28 hr and was then cooled to room temperature, and 20 ml of water and 20 ml of methylene chloride were added thereto. The organic layer was separated, dried over anhydrous magnesium sulfate, and concentrated under the reduced pressure. The residue was purified by column chromatography on silica gel (development system: hexane-ethyl acetate=1:2) to prepare 37 mg of the title compound.

Physicochemical Properties of Intermediate 16

(1) Color and form: Colorless solid
(2) Molecular formula: $C_{20}H_{22}N_4O_2$
(3) Mass spectrum (TSPMS): m/z 351 (M+H)$^+$
(4) $^1$H NMR spectrum (400 MHz, CDCl$_3$) δ (ppm): 1.38 (3H, t, CH$_2$C$\underline{H}_3$), 3.44 (4H, m, piperazine), 3.73 (4H, m, piperazine), 4.34 (2H, q, C$\underline{H}_2$CH$_3$), 6.88 (2H, br d, C$_6$H$_4$), 7.09 (2H, dd, benzimidazole), 7.34 (2H, m, benzimidazole), 7.95 (2H, br d, C$_6$H$_4$)

Intermediate 17: 4-{4-(1H-Benzimidazol-2-yl)-piperazin-1-yl}-benzoic acid

Methanol (0.50 ml) and 2.0 ml of tetrahydrofuran were added to 24 mg of intermediate 16 to prepare a solution, and 2.0 ml of a 1 N aqueous sodium hydroxide solution was added to the solution. The mixture was stirred at 50° C. for 3.0 hr and was then cooled to room temperature. The system was adjusted to pH 6 to 8 by the addition of 1 N hydrochloric acid, and concentrated under the reduced pressure. The residue was purified by column chromatography on silica gel (development system: hexane-ethyl acetate-methanol=2:4:1) to prepare 20 mg of the title compound.

Physicochemical Properties of Intermediate 17

(1) Color and form: Colorless solid
(2) Molecular formula: $C_{18}H_{18}N_4O_2$
(3) Mass spectrum (TSPMS): m/z 323 (M+H)$^+$
(4) $^1$H NMR spectrum (400 MHz, CD$_3$OD) δ (ppm): 3.38 (4H, m, piperazine), 3.60 (4H, m, piperazine), 6.93 (4H, m, benzimidazole and C$_6$H$_4$), 7.17 (2H, dd, benzimidazole), 7.80 (2H, d, C$_6$H$_4$)

Example 16 t-Butyl (2S)-benzenesulfonylamino-3-[4-{4-(1H-benzimidazol-2-yl)-piperazin-1-yl}-benzoylamino]-propionate Dimethylformamide (1.0 ml) was added to 14 mg of intermediate 17 to prepare a solution, and 14 mg of t-butyl (2S)-benzenesulfonyl-2,3-diaminopropionate was added to the solution. Further, 9.5 mg of 1-hydroxybenzotriazole, 0.10 ml of N-methylmorpholine, and 18 mg of 1-ethyl-3-(3-dimethylaminopropyl)carbodiimide hydrochloride were added to the mixture, and the mixture was stirred at room temperature for 7 hr. A saturated aqueous sodium hydrogencarbonate solution (10 ml) was added to the mixture to stop the reaction, and 10 ml of methylene chloride was added thereto. The organic layer was then separated, dried over anhydrous magnesium sulfate, and concentrated under the reduced pressure. The residue was purified by column chromatography on silica gel (development system: methylene chloride-methanol-concentrated aqueous ammonia= 900:100:1) to prepare 25 mg of the title compound.

Physicochemical Properties of Compound Prepared in Example 16

(1) Color and form: Colorless solid
(2) Molecular formula: $C_{31}H_{36}N_6O_5S$
(3) Mass spectrum (FABMS): m/z 605 (M+H)$^+$
(4) $^1$H NMR spectrum (400 MHz, CDCl$_3$) δ (ppm): 1.21 (9H, s, t-Bu), 3.21 (4H, m, piperazine), 3.50 (1H, m, CONHC$\underline{H}_2$CH), 3.64 (4H, m, piperazine), 3.86 (2H, m, CONHC$\underline{H}_2$C$\underline{H}$), 6.82 (2H, d, C$_6$H$_4$), 7.03 (2H, dd, benzimidazole), 7.30 (2H, m, benzimidazole), 7.42 (2H, m, C$_6$H$_5$), 7.50 (1H, m, C$_6$H$_5$), 7.66 (2H, d, C$_6$H$_4$), 7.77 (2H, d, C$_6$H$_5$)

Example 17

(2S)-Benzenesulfonylamino-3-[4-{4-(1H-benzimidazol-2-yl)-piperazin-1-yl}-benzoylamino]-propionic acid Methylene chloride (2.0 ml) was added to 10 mg of the compound prepared in Example 16 to prepare a solution. Trifluoroacetic acid (0.20 ml) was added at room temperature to the solution, and the mixture was stirred at that temperature for 8 hr before the reaction solution was concentrated under the reduced pressure. The residue was purified by preparative thin-layer chromatography on silica gel (development system: ethanol-water-concentrated aqueous ammonia=8:1:1), and then purified by Sephadex LH-20 (development system: methanol-concentrated aqueous ammonia=9:1) to prepare 4.5 mg of the title compound.

Physicochemical Properties of Compound Prepared in Example 17

(1) Color and form: Colorless solid
(2) Molecular formula: $C_{27}H_{28}N_6O_4S$
(3) Mass spectrum (TSPMS): m/z 549 (M+H)$^+$
(4) Specific rotation: $[\alpha]_D^{25}$ +89° (c 0.068, MeOH)

(5) $^1$H NMR spectrum (400 MHz, CD$_3$OD) δ(ppm): 3.21 (4H, m, piperazine), 3.47 (1H, dd, CONHC$\underline{H}_2$CH), 3.57 (1H, dd, CONHC$\underline{H}_2$CH), 3.60 (4H, m, piperazine), 3.64 (1H, dd, CONHCH$_2$C$\underline{H}$), 6.92 (2H, dd, benzimidazole), 6.96 (2H, d, C$_6$H$_4$), 7.17 (2H, dd, benzimidazole), 7.37 (2H, m, C$_6$H$_5$), 7.43 (1H, br t, C$_6$H$_5$), 7.65 (2H, d, C$_6$H$_4$), 7.76 (2H, m, C$_6$H$_5$)

Example 18

Ethyl (3S)-[4-{4-(pyrimidin-2-yl)-piperazin-1-yl}-benzoylamino]-pent-4-ynate

Dimethylformamide (3.0 ml) was added to 24 mg of intermediate 3 to prepare a solution, and 21 mg of ethyl (3S)-ethynyl-3-aminopropionate hydrochloride was added to the solution. Further, 23 mg of 1-hydroxybenzotriazole, 0.060 ml of N-methylmorpholine, and 33 mg of 1-ethyl-3-(3-dimethylaminopropyl)carbodiimide hydrochloride were added to the mixture, and the mixture was stirred at room temperature for 23 hr. A saturated aqueous sodium hydrogencarbonate solution (30 ml) was added to the mixture to stop the reaction, and 30 ml of methylene chloride was added thereto. The organic layer was then separated, dried over anhydrous magnesium sulfate, and concentrated under the reduced pressure. The residue was purified by column chromatography on silica gel (development system: hexane-ethyl acetate=3:7) to prepare 19 mg of the title compound.
Physicochemical Properties of Compound Prepared in Example 18
(1) Color and form: Colorless solid
(2) Molecular formula: C$_{22}$H$_{25}$N$_5$O$_3$
(3) Mass spectrum (TSPMS): m/z 408 (M+H)$^+$
(4) $^1$H NMR spectrum (400 MHz, CDCl$_3$) δ (ppm): 1.29 (3H, t, CH$_2$C$\underline{H}_3$), 2.30 (1H, d, C (triple bond) CH), 2.78 (1H, dd, CONHCHC$\underline{H}_2$), 2.86 (1H, dd, CONHCHC$\underline{H}_2$), 3.39 (4H, m, piperazine), 3.99 (4H, m, piperazine), 4.22 (2H, q, C$\underline{H}_2$CH$_3$), 5.32 (1H, m, CONHC$\underline{H}$CH$_2$), 6.54 (1H, t, pyrimidine), 6.94 (2H, d, C$_6$H$_4$), 7.73 (2H, d, C$_6$H$_4$), 8.34 (2H, d, pyrimidine)

Example 19

(3S)-[4-{4-(Pyrimidin-2-yl)-piperazin-1-yl}-benzoylamino]-pent-4-ynic acid

Methanol (0.50 ml) and 3.0 ml of tetrahydrofuran were added to 10 mg of the compound prepared in Example 18 to prepare a solution, and 3.0 ml of a 1 N aqueous sodium hydroxide solution was added to the solution. The mixture was stirred at 40° C. for 5 hr and was then cooled to room temperature. The system was adjusted to pH 6 to 8 by the addition of 1 N hydrochloric acid, and concentrated under the reduced pressure. The residue was purified by Sephadex LH-20 (development system: water) to prepare 4.5 mg of the title compound.
Physicochemical Properties of Compound Prepared in Example 19
(1) Color and form: Colorless solid
(2) Molecular formula: C$_{20}$H$_{21}$N$_5$O$_3$
(3) Mass spectrum (TSPMS): m/z 380 (M+H)$^+$
(4) Specific rotation:[α]$_D^{25}$ +24° (c 0.051, MeOH)
(5) $^1$H NMR spectrum (400 MHz, CD$_3$OD) δ (ppm): 2.44 (1H, d, C (triple bond) CH), 2.51 (1H, d, CONHCHC$\underline{H}_2$), 2.53 (1H, d, CONHCHC$\underline{H}_2$), 3.31 (4H, m, piperazine), 3.86 (4H, m, piperazine), 5.02 (1H, dt, CONHC$\underline{H}$CH$_2$), 6.51 (1H, t, pyrimidine), 6.92 (2H, d, C$_6$H$_4$), 7.66 (2H, d, C$_6$H$_4$), 8.25 (2H, d, pyrimidine)

Example 20 t-Butyl (2S)-benzenesulfonylamino-3-[4-{4-(pyrimidin-2-yl)-piperazin-1-yl}-benzylamino]-propionate Intermediate 2 (200 ml) was dissolved in 5.6 ml of methylene chloride, and 1.6 ml of a 1 M toluene solution of diisobutyl aluminum hydride was added dropwise to the solution under cooling at −78° C. over a period of 10 min. A reaction was allowed to proceed at that temperature for one hr. Methanol (0.8 ml) was added thereto at that temperature, and was then heated to room temperature. Methylene chloride (50 ml) and 50 ml of a saturated aqueous Rochelle salt solution were added thereto, followed by vigorous stirring at room temperature for 15 min. The organic layer was separated, washed twice with 50 ml of saturated saline, dried over anhydrous sodium sulfate, and then concentrated under the reduced pressure to prepare 158 mg of 4-[4-(pyrimidin-2-yl)-piperazin-1-yl]-benzyl alcohol. This compound (143 mg) was dissolved in 14 ml of ethyl acetate, and 358 mg of active manganese dioxide was added to the solution. The mixture was vigorously stirred at room temperature for 2 hr. The insolubles were collected by filtration, and then washed twice with methanol. The filtrate was combined with the washings, followed by concentration under the reduced pressure to prepare 142 mg of 4-[4-(pyrimidin-2-yl)-piperazin-1-yl]-benzaldehyde. 75% Methanol/methylene chloride (14 ml) was added to this compound and 318 mg of t-butyl (2S)-benzenesulfonyl-2,3-diaminopropionate to dissolve them in the methanol/methylene chloride. The reaction solution was adjusted to pH 3 to 4 by the addition of a minor amount of acetic acid. Sodium boron cyanohydride (150 mg) was added thereto, followed by a reaction at room temperature for 30 min. The reaction solution was concentrated under the reduced pressure. The residue was purified by column chromatography on silica gel (development system: chloroform-methanol-concentrated aqueous ammonia=1000:30:1) to prepare 288 mg of the title compound.
Physicochemical Properties of Compound Prepared in Example 20
(1) Color and form: Colorless solid
(2) Molecular formula: C$_{28}$H$_{36}$N$_6$O$_4$S
(3) Mass spectrum (TSPMS): m/z 553 (M+H)$^+$
(4) Specific rotation: [α]$_D^{25}$ +14° (cl.0, CHCl$_3$)
(5) $^1$H NMR spectrum (400 MHz, CDCl$_3$) δ (ppm): 1.26 (9H, s, t-Bu), 2.85 (1H, dd, ArCH$_2$NHC$\underline{H}_2$), 2.91 (1H, dd, ArCH$_2$NHC$\underline{H}_2$), 3.24 (4H, m, piperazine), 3.61 (1H, d, ArC$\underline{H}_2$), 3.73 (1H, d, ArC$\underline{H}_2$), 3.94 (1H, dd, PhSO$_2$NHC$\underline{H}$), 3.98 (4H, m, piperazine), 6.52 (1H, t, pyrimidine), 6.93 (2H, d, C$_6$H$_4$), 7.19 (2H, d, C$_6$H$_4$), 7.49 (2H, m, SO$_2$C$_6$H$_5$), 7.56 (1H, m, SO$_2$C$_6$H$_5$), 7.86 (2H, m, SO$_2$C$_6$H$_5$), 8.34 (2H, d, pyrimidine)

Example 21

(2S)-Benzenesulfonylamino-3-[4-{4-(pyrimidin-2-yl)-piperazin-1-yl}-benzylamino]-propionic acid Methylene chloride (6.0 ml) was added to 269 mg of the compound prepared in Example 20 to prepare a solution, and 0.26 ml of anisole was added to the solution. The mixture was cooled to 0° C. Trifluoroacetic acid (6.0 ml) was added at that temperature to the mixture, and a reaction was allowed to proceed at room temperature for 16 hr. The reaction solution was concentrated under the reduced pressure. The residue was subjected to azeotropic distillation twice with toluene, followed by purification by column chromatography on silica gel (development system: chloroform-methanol-concentrated aqueous ammonia= 90:20:1) to prepare 224 mg of the title compound.

Physicochemical Properties of Compound Prepared in Example 21

(1) Color and form: Colorless solid
(2) Molecular formula: $C_{24}H_{28}N_6O_4S$
(3) Mass spectrum (TSPMS (neg.)): m/z 495 (M–H)⁻
(4) Specific rotation: $[\alpha]_D^{25}$ +99° (c0.4, $CHCl_3$—MeOH (1:1))
(5) ¹H NMR spectrum (400 MHz, $CDCl_3$—$CD_3OD$(1:1)) δ (ppm): 3.18 (1H, dd, ArCH₂NHC$\underline{H}_2$), 3.28 (1H, dd, ArCH₂NHC$\underline{H}_2$), 3.33 (4H, m, piperazine), 3.58 (1H, dd, PhSO₂NHC$\underline{H}$), 3.98 (4H, m, piperazine), 4.08 (2H, ABq, ArC$\underline{H}_2$), 6.62 (1H, t, pyrimidine), 7.02 (2H, d, $C_6H_4$), 7.34 (2H, d, $C_6H_4$), 7.54 (2H, m, $SO_2C_6H_5$), 7.62 (1H, m, $SO_2C_6H_5$), 7.88 (2H, m, $SO_2C_6H_5$), 8.35 (2H, d, pyrimidine)

Example 22

(2S)-Benzenesulfonylamino-3-{4-[4-(1,4,5,6-tetrahydropyrimidin-2-yl)-piperazin-1-yl]-benzylamino}-propionic acid Acetic acid (2.0 ml) and 0.30 ml of concentrated hydrochloric acid were added to 44 mg of the compound prepared in Example 21 to prepare a solution. 10% Palladium-carbon (30 mg) was added to the solution, and the mixture was vigorously shaken at room temperature for 3 hr under a hydrogen pressure of 3 atm. The insolubles were collected by filtration, and then washed twice with acetic acid. The filtrate was combined with the washings, followed by concentration under the reduced pressure. The residue was subjected to azeotropic distillation twice with toluene, and then purified by preparative thin-layer chromatography on silica gel (development system: chloroform-methanol-concentrated aqueous ammonia=30:10:1) and then purified by Sephadex LH-20 (development system: methanol) to prepare 27 mg of the title compound.

Physicochemical Properties of Compound Prepared in Example 22

(1) Color and form: Colorless solid
(2) Molecular formula: $C_{24}H_{32}N_6O_4S$
(3) Mass spectrum (TSPMS): m/z 501 (M+H)⁺
(4) Specific rotation: $[\alpha]_D^{25}$ +74° (c1.0, MeOH)
(5) ¹H NMR spectrum (400 MHz, $CD_3OD$) δ (ppm): 1.90 (2H, quintet, tetrahydropyrimidine), 2.97 (2H, m, ArCH₂NHC$\underline{H}_2$), 3.21 (4H, m, piperazine), 3.34 (4H, t, tetrahydropyrimidine), 3.46 (4H, m, piperazine), 3.60 (1H, dd, PhSO₂NHC$\underline{H}$), 3.86 (2H, ABq, ArC$\underline{H}_2$), 6.92 (2H, d, $C_6H_4$), 7.26 (2H, d, $C_6H_4$), 7.47 (2H, m, $SO_2C_6H_5$), 7.54 (1H, m, $SO_2C_6H_5$), 7.82 (2H, m, $SO_2C_6H_5$)

Example 23

(2S)-Benzenesulfonylamino-3-[methyl-[4-{4-(pyrimidin-2-yl)-piperazin-1-yl}-benzyl]-amino]-propionic acid 50% methanol/methylene chloride (12 ml) was added to 80 mg of the compound prepared in Example 21 to prepare a solution. A 37% aqueous formalin solution (131 mg) was added to the solution, and the reaction solution was then adjusted to pH 3 to 4 by the addition of a minor amount of acetic acid. Sodium boron cyanohydride (60 mg) was added thereto, and a reaction was allowed to proceed at room temperature for 30 min. The reaction solution was concentrated under the reduced pressure. The residue was purified by preparative thin-layer chromatography on silica gel (development system: chloroform-methanol-concentrated aqueous ammonia=90:15:1) to prepare 66 mg of the title compound.

Physicochemical Properties of Compound Prepared in Example 23

(1) Color and form: Colorless solid
(2) Molecular formula: $C_{25}H_{30}N_6O_4S$
(3) Mass spectrum (TSPMS): m/z 511 (M+H)⁺
(4) Specific rotation: $[\alpha]_D^{25}$+77° (c0.8, $CHCl_3$)
(5) ¹H NMR spectrum (400 MHz, $CDCl_3$-$CD_3OD$(1:1)) δ (ppm): 2.70 (3H, s, NMe), 3.22 (1H, dd, ArCH₂NMeC$\underline{H}_2$), 3.34 (4H, m, piperazine), 3.64 (1H, dd, PhSO₂NHC$\underline{H}$), 3.98 (4H, m, piperazine), 4.13 (2H, ABq, ArC$\underline{H}_2$), 6.62 (1H, t, pyrimidine), 7.02 (2H, d, $C_6H_4$), 7.34 (2H, d, $C_6H_4$), 7.55 (2H, m, $SO_2C_6H_5$), 7.62 (1H, m, $SO_2C_6H_5$), 7.89 (2H, m, $SO_2C_6H_5$), 8.35 (2H, d, pyrimidine)

Example 24

(2S)-Benzenesulfonylamino-3-[methyl-[4-{4-(1,4,5,6-tetrahydropyrimidin-2-yl)-piperazin-1-yl}-benzyl]-amino]-propionic Acid Acetic acid (4.0 ml) and 0.60 ml of concentrated hydrochloric acid were added to 84 mg of the compound prepared in Example 23 to prepare a solution. 10% Palladium-carbon (60 mg) was added to the solution, and the mixture was vigorously shaken at room temperature for 3 hr under a hydrogen pressure of 3 atm. The insolubles were collected by filtration, and then washed twice with acetic acid. The filtrate was combined with the washings, followed by concentration under the reduced pressure. The residue was subjected to azeotropic distillation twice with toluene, and purified by preparative thin-layer chromatography on silica gel (development system: chloroform-methanol-concentrated aqueous ammonia=30:10:1) and then purified by Sephadex LH-20 (development system: methanol) to prepare 33 mg of the title compound.

Physicochemical Properties of Compound Prepared in Example 24

(1) Color and form: Colorless solid
(2) Molecular formula: $C_{25}H_{34}N_6O_4S$
(3) Mass spectrum (TSPMS): m/z 515 (M+H)⁺
(4) Specific rotation: $[\alpha]_D^{25}$+27° (c1.0, MeOH)
(5) ¹H NMR spectrum (400 MHz, $CD_3OD$) δ (ppm): 1.90 (2H, quintet, tetrahydropyrimidine), 2.21 (3H, s, NMe), 2.76 (2H, m, ArCH₂NMeC$\underline{H}_2$), 3.19 (4H, m, piperazine), 3.35 (4H, t, tetrahydropyrimidine), 3.48 (4H, m, piperazine), 3.56 (1H, br d, ArC$\underline{H}_2$), 3.66 (1H, br d, ArC$\underline{H}_2$), 3.70 (1H, dd, PhSO₂NHC$\underline{H}$), 6.88 (2H, d, $C_6H_4$), 7.20 (2H, d, $C_6H_4$), 7.46 (2H, m, $SO_2C_6H_5$), 7.53 (1H, m, $SO_2C_6H_5$), 7.83 (2H, m, $SO_2C_6H_5$)

Example 25

(2S)-Benzenesulfonylamino-3-[benzyl-[4-{4-(pyrimidin-2-yl)-piperazin-1-yl}-benzyl]-amino]-propionic Acid 50% Methanol/methylene chloride (1.5 ml) was added to 10 mg of the compound prepared in Example 21 to prepare a solution. Benzaldehyde (10.7 mg) was added to the solution, and the mixture was stirred at room temperature for 30 min. The reaction solution was adjusted to pH 3 to 4 by the addition of a minor amount of acetic acid. Sodium boron cyanohydride (3.8 mg) was then added thereto, and a reaction was allowed to proceed at room temperature for one hr. Further, 5.4 mg of benzaldehyde was added, and the reaction solution was adjusted to pH 3 to 4 by the addition of acetic acid. Sodium boron cyanohydride (1.9 mg) was added thereto, and a reaction was allowed to proceed at room temperature for 30 min. The reaction solution was concentrated under the reduced pressure. The residue was purified by preparative thin-layer chromatography on silica gel (development system: methylene chloride-ethyl acetate-methanol=12:1:1) to prepare 8.3 mg of the title compound.

Physicochemical Properties of Compound Prepared in Example 25

(1) Color and form: Colorless solid
(2) Molecular formula: $C_{31}H_{34}N_6O_4S$
(3) Mass spectrum (FABMS (+NaI)): m/z 609 (M+Na)$^+$
(4) Specific rotation: $[\alpha]_D^{25}$+118° (c0.8, CHCl$_3$)
(5) $^1$H NMR spectrum (400 MHz, CDCl$_3$) δ (ppm): 3.12 (1H, dd, ArCH$_2$NBzlC$\underline{H}_2$), 3.27 (1H, dd, ArCH$_2$NBzlC$\underline{H}_2$), 3.32 (4H, m, piperazine), 3.52 (1H, dd, PhSO$_2$NHC$\underline{H}$), 3.87 (1H, d, ArC$\underline{H}_2$), 3.92 (1H, d, ArC$\underline{H}_2$), 3.99 (1H, d, ArC$\underline{H}_2$), 3.99 (4H, m, piperazine), 4.03 (1H, d, ArC$\underline{H}_2$), 6.54 (1H, t, pyrimidine), 6.96 (2H, d, C$_6$H$_4$), 7.27 (2H, d, C$_6$H$_4$), 7.40 (5H, m, C$_6$H$_5$CH$_2$N), 7.48 (2H, br t, SO$_2$C$_6$H$_5$), 7.55 (1H, br t, SO$_2$C$_6$H$_5$), 7.77 (2H, br d, SO$_2$C$_6$H$_5$), 8.35 (2H, d, pyrimidine)

Example 26

(2S)-Benzenesulfonylamino-3-[benzyl-[4-{4-(1,4,5,6-tetrahydropyrimidin-2-yl)-piperazin-1-yl}-benzyl]-amino]-propionic Acid 50% Methanol/methylene chloride (1.5 ml) was added to 15 mg of the compound prepared in Example 22 to prepare a solution. Benzaldehyde (10 mg) was added to the solution, and the reaction solution was adjusted to pH 3 to 4 by the addition of a minor amount of acetic acid. Sodium boron cyanohydride (5.0 mg) was then added thereto, and a reaction was allowed to proceed at room temperature for 2 hr. The reaction solution was concentrated under the reduced pressure. The residue was purified by preparative thin-layer chromatography on silica gel (development system: chloroform-methanol-concentrated aqueous ammonia=30:10:1) and then purified by Sephadex LH-20 (development system: methanol) to prepare 5.1 mg of the title compound.

Physicochemical Properties of Compound Prepared in Example 26

(1) Color and form: Colorless solid
(2) Molecular formula: $C_{31}H_{38}N_6O_4S$
(3) Mass spectrum (FABMS): m/z 591 (M+H)$^+$
(4) Specific rotation: $[\alpha]_D^{25}$+36° (c0.5, MeOH)
(5) $^1$H NMR spectrum (400 MHz, CD$_3$OD) δ (ppm): 1.92 (2H, m, tetrahydropyrimidine), 2.92 (1H, dd, ArCH$_2$NBzlC$\underline{H}_2$), 3.06 (1H, dd, ArCH$_2$NBzlC$\underline{H}_2$), 3.24 (4H, m, piperazine), 3.36 (4H, t, tetrahydropyrimidine), 3.49 (4H, m, piperazine), 3.54 (1H, dd, PhSo$_2$NHC$\underline{H}$), 3.83 (2H, ABq, ArC$\underline{H}_2$), 3.91 (2H, ABq, ArC$\underline{H}_2$), 6.92 (2H, d, C$_6$H$_4$), 7.25 (2H, d, C$_6$H$_4$), 7.33 (5H, m, C$_6$$\underline{H}_5$CH$_2$N), 7.46 (2H, m, SO$_2$C$_6$H$_5$), 7.54 (1H, m, SO$_2$C$_6$H$_5$), 7.75 (2H, m, SO$_2$C$_6$H$_5$)

Example 27 t-Butyl (2S)-benzyloxycarbonylamino-3-[4-{4-(pyrimidin-2-yl)-piperazin-1-yl}-benzoylamino]-propionate Dimethylformamide (6.0 ml) was added to 101 mg of intermediate 3 to prepare a solution, and 107 mg of t-butyl (2S)-benzyloxycarbonyl-2,3-diaminopropionate was added to the solution. Further, 63 mg of 1-hydroxybenzotriazole, 0.70 ml of N-methylmorpholine, and 121 mg of 1-ethyl-3-(3-dimethylaminopropyl)carbodiimide hydrochloride were added to the mixture, and the mixture was stirred at room temperature for 24 hr. A saturated aqueous sodium hydrogencarbonate solution (60 ml) was added to the reaction solution to stop the reaction, and 60 ml of methylene chloride was added thereto. The organic layer was then separated, dried over anhydrous magnesium sulfate, and concentrated under the reduced pressure. The residue was purified by column chromatography on silica gel (development system:methylene chloride:methanol:concentrated aqueous ammonia=950:50:1) to prepare 53 mg of the title compound.

Physicochemical Properties of Compound Prepared in Example 27

(1) Color and form: Colorless solid
(2) Molecular formula: $C_{30}H_{36}N_6O_5$
(3) Mass spectrum (TSPMS): m/z 561 (M+H)$^+$
(4) $^1$H NMR spectrum (400 MHz, CDCl$_3$) δ (ppm): 1.46 (9H, s, t-Bu), 3.40 (4H, m, piperazine), 3.81 (2H, m, CONHC$\underline{H}_2$CH), 4.01 (4H, m, piperazine), 4.45 (1H, m, CONHCH$_2$C$\underline{H}$), 5.12 (2H, S, C$\underline{H}_2$C$_6$H$_5$), 6.57 (1H, t, pyrimidine), 6.92 (2H, d, C$_6$H$_4$), 7.31 (5H, m, CH$_2$C$_6$$\underline{H}_5$), 7.69 (2H, d, C$_6$H$_4$), 8.38 (2H, d, pyrimidine)

Example 28

(2S)-Benzyloxycarbonylamino-3-[4-{4-(pyrimidin-2-yl)-piperazin-1-yl}-benzoylamino]-propionic Acid Methylene chloride (5.0 ml) was added to 87 mg of the compound prepared in Example 27 to prepare a solution. Trifluoroacetic acid (1.0 ml) was added at room temperature to the solution. The mixture was stirred at that temperature for 5.5 hr before the reaction solution was concentrated under the reduced pressure. The residue was purified by preparative thin-layer chromatography on silica gel (development system:methylene chloride:methanol:concentrated aqueous ammonia=800:200:1), and then purified by Sephadex LH-20 (development system: methanol) to prepare 13 mg of the title compound.

Physicochemical Properties of Compound Prepared in Example 28

(1) Color and form: Colorless solid
(2) Molecular formula: $C_{26}H_{32}N_6O_5$
(3) Mass spectrum (TSPMS): m/z 505 (M+H)$^+$
(4) Specific rotation: $[\alpha]_D^{25}$-9.6° (c 0.072, MeOH)
(5) $^1$H NMR spectrum (400 MHz, CD$_3$OD) δ (ppm): 3.29 (4H, t, piperazine), 3.57 (1H, dd, CONHC$\underline{H}_2$CH), 3.65 (1H, dd, CONHC$\underline{H}_2$CH), 3.86 (4H, t, piperazine), 4.17 (1H, dd, CONHCH$_2$C$\underline{H}$), 4.96 (2H, dd, C$\underline{H}_2$C$_6$H$_5$), 6.52 (1H, t, pyrimidine), 6.91 (2H, d, C$_6$H$_4$), 7.19 (5H, m, CH$_2$C$_6$$\underline{H}_5$), 7.62 (2H, d, C$_6$H$_4$), 8.25 (2H, d, pyrimidine)

Example 29

(2S)-Amino-3-[4-{4-(1,4,5,6-tetrahydropyrimidin-2-yl)-piperazin-1-yl}-benzoylamino]-propionic Acid Acetic acid (10 ml) and 1.0 ml of concentrated hydrochloric acid were added to 10 mg of the compound prepared in Example 28 to prepare a solution. 10% Palladium-carbon (5.6 mg) was added to the solution, and the mixture was vigorously shaken at room temperature for 4 hr under a hydrogen pressure of 3 atom. The insolubles were collected by filtration, and then washed twice with water. The filtrate was combined with the washings, followed by concentration under the reduced pressure. The residue was purified by preparative thin-layer chromatography on silica gel (development system: ethanol-water-concentrated aqueous ammonia=4:1:1), and then purified by Sephadex LH-20 (development system: methanol-water=20:1) to prepare 4.9 mg of the title compound.

Physicochemical Properties of Compound Prepared in Example 29

(1) Color and form: Colorless solid
(2) Molecular formula: $C_{18}H_{26}N_6O_3$
(3) Mass spectrum (FABMS): m/z 375 $(M+H)^+$
(4) Specific rotation: $[\alpha]_D^{25}$ −6.2° (c 0.113, MeOH)
(5) $^1H$ NMR spectrum (400 MHz, $CD_3OD$) δ (ppm): 1.97 (2H, quintet, tetrahydropyrimidine), 3.43 (8H, m, piperazine), 3.56 (4H, m, tetrahydropyrimidine), 3.81 (3H, m, CONHC$\underline{H}_2$CH), 6.99 (2H, d, $C_6H_4$), 7.79 (2H, d, $C_6H_4$)

Example 30

(2S)-Benzyloxycarbonylamino-3-[4-{4-(1,4,5,6-tetrahydropyrimidin-2-yl)-piperazin-1-yl}-benzoylamino]-propionic Acid Acetone (1.0 ml) and 1.0 ml of water were added to 26 mg of the compound prepared in Example 29 to prepare a solution. Potassium carbonate (55 mg) was added to the solution. Benzyloxycarbonyl chloride (0.040 ml) was added to the mixture, and the mixture was stirred for 6.5 hr and then concentrated under the reduced pressure. The residue was purified by preparative thin-layer chromatography on silica gel (development system: ethanol-water-concentrated aqueous ammonia=6:1:1), and then purified by Sephadex LH-20 (development system: methanol-concentrated aqueous ammonia=9:1) to prepare 2.3 mg of the title compound.

Physicochemical Properties of Compound Prepared in Example 30

(1) Color and form: Colorless solid
(2) Molecular formula: $C_{26}H_{32}N_6O_5$
(3) Mass spectrum (TSPMS): m/z 509 $(M+H)^+$
(4) Specific rotation: $[\alpha]_D^{25}$ −3.4° (c 0.052, MeOH)
(5) $^1H$ NMR spectrum (400 MHz, $CD_3OD$) δ (ppm): 1.97 (2H, quintet, tetrahydropyrimidine), 3.40 (8H, m, piperazine and tetrahydropyrimidine), 3.54 (4H, m, piperazine), 3.71 (2H, m, CONHC$\underline{H}_2$CH), 4.24 (1H, m, CONHCH$_2$C$\underline{H}$), 5.05 (2H, dd, C$\underline{H}_2C_6H_5$), 6.94 (2H, d, $C_6H_4$), 7.28 (5H, m, $CH_2C_6\underline{H}_5$), 7.71 (2H, d, $C_6H_4$)

Intermediate 18: t-Butyl (2S)-benzenesulfonylamino-3-cyclopropylmethylamino-propionate 50% methanol/methylene chloride (12 ml) was added to 116 mg of t-butyl (2S)-benzenesulfonyl-2,3-diaminopropionate to prepare a solution. Cyclopropanecarboxaldehyde (31 mg) was added to the solution. The reaction solution was adjusted to pH 3 to 4 by the addition of a minor amount of acetic acid. Sodium boron cyanohydride (48 mg) was then added thereto, and a reaction was allowed to proceed at room temperature for 2 hr. The reaction solution was concentrated under the reduced pressure. A saturated aqueous sodium hydrogencarbonate solution (10 ml) was added to the residue, followed by extraction twice each with 10 ml of chloroform. The chloroform layers were combined, followed by concentration under the reduced pressure. The residue was purified by column chromatography on silica gel (development system: chloroform-methanol-concentrated aqueous ammonia=1000:30:1) to prepare 74 mg of the title compound.

Physicochemical Properties of Intermediate 18

(1) Color and form: Colorless oil
(2) Molecular formula: $C_{17}H_{26}N_2O_4S$
(3) Mass spectrum (TSPMS): m/z 355 $(M+H)^+$
(4) Specific rotation: $[\alpha]_D^{25}$ +22° (c1.0, $CHCl_3$)
(5) $^1H$ NMR spectrum (400 MHz, $CDCl_3$) δ (ppm): 0.09 (2H, m, cyclopropyl), 0.45 (2H, m, cyclopropyl), 0.87 (1H, m, cyclopropyl), 2.41 (2H, m, $C_3H_5C\underline{H}_2$), 2.86 (1H, dd, $C_3H_5CH_2$ NHC$\underline{H}_2$), 2.93 (1H, dd, $C_3H_5CH_2$ NHC$\underline{H}_2$), 3.91 (1H, dd, PhSO$_2$NHC$\underline{H}$), 7.50 (2H, m, $SO_2C_6H_5$), 7.57 (1H, m, $SO_2C_6H_5$), 7.86 (2H, m, $SO_2C_6H_5$)

Example 31 t-Butyl (2S)-benzenesulfonylamino-3-[cyclopropylmethyl-[4-{4-(pyrimidin-2-yl)-piperazin-1-yl}-benzoyl]-amino-]-propionate Dimethylformamide (3.0 ml) was added to 28 mg of intermediate 3 to prepare a solution. t-Butyl (2S)-benzenesulfonyl-3-N-cyclopropylmethyl-2,3-diaminopropionate (31 mg) was added to the solution. Further, 22 mg of 1-hydroxybenzotriazole, 0.050 ml of N-methylmorpholine, and 52 mg of 1-ethyl-3-(3-dimethylaminopropyl)carbodiimide hydrochloride were added thereto, and the mixture was stirred at room temperature for 48 hr. A saturated aqueous sodium hydrogencarbonate solution (30 ml) was added to stop the reaction, and 30 ml of methylene chloride was added thereto. The organic layer was then separated, dried over anhydrous magnesium sulfate, and concentrated under the reduced pressure. The residue was purified by preparative thin-layer chromatography on silica gel (development system: hexane-ethyl acetate=1:2) to prepare 23 mg of the title compound.

Physicochemical Properties of Compound Prepared in Example 31

(1) Color and form: Colorless oil
(2) Molecular formula: $C_{32}H_{40}N_6O_5S$
(3) Mass spectrum (TSPMS): m/z 621 $(M+H)^+$
(4) $^1H$ NMR spectrum (400 MHz, $CDCl_3$) δ (ppm): 0.11 (2H, m, $CH_2C_3\underline{H}_5$), 0.53 (2H, m, $CH_2C_3\underline{H}_5$), 0.87 (1H, m, $CH_2C_3\underline{H}_5$), 1.28 (9H, s, t-Bu), 3.22 (1H, dd, C$\underline{H}_2C_3H_5$), 3.34 (5H, m, piperazine and C$\underline{H}_2C_3H_5$), 3.82 (1H, dd, CONHC$\underline{H}_2$CH), 3.99 (5H, m, piperazine and CONHC$\underline{H}_2$CH), 4.24 (1H, m, CONHCH$_2$C$\underline{H}$), 6.54 (1H, t, pyrimidine), 6.94 (2H, d, $C_6H_4$), 7.39 (2H, d, $C_6H_4$), 7.46 (2H, br t, $C_6H_5$), 7.53 (1H, dt, $C_6H_5$), 7.86 (2H, d, $C_6H_5$), 8.35 (2H, d, pyrimidine)

Example 32

(2S)-Benzenesulfonylamino-3-[cyclopropylmethyl-[4-{4-(pyrimidin-2-yl)-piperazin-1-yl}-benzoyl]-amino-]-propionic Acid Methylene chloride (0.50 ml) was added to 23 mg of the compound prepared in Example 31 to prepare a solution. Anisole (0.020 ml) and 0.50 ml of trifluoroacetic acid were added at 0° C. The mixture was stirred at room temperature for 3 hr. The reaction solution was then concentrated under the reduced pressure. The residue was purified by preparative thin-layer chromatography on silica gel (development system: chloroform-methanol=5:1) to prepare 15 mg of the title compound.

Physicochemical Properties of Compound Prepared in Example 32
(1) Color and form: Colorless solid
(2) Molecular formula: $C_{28}H_{32}N_6O_5S$
(3) Mass spectrum (ESI (electrospray ionization) MS): m/z 563 (M–H)⁻
(4) Specific rotation: $[\alpha]_D^{25}$+41° (c 0.75, MeOH)
(5) ¹H NMR spectrum (400 MHz, Acetone-d) δ (ppm): 0.04 (2H, m, $CH_2C_3\underline{H}_5$), 0.39 (2H, m, $CH_2C_3\underline{H}_5$), 0.83 (1H, m, $CH_2C_3\underline{H}_5$), 3.23 (2H, m, $C\underline{H}_2C_3H_5$), 3.31 (4H, m, piperazine), 3.71 (1H, m, $CONHC\underline{H}_2CH$), 3.95 (4H, m, piperazine), 4.11 (2H, m, $CONHCH_2C\underline{H}$), 6.59 (1H, t, pyrimidine), 6.97 (2H, br d, $C_6H_4$), 7.32 (2H, m, $C_6H_4$), 7.50 (3H, m, $C_6H_5$), 7.86 (2H, m, $C_6H_5$), 8.35 (2H, d, pyrimidine)

Example 33

(2S)-Benzenesulfonylamino-3-[cyclopropylmethyl-[4-{4-(1,4,5,6-tetrahydropyrimidin-2-yl)-piperazin-1-yl}-benzoyl]-amino]-propionic Acid Acetic acid (5.0 ml) and 0.50 ml of concentrated hydrochloric acid were added to 14 mg of the compound prepared in Example 32 to prepare a solution. 10% palladium-carbon (7.0 mg) was added to the solution. The mixture was vigorously shaken at room temperature for 1.5 hr under a hydrogen pressure of 3 atm. The insolubles were collected by filtration, and then washed twice with water. The filtrate was combined with the washings, followed by concentration under the reduced pressure. The residue was purified by column chromatography on silica gel (development system: ethanol-water-concentrated aqueous ammonia=8:1:1), and then purified by Sephadex LH-20 (development system: methanol-0.05 N hydrochloric acid=1:1) to prepare 10 mg of trihydrochloride of the title compound.

Physicochemical Properties of Compound Prepared in Example 33
(1) Color and form: Colorless solid
(2) Molecular formula: $C_{28}H_{36}N_6O_5S$
(3) Mass spectrum (ESIMS): m/z 569 (M+H)⁺
(4) Specific rotation: $[\alpha]_D^{25}$+33° (c 0.50, MeOH) (as trihydrochloride)
(5) ¹H NMR spectrum (400 MHz, $CD_3OD$) (as trihydrochloride) δ (ppm): 0.09 (2H, br d, $CH_2C_3\underline{H}_5$), 0.52 (2H, m, $CH_2C_3\underline{H}_5$), 0.92 (1H, m, $CH_2C_3\underline{H}_5$), 1.98 (2H, quintet, tetrahydropyrimidine), 3.27 (2H, m, $C\underline{H}_2C_3H_5$), 3.43 (4H, t, tetrahydropyrimidine), 3.62 (4H, m, piperazine), 3.77 (5H, m, piperazine and $CONHC\underline{H}_2CH$), 4.03 (1H, m, $CONHC\underline{H}_2CH$), 4.45 (1H, m, $CONHCH_2C\underline{H}$), 7.44 (2H, br d, $C_6H_4$), 7.53 (4H, m, $C_6H_4$ and $C_6H_5$), 7.61 (1H, br t, $C_6H_5$), 7.86 (2H, br d, $C_6H_5$)

Intermediate 19: 4-{4-(t-Butoxycarbonyl)piperazin-1-yl}-benzoic Acid 1,4-Dioxane (10 ml) and 5.0 ml of water were added to 500 mg of intermediate 1 to prepare a solution. A 1 N aqueous sodium hydroxide solution (3.0 ml) and 465 mg of di-t-butyl dicarbonate were added at room temperature to the solution. After stirring for 1 hr, the reaction solution was concentrated under the reduced pressure to prepare ethyl 4-(4-(t-butoxycarbonyl)piperazinyl)benzoate. Tetrahydrofuran (20 ml) and 5.0 ml of methanol were added to this compound to prepare a solution, and 20 ml of a 1 N aqueous sodium hydroxide solution (20 ml) was added to the solution. The mixture was stirred at 50° C. for 8.0 hr and was then cooled to room temperature. The system was adjusted to pH 7 by the addition of 1 N hydrochloric acid, and concentrated under the reduced pressure. The residue was purified by column chromatography on silica gel (development system: methylene chloride-ethanol-water-concentrated aqueous ammonia=8:8:1:1) to prepare 400 mg of the title compound.

Physicochemical Properties of Intermediate 19
(1) Color and form: Colorless solid
(2) Molecular formula: $C_{16}H_{22}N_2O_4$
(3) Mass spectrum (TSPMS): m/z 307 (M+H)⁺
(4) ¹H NMR spectrum (400 MHz, $CD_3OD$) δ (ppm): 1.48 (9H, s, t-Bu), 3.26 (4H, br t, piperazine), 3.57 (4H, br t, piperazine), 6.94 (2H, d, $C_6H_4$), 7.87 (2H, d, $C_6H_4$)

Intermediate 20: (2S)-Benzenesulfonylamino-3-[4-{4-(t-butoxycarbonyl)-piperazin-1-yl}-benzoylamino]-propionic Acid Dimethylformamide (2.0 ml) was added to 63 mg of 4-(4-(t-butoxycarbonyl)piperazinyl)benzoic acid to prepare a solution, and 61 mg of t-butyl (2S)-benzenesulfonyl-2,3-diaminopropionate was added to the solution. Further, 42 mg of 1-hydroxybenzotriazole, 0.50 ml of N-methylmorpholine, and 81 mg of 1-ethyl-3-(3-dimethylaminopropyl) carbodiimide hydrochloride were added thereto, and the mixture was stirred at room temperature for 18 hr. A saturated aqueous sodium hydrogencarbonate solution (20 ml) was added to stop the reaction. Methylene chloride (20 ml) was added thereto. The organic layer was then separated, dried over anhydrous magnesium sulfate, and concentrated under the reduced pressure. The residue was purified by column chromatography on silica gel (development system: hexane-ethyl acetate=2:3) to prepare t-butyl (2S)-benzenesulfonyl-3-N-(4-piperazinylphenyl)carbonyl-2,3-diaminopropionate. Trifluoroacetic acid (2.8 ml) and 0.2 ml of water were then added to 31 mg of this compound to prepare a solution. The mixture was stirred at room temperature for 1 hr before the reaction solution was concentrated under the reduced pressure. The residue was purified by column chromatography on silica gel (development system: methylene chloride-ethanol-water-concentrated aqueous ammonia=8:8:1:1), and then purified by Sephadex LH-20(development system: methanol-concentrated aqueous ammonia=20:1) to prepare 7.9 mg of the title compound.

Physicochemical Properties of Intermediate 20
(1) Color and form: Colorless solid
(2) Molecular formula: $C_{20}H_{24}N_4O_5S$
(3) Mass spectrum (TSPMS): m/z 433 (M+H)⁺
(4) ¹H NMR spectrum (400 MHz, $CD_3OD$) δ (ppm): 3.30 (5H, m, piperazine, $CONHC\underline{H}_2CH$), 3.45 (4H, t, piperazine), 3.62 (1H, dd, $CONHC\underline{H}_2CH$), 4.04 (1H, dd, $CONHCH_2C\underline{H}$), 6.94 (2H, d, $C_6H_4$), 7.21 (3H, m, $C_6H_5$), 7.40 (2H, d, $C_6H_4$), 7.61 (2H, d, $C_6H_5$)

Example 34

(2S)-Benzenesulfonylamino-3-[4-{4-(amidino)-piperazin-1-yl}-benzoylamino]-propionic Acid Pyridine (10 ml) was added to 35 mg of (2S)-benzenesulfonyl-3-N-(4-piperazinylphenyl)carbonyl-2,3- diaminopropionic acid to prepare a solution, and 22 mg of 3,5-dimethylpyrazole-1-carboxyamidine nitrate was added to the solution. The mixture was stirred at 90° C. for 20 hr. The reaction solution was then concentrated under the reduced pressure. The residue was purified by column chromatography on silica gel (development system: methylene chloride-ethanol-water-concentrated aqueous ammonia=8:8:1:1), and then purified by Sephadex G-10 (development system: 0.05 N hydrochloric acid) to prepare 5.3 mg of trihydrochloride of the title compound.

Physicochemical Properties of Compound Prepared in Example 34

(1) Color and form: Colorless solid
(2) Molecular formula: $C_{21}H_{26}N_6O_5S$
(3) Mass spectrum (TSPMS): m/z 475 (M+H)$^+$
(4) Specific rotation: $[\alpha]_D^{25}+45°$ (c 0.26, MeOH) (as trihydrochloride)
(5) $^1$H NMR spectrum (400 MHz, CD$_3$OD) (as trihydrochloride) δ (ppm): 3.49 (1H, dd, CONHC$\underline{H}_2$CH), 3.51 (4H, m, piperazine), 3.71 (4H, m, piperazine), 3.72 (1H, dd, CONHC$\underline{H}_2$CH), 4.18 (1H, dd, CONHCH$_2$C$\underline{H}$), 7.06 (2H, d, C$_6$H$_4$), 7.43 (2H, m, C$_6$H$_5$), 7.50 (1H, m, C$_6$H$_5$), 7.73 (2H, d, C$_6$H$_4$), 7.82 (2H, m, C$_6$H$_5$)

Intermediate 21: Ethyl 4-{cis-3,5-dimethyl-(piperazin-1-yl)}-benzoate

Dimethyl sulfoxide (10 ml) was added to 3.6 g of cis-2,6-dimethylpiperazine to prepare a suspension, and 2.5 g of ethyl 4-fluorobenzoate was added to the suspension. The mixture was stirred at 80° C. for 24 hr and was then cooled to room temperature, and 100 mg of water was added thereto. The mixture was extracted three times with 100 ml of ethyl acetate. The combined organic layer was dried over anhydrous magnesium sulfate, and concentrated under the reduced pressure. The residue was purified by column chromatography on silica gel (development system: methylene chloride-methanol-concentrated aqueous ammonia= 900:100:1) to prepare 1.5 g of the title compound.

Physicochemical Properties of Intermediate 21

(1) Color and form: Colorless solid
(2) Molecular formula: $C_{15}H_{22}N_2O_2$
(3) Mass spectrum (TSPMS): m/z 263 (M+H)$^+$
(4) $^1$H NMR spectrum (400 MHz, CD$_3$OD) δ (ppm): 1.16 (6H, d, C$\underline{H}_3$) 1.35 (3H, t, CH$_2$C$\underline{H}_3$), 2.38 (2H, dd, piperazine), 2.95 (2H, m, piperazine), 3.78 (2H, dd, piperazine), 4.29 (2H, q, C$\underline{H}_2$CH$_3$), 6.95 (2H, d, C$_6$H$_4$), 7.86 (2H, d, C$_6$H$_4$)

Intermediate 22: Ethyl 4-{cis-3,5-dimethyl-4-(pyrimidin-2-yl)-piperazin-1-yl}-benzoate Dimethylformamide (15 ml) was added to 417 mg of intermediate 21 to prepare a solution, and 261 mg of 2-bromopyrimidine was added to the solution. Diisopropylethylamine (1.0 ml) was added thereto, and the mixture was stirred at 80° C. for 48 hr and was then cooled to room temperature, and the system was concentrated under the reduced pressure. Methylene chloride (200 ml) and 200 ml of water were added to the residue. Thereafter, the organic layer was separated, dried over anhydrous magnesium sulfate, and concentrated under the reduced pressure. The residue was purified by column chromatography on silica gel (development system: hexane-ethyl acetate=1:1) to prepare 26 mg of the title compound.

Physicochemical Properties of Intermediate 22

(1) Color and form: Colorless solid
(2) Molecular formula: $C_{19}H_{24}N_4O_2$
(3) Mass spectrum (ESIMS): m/z 341 (M+H)$^+$
(4) $^1$H NMR spectrum (400 MHz, CDCl$_3$) δ (ppm): 1.36 (6H, d, CH$_3$), 1.38 (3H, t, CH$_2$C$\underline{H}_3$), 3.15 (2H, dd, piperazine), 3.74 (2H, dd, piperazine), 4.34 (2H, q, C$\underline{H}_2$CH$_3$), 4.89 (2H, m, piperazine), 6.53 (1H, t, pyrimidine), 6.92 (2H, d, C$_6$H$_4$), 7.95 (2H, d, C$_6$H$_4$), 8.36 (2H, d, pyrimidine)

Intermediate 23: 4-{cis-3,5-Dimethyl-4-(pyrimidin-2-yl)-piperazin-1-yl}-benzoic Acid Methanol (1.0 ml) and 3.0 ml of tetrahydrofuran were added to 26 mg of intermediate 22 to prepare a solution, and 2.0 ml of a 1 N aqueous sodium hydroxide solution was added to the solution. The mixture was stirred at 50° C. for 19 hr, and was then cooled to room temperature, followed by adjustment to pH 5 by the addition of 1 N hydrochloric acid. Ethyl acetate and water were added thereto. The organic layer was separated, dried over anhydrous magnesium sulfate, and concentrated under the reduced pressure to prepare 22 mg of the title compound.

Physicochemical Properties of Intermediate 23

(1) Color and form: Colorless solid
(2) Molecular formula: $C_{17}H_{20}N_4O_2$
(3) Mass spectrum (ESIMS): m/z 313 (M+H)$^+$
(4) $^1$H NMR spectrum (400 MHz, CD$_3$OD) δ (ppm): 1.33 (6H, d, CH$_3$), 3.11 (2H, dd, piperazine), 3.89 (2H, d, piperazine), 4.87 (2H, m, piperazine), 6.61 (1H, t, pyrimidine), 7.02 (2H, d, C$_6$H$_4$), 7.90 (2H, d, C$_6$H$_4$), 8.36 (2H, d, pyrimidine)

Example 35 t-Butyl (2S)-benzenesulfonylamino-3-[4-{cis-3,5-dimethyl-4-(pyrimidin-2-yl)-piperazin-1-yl}-benzoylamino]-propionate Dimethylformamide (4.0 ml) was added to 20 mg of intermediate 23 to prepare a solution. t-Butyl (2S)-benzenesulfonyl-2,3-diaminopropionate (20 mg) was added to the solution. Further, 15 mg of 1-hydroxybenzotriazole, 0.05 ml of N-methylmorpholine, and 30 mg of 1-ethyl-3-(3-dimethylaminopropyl)carbodiimide hydrochloride were added thereto, and the mixture was stirred at room temperature for 24 hr. A saturated aqueous sodium hydrogencarbonate solution (40 ml) was added to stop the reaction, and 200 ml of methylene chloride was added thereto. The organic layer was then separated, dried over anhydrous magnesium sulfate, and then concentrated under the reduced pressure. The residue was purified by preparative thin-layer chromatography on silica gel (development system: hexane-ethyl acetate=1:2) to prepare 25 mg of the title compound.

Physicochemical Properties of Compound Prepared in Example 35

(1) Color and form: Colorless solid
(2) Molecular formula: $C_{30}H_{38}N_6O_5S$
(3) Mass spectrum (TSPMS): m/z 595 (M+H)$^+$
(4) $^1$H NMR spectrum (400 MHz, CDCl$_3$) δ (ppm): 1.29 (9H, s, t-Bu), 1.38 (6H, d, CH$_3$), 3.13 (2H, dd, piperazine), 3.56 (1H, m, CONHC$\underline{H}_2$CH), 3.70 (2H, d, piperazine), 3.91 (2H, m, CONHC$\underline{H}_2$CH), 4.89 (2H, m, piperazine), 6.52 (1H, t, pyrimidine), 6.96 (2H, d, C$_6$H$_4$), 7.50 (2H, m, C$_6$H$_5$), 7.58 (1H, m, C$_6$H$_5$), 7.74 (2H, d, C$_6$H$_4$), 7.87 (2H, m, C$_6$H$_5$), 8.37 (2H, d, pyrimidine)

Example 36

(2S)-Benzenesulfonylamino-3-[4-{cis-3,5-dimethyl-4-(pyrimidin-2-yl)-piperazin-1-yl}-benzoylamino]-propionic Acid Methylene chloride (2.0 ml) was added to 24 mg of the compound prepared in Example 35 to prepare a solution, and 1.0 ml of trifluoroacetic acid was added at room temperature to the solution. The mixture was stirred at that temperature for 6 hr before the reaction solution was concentrated under the reduced pressure to prepare 25 mg of tritrifluoroacetate of the title compound.

Physicochemical Properties of Compound Prepared in Example 36
(1) Color and form: Yellow solid
(2) Molecular formula: $C_{26}H_{30}N_6O_5S$
(3) Mass spectrum (TSPMS): m/z 539 (M+H)$^+$
(4) Specific rotation: $[\alpha]_D^{25}$ +46° (c 0.072, MeOH)(as tritrifluoroacetate)
(5) $^1$H NMR spectrum (400 MHz, CD$_3$OD)(as tritrifluoroacetate) $\delta$ (ppm): 1.37 (6H, d, CH$_3$), 3.11 (2H, m, piperazine), 3.48 (1H, dd, CONHC$\underline{H}_2$CH), 3.70 (1H, dd, CONHC$\underline{H}_2$CH), 3.85 (2H, br d, piperazine), 4.17 (1H, dd, CONHCH$_2$C$\underline{H}$), 4.84 (2H, m, piperazine), 6.71 (1H, t, pyrimidine), 7.02 (2H, d, C$_6$H$_4$), 7.42 (2H, m, C$_6$H$_5$), 7.49 (1H, m, C$_6$H$_5$), 7.67 (2H, d, C$_6$H$_4$), 7.82 (2H, m, C$_6$H$_5$), 8.43 (2H, d, pyrimidine)

Example 37

(2S)-Benzenesulfonylamino-3-[4-{cis-3,5-dimethyl-4-(1,4,5,6-tetrahydropyrimidin-2-yl)-piperazin-1-yl}-benzoylamino]-propionic Acid Acetic acid (18 ml) and 1.8 ml of concentrated hydrochloric acid were added to 19 mg of the compound prepared in Example 36 to prepare a solution, and 10 mg of 10% palladium-carbon was added to the solution. The mixture was vigorously shaken at room temperature for 5 hr under a hydrogen pressure of 3 atm. The insolubles were collected by filtration, and then washed twice with water. The filtrate was combined with the washings, followed by concentration under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 6.9 mg of the title compound.

Physicochemical Properties of Compound Prepared in Example 37
(1) Color and form: Colorless solid
(2) Molecular formula: $C_{26}H_{34}N_6O_5S$
(3) Mass spectrum (FABMS): m/z 543 (M+H)$^+$
(4) Specific rotation: $[\alpha]_D^{25}$ +79° (c 0.28, MeOH)
(5) $^1$H NMR spectrum (400 MHz, CD$_3$OD) $\delta$ (ppm): 1.40 (6H, d, CH$_3$), 1.98 (2H, quintet, tetrahydropyrimidine), 3.12 (2H, m, piperazine), 3.44 (4H, br t, tetrahydropyrimidine), 3.57 (1H, dd, CONHC$\underline{H}_2$CH), 3.66 (1H, dd, CONHC$\underline{H}_2$CH), 3.73 (2H, m, piperazine), 3.83 (2H, m, piperazine), 3.98 (1H, m, CONHCH$_2$C$\underline{H}$), 7.01 (2H, d, C$_6$H$_4$), 7.48 (2H, m, C$_6$H$_5$), 7.55 (1H, m, C$_6$H$_5$), 7.75 (2H, d, C$_6$H$_4$), 7.85 (2H, m, C$_6$H$_5$)

Example 38 t-Butyl 3-[4-{4-(1H-benzimidazol-2-yl)-piperazin-1-yl}-benzoylamino]-(2S)-benzyloxycarbonylamino-propionate Dimethylformamide (8.0 ml) was added to 70 mg of intermediate 17 to prepare a solution, and 67 mg of t-butyl (2S)-benzyloxycarbonyl-2,3-diaminopropionate was added to the solution. Further, 48 mg of 1-hydroxybenzotriazole, 0.15 ml of N-methylmorpholine, and 92 mg of 1-ethyl-3-(3-dimethylaminopropyl)carbodiimide hydrochloride was added thereto, and the mixture was stirred at room temperature for 23 hr. A saturated aqueous sodium hydrogencarbonate solution (80 ml) was added to stop the reaction. Methylene chloride (100 ml) was added thereto. The organic layer was then separated, dried over anhydrous magnesium sulfate, and concentrated under the reduced pressure. The residue was purified by column chromatography on silica gel (development system: hexane-ethyl acetate-methanol= 1:5:1) to prepare 102 mg of the title compound.

Physicochemical Properties of Compound Prepared in Example 38
(1) Color and form: Colorless solid
(2) Molecular formula: $C_{33}H_{38}N_6O_5$
(3) Mass spectrum (FABMS): m/z 599 (M+H)$^+$
(4) $^1$H NMR spectrum (400 MHz, CD$_3$OD) $\delta$ (ppm): 1.42 (9H, s, t-Bu), 3.47 (4H, m, piperazine), 3.69 (6H, m, CONHC$\underline{H}_2$CH and piperazine), 4.36 (1H, t, CONHCH$_2$C$\underline{H}$), 5.08 (2H, d, C$\underline{H}_2$C$_6$H$_5$), 7.02 (2H, dd, benzimidazole), 7.04 (2H, d, C$_6$H$_4$), 7.27 (2H, dd, benzimidazole), 7.30 (5H, m, C$_6$H$_5$), 7.73 (2H, d, C$_6$H$_4$)

Example 39

3-[4-{4-(1H-Benzimidazol-2-yl)-piperazin-1-yl}-benzoylamino]-(2S)-benzyloxycarbonylamino-propionic Acid Trifluoroacetic acid (1.0 ml) was added to 10 mg of the compound prepared in Example 38 to prepare a solution, and 0.05 ml of water was added at room temperature to the solution. The mixture was stirred at that temperature for 4 hr before the reaction solution was concentrated under the reduced pressure. The residue was purified by preparative thin-layer chromatography on silica gel (development system: methylene chloride-ethanol-water-concentrated aqueous ammonia=8:8:1:1), and then purified by Sephadex LH-20 (development system: methanol) to prepare 5.2 mg of the title compound.

Physicochemical Properties of Compound Prepared in Example 39
(1) Color and form: Colorless solid
(2) Molecular formula: $C_{29}H_{30}N_6O_5$
(3) Mass spectrum (TSPMS): m/z 543 (M+H)$^+$
(4) Specific rotation: $[\alpha]_D^{25}$ +21° (c 0.053, MeOH)
(5) $^1$H NMR spectrum (400 MHz, CD$_3$OD) $\delta$ (ppm): 3.60 (4H, m, piperazine), 3.70 (1H, dd, CONHC$\underline{H}_2$CH), 3.82 (1H, dd, CONHC$\underline{H}_2$CH), 3.85 (4H, m, piperazine), 4.48 (1H, dd, CONHCH$_2$C$\underline{H}$), 5.07 (2H, dd, C$\underline{H}_2$C$_6$H$_5$), 7.05 (2H, m, C$_6$H$_4$), 7.29 (5H, m, C$_6$H$_5$), 7.33 (2H, dd, benzimidazole), 7.42 (2H, dd, benzimidazole), 7.75 (2H, m, C$_6$H$_4$)

Intermediate 24: t-Butyl (2S)-benzenesulfonylamino-3-propylamino-propionate

50% methanol/methylene chloride (20 ml) was added to 200 mg of t-butyl 3-amino-(2S)-benzenesulfonylamino-propionate to prepare a solution, and 33 mg of propionaldehyde was added to the solution. The reaction solution was adjusted to pH 3 to 4 by the addition of a minor amount of acetic acid, and 84 mg of sodium boron cyanohydride was added thereto. A reaction was allowed to proceed at room temperature for 2 hr. Further, 25 mg of propionaldehyde was added, and a reaction was allowed to proceed at room temperature for additional 2 hr. The reaction solution was concentrated under the reduced pressure. A saturated aqueous sodium hydrogencarbonate solution (20 ml) was added to the reside, and the mixture was extracted twice each with 20 ml of chloroform. The chloroform layers were combined, and then concentrated under the reduced pressure. The residue was purified by column chromatography on silica gel (development system: chloroform-methanol-concentrated aqueous ammonia=1000:30:1) to prepare 166 mg of the title compound.

Physicochemical Properties of Intermediate 24
Color and form: Colorless platy crystal
Melting point: 53–55° C.
(3) Molecular formula: $C_{16}H_{26}N_2O_4S$
(4) Mass spectrum (TSPMS): m/z 343 (M+H)$^+$
(5) Specific rotation: $[\alpha]_D^{25}$+16° (c1.0, CHCl$_3$)
(6) $^1$H NMR spectrum (400 MHz, CDCl$_3$) δ (ppm): 0.88 (3H, t, propyl), 1.28 (9H, s, t-Bu), 1.43 (2H, sextet, propyl), 2.46 (1H, dt, propyl), 2.55 (1H, dt, propyl), 2.83 (1H, dd, PrNHCH$_2$), 2.89 (1H, dd, PrNHCH$_2$), 3.90 (1H, dd, PrNHCH$_2$H), 7.50 (2H, m, C$_6$H$_5$), 7.57 (1H, m, C$_6$H$_5$), 7.87 (2H, m, C$_6$H$_5$)

Example 40 t-Butyl (2S)-benzenesulfonylamino-3-[propyl-[4-{4-(pyrimidin-2-yl)-piperazin-1-yl}-benzoyl]-amino]-propionate Dimethylformamide (4.0 ml) was added to 22 mg of intermediate 3 to prepare a solution, and 27 mg of t-butyl (2S)-benzenesulfonylamino-3-n-propylamino-propionate was added to the solution. Further, 17 mg of 1-hydroxybenzotriazole, 0.045 ml of N-methylmorpholine, and 30 mg of 1-ethyl-3-(3-dimethylaminopropyl) carbodiimide hydrochloride were added thereto, and the mixture was stirred at room temperature for 43 hr. A saturated aqueous sodium hydrogencarbonate solution (40 ml) was added to stop the reaction. The mixture was extracted three times with 40 ml of methylene chloride. The combined organic layer was dried over anhydrous magnesium sulfate, and concentrated under the reduced pressure. The residue was purified by column chromatography on silica gel (development system: hexane-ethyl acetate=1:2) to prepare 29 mg of the title compound.

Physicochemical Properties of Compound Prepared in Example 40
(1) Color and form: Colorless oil
(2) Molecular formula: $C_{31}H_{40}N_6O_5S$
(3) Mass spectrum (ESIMS): m/z 609 (M+H)$^+$
(4) $^1$H NMR spectrum (400 MHz, CDCl$_3$) δ (ppm): 0.77 (3H, t, CH$_2$CH$_2$CH$_3$), 1.27 (9H, s, t-Bu), 1.53 (2H, m, CH$_2$CH$_2$CH$_3$), 3.36 (6H, m, piperazine and CH$_2$CH$_2$CH$_3$), 3.71 (2H, d, CONHCH$_2$CH), 4.00 (4H, t, piperazine), 4.23 (1H, m, CONHCH$_2$CH), 6.53 (1H, t, pyrimidine), 6.94 (2H, d, C$_6$H$_4$), 7.39 (2H, d, C$_6$H$_4$), 7.48 (2H, m, C$_6$H$_5$), 7.55 (1H, m, C$_6$H$_5$), 7.86 (2H, d, C$_6$H$_5$), 8.34 (2H, d, pyrimidine)

Example 41

(2S)-Benzenesulfonylamino-3-[propyl-[4-{4-(pyrimidin-2-yl)-piperazin-1-yl}-benzoyl]-amino]-propionic Acid Methylene chloride (2.0 ml) was added to 26 mg of the compound prepared in Example 40 to prepare a solution, and 1.0 ml of trifluoroacetic acid was added at room temperature to the solution. The mixture was stirred at that temperature for 5.5 hr. The reaction solution was then concentrated under the reduced pressure. The residue was purified by column chromatography on silica gel (development system: chloroform-methanol=5:1), and then purified by Sephadex LH-20 (development system: methanol) to prepare 22 mg of the title compound.

Physicochemical Properties of Compound Prepared in Example 41
(1) Color and form: Colorless oil
(2) Molecular formula: $C_{27}H_{32}N_6O_5S$
(3) Mass spectrum (TSPMS): m/z 553 (M+H)$^-$
(4) Specific rotation: $[\alpha]_D^{25}$+33° (c 1.1, MeOH)
(5) $^1$H NMR spectrum (400 MHz, CDCl$_3$) δ (ppm): 0.76 (3H, t, CH$_2$CH$_2$CH$_3$), 1.55 (2H, q, CH$_2$CH$_2$CH$_3$), 3.36 (4H, br t, piperazine), 3.40 (2H, m, CH$_2$CH$_2$CH$_3$), 3.72 (1H, m, CONHCH$_2$CH), 3.89 (1H, m, CONHCH$_2$CH), 3.99 (4H, br t, piperazine), 4.08 (1H, m, CONHCH$_2$CH), 6.58 (1H, t, pyrimidine), 6.91 (2H, d, C$_6$H$_4$), 7.35 (2H, d, C$_6$H$_4$), 7.46 (2H, t, C$_6$H$_5$), 7.54 (1H, t, C$_6$H$_5$), 7.84 (2H, d, C$_6$H$_5$), 8.37 (2H, d, pyrimidine)

Example 42

(2S)-Benzenesulfonylamino-3-[propyl-[4-{4-(1,4,5,6-tetrahydropyrimidin-2-yl)-piperazin-1-yl}-benzoyl]-amino]-propionic Acid Acetic acid (20 ml) and 2.0 ml of concentrated hydrochloric acid were added to 19 mg of the compound prepared in Example 41 to prepare a solution, and 9.9 mg of 10% palladium-carbon was added to the solution. The mixture was vigorously shaken at room temperature for 4 hr under a hydrogen pressure of 3 atm. The insolubles were collected by filtration, and then washed twice with water. The filtrate was combined with the washings, followed by concentration under the reduced pressure. The residue was purified by column chromatography on silica gel (development system: methylene chloride-ethanol-water-concentrated aqueous ammonia=8:8:1:1), and then purified by Sephadex LH-20 (development system: methanol) to prepare 10 mg of the title compound.

Physicochemical Properties of Compound Prepared in Example 42
(1) Color and form: Colorless solid
(2) Molecular formula: $C_{27}H_{36}N_6O_5S$
(3) Mass spectrum (FABMS): m/z 557 (M+H)$^+$
(4) Specific rotation: $[\alpha]_D^{25}$+53° (c 0.075, MeOH)
(5) $^1$H NMR spectrum (400 MHz, D$_2$O) (as trihydrochloride) (rotational isomers being present) δ (ppm): 1.18 (3H, t, CH$_2$CH$_2$CH$_3$), 1.41 (2H, q, CH$_2$CH$_2$CH$_3$), 1.89 (2H, quintet, tetrahydropyrimidine), 3.24 (2H, t, CH$_2$CH$_2$CH$_3$), 3.33 (4H, br t, tetrahydropyrimidine), 3.37 (4H, m, piperazine), 3.54 (4H, m, piperazine), 3.59 (1H, dd, CONHCH$_2$CH), 3.84 (1H, dd, CONHCH$_2$CH), 4.39 (1H, dd, CONHCH$_2$CH), 7.54 (4H, m, C$_6$H$_4$ and C$_6$H$_5$), 7.64 (3H, m, C$_6$H$_4$ and C$_6$H$_5$), 7.83 (2H, m, C$_6$H$_5$)

Example 43

(2S)-t-Butoxycarbonylamino-3-[4-{4-(1,4,5,6-tetrahydropyrimidin-2-yl)-piperazin-1-yl}-benzoylamino]-propionic Acid A 1 N aqueous sodium hydroxide solution (2.0 ml) was added to 22 mg of the compound prepared in Example 29, and an excess of di-t-butyl dicarbonate was added to the solution. The mixture was stirred for 2 hr, and was then cooled to room temperature. The mixture was adjusted to pH 8 by the addition of 1 N hydrochloric acid, and then concentrated under the reduced pressure. The residue was purified by Sephadex LH-20 (development system: methanol) to prepare 12 mg of the title compound.

Physicochemical Properties of Compound Prepared in Example 43

(1) Color and form: Colorless solid
(2) Molecular formula: $C_{23}H_{34}N_6O_5$
(3) Mass spectrum (FABMS): m/z 475 (M+H)$^+$
(4) Specific rotation: $[\alpha]_D^{25}$+5.7° (c 0.58, MeOH)
(5) $^1$H NMR spectrum (400 MHz, CD$_3$OD) δ (ppm): 1.40 (9H, s, t-Bu), 1.97 (2H, quintet, tetrahydropyrimidine), 3.41 (8H, m, piperazine and tetrahydropyrimidine), 3.54 (4H, m, piperazine), 3.67 (2H, m, CONHC$\underline{H}_2$CH), 4.20 (1H, m, CONHCH$_2$C$\underline{H}$), 6.95 (2H, d, C$_6$H$_4$), 7.74 (2H, d, C$_6$H$_4$)

Example 44 t-Butyl 2-(benzenesulfonyl-methyl-amino)-3-[4-{4-(pyrimidin-2-yl)-piperazin-1-yl}-benzoylamino]-propionate The compound (40 mg) prepared in Example 1 was dissolved in 0.8 ml of dimethylformamide. Methyl iodide (50 mg) and 65 mg of 1,8-diazabicyclo[5.4.0]-7-undecene were added to the solution. A reaction was allowed to proceed at room temperature for 16 hr. The reaction solution was concentrated under the reduced pressure. The residue was extracted with 8.0 ml of ethyl acetate, followed by washing with water and saturated saline in that order. The ethyl acetate layer was dried, and then concentrated under the reduced pressure. The residue was purified by preparative thin-layer chromatography on silica gel (development system: chloroform-methanol-concentrated aqueous ammonia=200:10:1) to prepare 41 mg of the title compound.

Physicochemical Properties of Compound Prepared in Example 44

(1) Color and form: Colorless solid
(2) Molecular formula: $C_{29}H_{36}N_6O_5S$
(3) Mass spectrum (TSPMS): m/z 581 (M+H)$^+$
(4) $^1$H NMR spectrum (400 MHz, CDCl$_3$) δ (ppm): 1.30 (9H, s, t-Bu), 2.89 (3H, s, NMe), 3.39 (4H, m, piperazine), 3.76 (1H, ddd, CONHC$\underline{H}_2$CH), 3.88 (1H, ddd, CONHC$\underline{H}_2$CH), 3.99 (4H, m, piperazine), 4.73 (1H, dd, CONHCH$_2$C$\underline{H}$), 6.54 (1H, t, pyrimidine), 6.95 (2H, d, C$_6$H$_4$), 7.50 (2H, m, C$_6$H$_5$), 7.57 (1H, m, C$_6$H$_5$), 7.77 (2H, d, C$_6$H$_4$), 7.87 (2H, m, C$_6$H$_5$), 8.34 (2H, d, pyrimidine)

Example 45

2-(Benzenesulfonyl-methyl-amino)-3-[4-{4-(pyrimidin-2-yl)-piperazin-1-yl}-benzoylamino]-propionic Acid Methylene chloride (0.40 ml) and 20 1 of anisole were added to 41 mg of the compound prepared in Example 44 to prepare a solution. The solution was cooled to 0° C. Trifluoroacetic acid (0.40 ml) was added to the cooled solution, and a reaction was allowed to proceed at 0° C. for 16 hr. The reaction solution was concentrated under the reduced pressure. The residue was subjected to azeotropic distillation twice each with 2.0 ml of toluene, followed by washing twice each with 2.0 ml of diisopropyl ether and purification by preparative thin-layer chromatography on silica gel (development system: methylene chloride-methanol=6:1) to prepare 25 mg of the title compound.

Physicochemical Properties of Compound Prepared in Example 45

(1) Color and form: Colorless solid
(2) Molecular formula: $C_{25}H_{28}N_6O_5S$
(3) Mass spectrum (TSPMS): m/z 525 (M+H)$^+$
(4) $^1$H NMR spectrum (400 MHz, CD$_3$OD) δ (ppm): 2.90 (3H, s, NMe), 3.39 (4H, m, piperazine), 3.71 (1H, dd, CONHC$\underline{H}_2$CH), 3.79 (1H, dd, CONHC$\underline{H}_2$CH), 3.96 (4H, m, piperazine), 6.61 (1H, t, pyrimidine), 7.01 (2H, d, C$_6$H$_4$), 7.38 (2H, m, C$_6$H$_5$), 7.46 (1H, m, C$_6$H$_5$), 7.70 (2H, d, C$_6$H$_4$), 7.81 (2H, m, C$_6$H$_5$), 8.35 (2H, d, pyrimidine)

Example 46

2-(Benzenesulfonyl-methyl-amino)-3-[4-{4-(1,4,5,6-tetrahydropyrimidin-2-yl)-piperazin-1-yl}-benzoylamino]-propionic Acid Acetic acid (2.5 ml) and 0.23 ml of concentrated hydrochloric acid were added to 24 mg of the compound prepared in Example 45 to prepare a solution, and 23 mg of 10% palladium-carbon was added to the solution. The mixture was catalytically reduced at room temperature for 3 hr under a hydrogen pressure of 3 atm while vigorous shaking. The insolubles were collected by filtration, and then washed twice each with 1.0 ml of acetic acid. The filtrate was combined with the washings, followed by concentration under the reduced pressure. The residue was subjected to azeotropic distillation twice each with 2.0 ml of toluene. Thereafter, purification was carried out by preparative thin-layer chromatography on silica gel (development system: methylene chloride-ethanol-water-concentrated aqueous ammonia=8:8:1:1) and then by Sephadex LH-20 chromatography (development system: methanol) to prepare 13 mg of the title compound.

Physicochemical Properties of Compound Prepared in Example 46

(1) Color and form: Colorless solid
(2) Molecular formula: $C_{25}H_{32}N_6O_5S$
(3) Mass spectrum (TSPMS): m/z 529 (M+H)$^+$
(4) $^1$H NMR spectrum (400 MHz, CD$_3$OD) δ (ppm): 1.96 (2H, quintet, tetrahydropyrimidine), 2.89 (3H, s, NMe), 3.38–3.43 (8H, m, tetrahydropyrimidine and piperazine), 3.56 (4H, m, piperazine), 3.72 (2H, d, CONHC$\underline{H}_2$CH), 4.72 (1H, t, CONHCH$_2$C$\underline{H}$), 6.95 (2H, d, C$_6$H$_4$), 7.38 (2H, m, C$_6$H$_5$), 7.46 (1H, m, C$_6$H$_5$), 7.70 (2H, d, C$_6$H$_4$), 7.85 (2H, m, C$_6$H$_5$)

Example 47 t-Butyl 2-(benzenesulfonyl-hexyl-amino)-3-[4-{4-(pyrimidin-2-yl)-piperazin-1-yl}-benzoylamino]-propionate The compound (80 mg) prepared in Example 1 was dissolved in 1.6 ml of dimethylformamide. Hexyl bromide (117 mg) and 129 mg of 1,8-diazabicyclo[5.4.0]-7-undecene were added to the solution. A reaction was allowed to proceed at room temperature for 16 hr. The reaction solution was concentrated under the reduced pressure. The residue was extracted with 20 ml of ethyl acetate, followed by washing with water and saturated saline in that order. The ethyl acetate layer was dried, and then concentrated under the reduced pressure. The residue was purified by preparative thin-layer chromatography on silica gel (development system: chloroform-methanol-concentrated aqueous ammonia=200:10:1) to prepare 79 mg of the title compound.
Physicochemical Properties of Compound Prepared in Example 47

(1) Color and form: Colorless solid
(2) Molecular formula: $C_{34}H_{46}N_6O_5S$
(3) Mass spectrum (TSPMS): m/z 651 (M+H)$^+$
(4) $^1$H NMR spectrum (400 MHz, CDCl$_3$) δ (ppm): 0.82 (3H, t, hexyl), 1.15–1.76 (8H, m, hexyl), 1.35 (9H, s, t-Bu), 3.11 (1H, ddd, hexyl), 3.33 (1H, ddd, hexyl), 3.39 (4H, m, piperazine), 3.75 (1H, ddd, CONHC$\underline{H}_2$CH), 3.97 (1H, ddd, CONHC$\underline{H}_2$CH), 3.99 (4H, m, piperazine), 4.48 (1H, dd, CONHCH$_2$C$\underline{H}$), 6.54 (1H, t, pyrimidine), 6.95 (2H, d, C$_6$H$_4$), 7.51 (2H, m, C$_6$H$_5$), 7.58 (1H, m, C$_6$H$_5$), 7.75 (2H, d, C$_6$H$_4$), 7.91 (2H, m, C$_6$H$_5$), 8.34 (2H, d, pyrimidine)

Example 48

2-(Benzenesulfonyl-hexyl-amino)-3-[4-{4-(pyrimidin-2-yl)-piperazin-1-yl}-benzoylamino]-propionic Acid Methylene chloride (1.0 ml) and 50 1 of anisole were added to 79 mg of the compound prepared in Example 47 to prepare a solution which was then cooled to 0° C. Trifluoroacetic acid (1.0 ml) was added to the cooled solution, and a reaction was allowed to proceed at 0° C. for 16 hr. The reaction solution was concentrated under the reduced pressure. The residue was subjected to azeotropic distillation twice each with 5.0 ml of toluene, followed by washing twice each with 5.0 ml of diisopropyl ether and purification by preparative thin-layer chromatography on silica gel (development system: methylene chloride-methanol=6:1) to prepare 47 mg of the title compound.
Physicochemical Properties of Compound Prepared in Example 48

(1) Color and form: Colorless solid
(2) Molecular formula: $C_{30}H_{38}N_6O_5S$
(3) Mass spectrum (TSPMS): m/z 595 (M+H)$^+$
(4) $^1$H NMR spectrum (400 MHz, CDCl$_3$) δ (ppm): 0.69 (3H, t, hexyl), 0.89–1.54 (8H, m, hexyl), 3.10 (1H, m, hexyl), 3.25 (4H, m, piperazine), 3.30 (1H, m, hexyl), 3.79 (1H, m, CONHC$\underline{H}_2$CH), 3.91 (4H, m, piperazine), 3.97 (1H, m, CONHC$\underline{H}_2$CH), 4.46 (1H, m, CONHCH$_2$C$\underline{H}$), 6.51 (1H, t, pyrimidine), 6.77 (2H, d, C$_6$H$_4$), 7.32 (2H, m, C$_6$H$_5$), 7.39 (1H, m, C$_6$H$_5$), 7.68 (2H, d, C$_6$H$_4$), 7.85 (2H, m, C$_6$H$_5$), 8.32 (2H, d, pyrimidine)

Example 49

2-(Benzenesulfonyl-hexyl-amino)-3-[4-{4-(1,4,5,6-tetrahydropyrimidin-2-yl)-piperazin-1-yl}-benzoylamino]-propionic Acid Acetic acid (4.0 ml) and 0.36 ml of concentrated hydrochloric acid were added to 40 mg of the compound prepared in Example 48 to prepare a solution. 10% palladium-carbon (36 mg) was added to the solution, and the mixture was catalytically reduced at room temperature for 3 hr while vigorous shaking under a hydrogen pressure of 3 atm. The insolubles were collected by filtration, and washed twice each with 2.0 ml of acetic acid. The filtrate was combined with the washings, followed by concentration under the reduced pressure. The residue was subjected to azeotropic distillation twice each with 4.0 ml of toluene, followed by purification by preparative thin-layer chromatography on silica gel (development system: methylene chloride-ethanol-water-concentrated aqueous ammonia=8:8:1:1) and then by Sephadex LH-20 chromatography (development system: methanol) to prepare 30 mg of the title compound.
Physicochemical Properties of Compound Prepared in Example 49

(1) Color and form: Colorless solid
(2) Molecular formula: $C_{30}H_{42}N_6O_5S$
(3) Mass spectrum (TSPMS): m/z 599 (M+H)$^+$
(4) $^1$H NMR spectrum (400 MHz, CD$_3$OD) δ (ppm): 0.79 (3H, t, hexyl), 1.10–1.70 (8H, m, hexyl), 1.89 (2H, quintet, tetrahydropyrimidine), 3.23 (2H, m, hexyl), 3.30 (4H, m, piperazine), 3.35 (4H, t, tetrahydropyrimidine), 3.47 (4H, m, piperazine), 3.65 (1H,dd, CONHC$\underline{H}_2$CH), 3.71 (1H, dd, CONHC$\underline{H}_2$CH), 4.54 (1H, dd, CONHCH$_2$C$\underline{H}$), 6.85 (2H, d, C$_6$H$_4$), 7.43 (2H, m, C$_6$H$_5$), 7.50 (1H, m, C$_6$H$_5$), 7.68 (2H, d, C$_6$H$_4$), 7.92 (2H, m, C$_6$H$_5$)

Example 50

(2S)-(3-Hydroxycarbamoyl-propionylamino)-3-[4-{4-(1,4,5,6-tetrahydropyrimidin-2-yl)-piperazin-1-yl}-benzoylamino]-propionic Acid Tetrahydrofuran (30 ml) was added to 888 mg of N-hydroxysuccinimide to prepare a solution, and 8.2 g of sodium carbonate was added to and suspended in the solution. 1-Butanesulfonyl chloride (1.0 ml) was added to the suspension, and the mixture was stirred for 2 hr. Chloroform (100 ml) and 100 ml of water were added thereto. The organic layer was separated, washed with water, dried over anhydrous sodium sulfate, and concentrated under the reduced pressure to prepare 1.2 g of N-(n-butanesulfonyloxy)-succinimide as a colorless solid. Separately, water (2.0 ml) and 2.0 ml of 1,4-dioxane were added to 15 mg of the compound prepared in Example 29 to prepare a solution, and 11 mg of potassium carbonate was added to and suspended in the solution. N-(n-butanesulfonyloxy)-succinimide (21 mg) was added to the suspension, and the mixture was stirred for 8 hr. The mixture was then concentrated under the reduced pressure, and the residue was purified by preparative thin-layer chromatography on silica gel (development system: ethanol-water-concentrated aqueous ammonia=4:1:1), and then purified by Sephadex LH-20 (development system: methanol-concentrated aqueous ammonia=9:1) to prepare 12 mg of the title compound.
Physicochemical Properties of Compound Prepared in Example 50

(1) Color and form: Colorless solid
(2) Molecular formula: $C_{22}H_{31}N_7O_6$
(3) Mass spectrum (FABMS): m/z 490 (M+H)$^+$
(4) $^1$H NMR spectrum (400 MHz, D$_2$O) δ (ppm): 1.75 (2H, quintet, tetrahydropyrimidine), 2.08 (2H, t, COC$\underline{H}_2$CH$_2$CO or COCH$_2$C$\underline{H}_2$CO), 3.08 (2H, t, COC$\underline{H}_2$CH$_2$CO or COCH$_2$C$\underline{H}_2$CO), 3.19 (8H, m, piperazine and tetrahydropyrimidine), 3.31 (4H, m, piperazine), 3.39 (1H, m, CONHC$\underline{H}_2$CH), 3.57 (1H, m, CONHC$\underline{H}_2$CH), 4.17 (1H, m, CONHCH$_2$C$\underline{H}$), 6.84 (2H, d, C$_6$H$_4$), 7.51 (2H, d, C$_6$H$_4$)

Intermediate 25: Methyl 3-fluoro-4-(piperazin-1-yl)-benzoate

Dimethyl sulfoxide (1.0 ml) was added to 344 mg of piperazine to prepare a suspension, and 367 mg of methyl 3,4-difluorobenzoate was added to the suspension. The mixture was stirred at 80° C. for 4.5 hr. The temperature of the system was then returned to room temperature. The reaction solution was concentrated under the reduced pressure. The residue was purified by column chromatography on silica gel (development system: methylene chloride-methanol-concentrated aqueous ammonia=900:100:1) to prepare 392 mg of the title compound.

Physicochemical Properties of Intermediate 25
(1) Color and form: Colorless solid
(2) Molecular formula: $C_{12}H_{15}N_2O_2F$
(3) Mass spectrum (EIMS): m/z 238
(4) $^1$H NMR spectrum (400 MHz, CDCl$_3$) δ (ppm): 3.05 (4H, m, piperazine), 3.17 (4H, m, piperazine), 3.88 (3H, s, CH$_3$), 6.91 (1H, t, C$_6$H$_3$), 7.67 (1H, dd, C$_6$H$_3$), 7.75 (1H, dd, C$_6$H$_3$)

Intermediate 26: Methyl 3-fluoro-4-{4-(pyrimidin-2-yl)-piperazin-1-yl}-benzoate

Dimethylformamide (4.0 ml) was added to 199 mg of intermediate 25 to prepare a solution, and 165 mg of 2-bromopyrimidine was added to the solution. Diisopropylethylamine (0.30 ml) was added thereto. The mixture was stirred at 80° C. for 24 hr and was then cooled to room temperature, followed by concentration under the reduced pressure. The residue was purified by column chromatography on silica gel (development system: hexane-ethyl acetate=1:2) to prepare 184 mg of the title compound.

Physicochemical Properties of Intermediate 26
(1) Color and form: Colorless solid
(2) Molecular formula: $C_{16}H_{17}N_4O_2F$
(3) Mass spectrum (TSPMS): m/z 317 (M+H)$^+$
(4) $^1$H NMR spectrum (400 MHz, CDCl$_3$) δ (ppm): 3.27 (4H, m, piperazine), 3.89 (3H, s, CH$_3$), 4.00 (4H, m, piperazine), 6.54 (1H, t, pyrimidine), 6.94 (1H, t, C$_6$H$_3$), 7.70 (1H, dd, C$_6$H$_3$), 7.77 (1H, dd, C$_6$H$_3$), 8.36 (2H, d, pyrimidine)

Intermediate 27: 3-Fluoro-4-{4-(pyrimidin-2-yl)-piperazin-1-yl}-benzoic Acid

Methanol (5.0 ml) and 15 ml of tetrahydrofuran were added to 183 mg of intermediate 26 to prepare a solution, and 10 ml of a 1 N aqueous sodium hydroxide solution was added to the solution. The mixture was stirred at 50° C. for 1.5 hr and was then cooled to room temperature. The mixture was adjusted to pH 6 to 8 by the addition of 1 N hydrochloric acid. Ethyl acetate (600 ml) and 300 ml of water were added thereto. The organic layer was then separated, dried over anhydrous magnesium sulfate, and concentrated under the reduced pressure to prepare 150 mg of the title compound.

Physicochemical Properties of Intermediate 27
(1) Color and form: Colorless solid
(2) Molecular formula: $C_{15}H_{15}N_4O_2F$
(3) Mass spectrum (TSPMS): m/z 303 (M+H)$^+$
(4) $^1$H NMR spectrum (400 MHz, CD$_3$OD) δ (ppm): 3.26 (4H, m, piperazine), 3.97 (4H, m, piperazine), 6.62 (1H, t, pyrimidine), 7.10 (1H, t, C$_6$H$_3$), 7.65 (1H, dd, C$_6$H$_3$), 7.77 (1H, dd, C$_6$H$_3$), 8.35 (2H, d, pyrimidine)

Example 51 t-Butyl (2S)-benzenesulfonylamino-3-[3-fluoro-4-{4-(pyrimidin-2-yl)-piperazin-1-yl}-benzoylamino]-propionate Dimethylformamide (30 ml) was added to 148 mg of intermediate 27 to prepare a solution. t-Butyl (2S)-benzenesulfonyl-2,3-diaminopropionate (144 mg) was added to the solution. Further, 98 mg of 1-hydroxybenzotriazole, 0.30 ml of N-methylmorpholine, and 194 mg of 1-ethyl-3-(3-dimethylaminopropyl) carbodiimide hydrochloride were added thereto, and the mixture was stirred at room temperature for 8.0 hr. A saturated aqueous sodium hydrogencarbonate solution (50 ml) was added to stop the reaction, and 500 ml of methylene chloride and 200 ml of water were added thereto. The organic layer was separated, dried over anhydrous magnesium sulfate, and concentrated under the reduced pressure. The residue was purified by column chromatography on silica gel (development system: hexane-ethyl acetate=1:2) to prepare 218 mg of the title compound.

Physicochemical Properties of Compound Prepared in Example 51
(1) Color and form: Colorless solid
(2) Molecular formula: $C_{28}H_{33}N_6O_5SF$
(3) Mass spectrum (TSPMS): m/z 585 (M+H)$^+$
(4) $^1$H NMR spectrum (400 MHz, CDCl$_3$) δ (ppm): 1.29 (9H, s, t-Bu), 3.23 (4H, br t, piperazine), 3.54 (1H, m, CONHC$\underline{H}_2$CH), 3.90 (2H, m, CONHC$\underline{H}_2$C$\underline{H}$), 4.01 (4H, br t, piperazine), 6.53 (1H, t, pyrimidine), 6.95 (1H, t, C$_6$H$_3$), 7.53 (5H, m, C$_6$H$_3$ and C$_6$H$_5$), 7.85 (2H, m, C$_6$H$_5$), 8.33 (2H, d, pyrimidine)

Example 52

(2S)-Benzenesulfonylamino-3-[3-fluoro-4-{4-(pyrimidin-2-yl)-piperazin-1-yl}-benzoylamino]-propionic Acid Methylene chloride (10 ml) was added to 212 mg of the compound prepared in Example 51 to prepare a solution. Trifluoroacetic acid (3.0 ml) was added at room temperature to the solution. The mixture was stirred at that temperature for 7 hr before the reaction solution was concentrated under the reduced pressure to prepare 258 mg of tritrifluoroacetate of the title compound.

Physicochemical Properties of Compound Prepared in Example 52
(1) Color and form: pale yellow solid
(2) Molecular formula: $C_{24}H_{25}N_6O_5SF$
(3) Mass spectrum (TSPMS): m/z 529 (M+H)$^+$
(4) Specific rotation: $[\alpha]_D^{25}$+27° (c 1.0, MeOH)(as tritrifluoroacetate)
(5) $^1$H NMR spectrum (400 MHz, CD$_3$OD)(as tritrifluoroacetate) δ (ppm): 3.28 (4H, m, piperazine), 3.47 (1H, dd, CONHC$\underline{H}_2$CH), 3.71 (1H, dd, CONHC$\underline{H}_2$CH), 4.00 (4H, br t, piperazine), 4.18 (1H, dd, CONHCH$_2$C$\underline{H}$), 6.77 (1H, t, pyrimidine), 7.09 (1H, t, C$_6$H$_3$), 7.45 (4H, m, C$_6$H$_3$ and C$_6$H$_5$), 7.53 (1H, dd, C$_6$H$_3$), 7.81 (2H, m, C$_6$H$_5$), 8.43 (2H, d, pyrimidine)

Example 53

(2S)-Benzenesulfonylamino-3-[3-fluoro-4-{4-(1,4,5,6-tetrahydropyrimidin-2-yl)-piperazin-1-yl}-benzoylamino]-propionic Acid Acetic acid (50 ml) and 5.0 ml of concentrated hydrochloric acid were added to 106 mg of the compound prepared in Example 52 to prepare a solution. 10% palladium-carbon (52 mg) was added to the solution, and the mixture was vigorously shaken at room temperature for 3.5 hr under a hydrogen pressure of 3 atm. The insolubles were collected by filtration, and then washed twice with water. The filtrate was combined with the washings, followed by concentration under the reduced pressure. The residue was purified by column chromatography on silica gel (development system: methylene chloride-ethanol-water-concentrated aqueous ammonia=8:8:1:1), and then purified by Sephadex LH-20 (development system: methanol) to prepare 44 mg of the title compound.

Physicochemical Properties of Compound Prepared in Example 53
  (1) Color and form: Colorless solid
  (2) Molecular formula: $C_{24}H_{29}N_6O_5SF$
  (3) Mass spectrum (FABMS): m/z 533 (M+H)$^+$
  (4) Specific rotation: $[\alpha]_D^{25}$+24° (c 1.0, MeOH)
  (5) $^1$H NMR spectrum (400 MHz, CD$_3$OD) δ (ppm): 1.97 (2H, quintet, tetrahydropyrimidine), 3.25 (4H, br t, piperazine), 3.42 (4H, br t, tetrahydropyrimidine), 3.55 (5H, m, piperazine and CONHC$\underline{H}_2$CH), 3.67 (1H, dd, CONHC$\underline{H}_2$CH), 3.77 (1H, dd, CONHCH$_2$C$\underline{H}$), 7.08 (1H, t, C$_6$H$_3$), 7.49 (3H, m, C$_6$H$_5$), 7.55 (1H, dd, C$_6$H$_3$), 7.60 (1H, dd, C$_6$H$_3$), 7.86 (2H, m, C$_6$H$_5$)

Intermediate 28: Methyl 2-fluoro-4-(piperazin-1-yl)-benzoate

Dimethyl sulfoxide (1.0 ml) was added to 544 mg of piperazine to prepare a suspension, and 368 mg of methyl 2,4-difluorobenzoate was added to the suspension. The mixture was stirred at 80° C. for 1 hr and was then cooled to room temperature. The reaction solution was concentrated under the reduced pressure. The residue was purified by column chromatography on silica gel (development system: methylene chloride-methanol-concentrated aqueous ammonia=900:100:1) to prepare 274 mg of the title compound.

Physicochemical Properties of Intermediate 28
  (1) Color and form: Colorless solid
  (2) Molecular formula: $C_{12}H_{15}N_2O_2F$
  (3) Mass spectrum (EIMS): m/z 238
  (4) $^1$H NMR spectrum (400 MHz, CDCl$_3$) δ (ppm): 3.00 (4H, m, piperazine), 3.29 (4H, m, piperazine), 3.88 (3H, s, CH$_3$), 6.51 (1H, dd, C$_6$H$_3$), 6.63 (1H, dd, C$_6$H$_3$), 7.82 (1H, t, C$_6$H$_3$)

Intermediate 29: Methyl 2-fluoro-4-{4-(pyrimidin-2-yl)-piperazin-1-yl}-benzoate Dimethylformamide (4.0 ml) was added to 179 mg of intermediate 28 to prepare a solution, and 157 mg of 2-bromopyrimidine was added to the solution. Diisopropylethylamine (0.40 ml) was added thereto. The mixture was stirred at 60° C. for 8.0 hr and was then cooled to room temperature, followed by concentration under the reduced pressure. The residue was purified by column chromatography on silica gel (development system: hexane-ethyl acetate=1:2) to prepare 120 mg of the title compound.

Physicochemical properties of intermediate 29
  (1) Color and form: Colorless solid
  (2) Molecular formula: $C_{16}H_{17}N_4O_2F$
  (3) Mass spectrum (TSPMS): m/z 317 (M+H)$^+$
  (4) $^1$H NMR spectrum (400 MHz, CDCl$_3$) δ (ppm): 3.44 (4H, br t, piperazine), 3.91 (3H, s, CH$_3$), 3.98 (4H, br t, piperazine), 6.55 (1H, dd, C$_6$H$_3$), 6.55 (1H, t, pyrimidine), 6.66 (1H, dd, C$_6$H$_3$), 7.85 (1H, t, C$_6$H$_3$), 8.35 (2H, d, pyrimidine)

Intermediate 30: 2-Fluoro-4-{4-(pyrimidin-2-yl)-piperazin-1-yl}-benzoic Acid Methanol (4.0 ml) and 12 ml of tetrahydrofuran were added to 118 mg of intermediate 29 to prepare a solution, and 10 ml of a 1 N aqueous sodium hydroxide solution was added to the solution. The mixture was stirred at 50° C. for 2.0 hr and was then cooled to room temperature, followed by adjustment to pH 6 by the addition of 1 N hydrochloric acid. Ethyl acetate (600 ml) and 200 ml of water were added thereto. The organic layer was then separated, dried over anhydrous magnesium sulfate, and concentrated under the reduced pressure to prepare 60 mg of the title compound.

Physicochemical Properties of Intermediate 30
  (1) Color and form: Colorless solid
  (2) Molecular formula: $C_{15}H_{15}N_4O_2F$
  (3) Mass spectrum (TSPMS): m/z 303 (M+H)$^+$
  (4) $^1$H NMR spectrum (400 MHz, CD$_3$OD) δ (ppm): 3.47 (4H, m, piperazine), 4.11 (4H, m, piperazine), 6.62 (1H, t, pyrimidine), 6.69 (1H, dd, C$_6$H$_3$), 6.80 (1H, dd, C$_6$H$_3$), 7.81 (1H, t, C$_6$H$_3$), 8.35 (2H, d, pyrimidine)

Example 54 t-Butyl (2S)-benzenesulfonylamino-3-[2-fluoro-4-{4-(pyrimidin-2-yl)-piperazin-1-yl}-benzoylamino]-propionate Dimethylformamide (10 ml) was added to 58 mg of intermediate 30 to prepare a solution, and 56 mg of t-butyl (2S)-benzenesulfonyl-2,3-diaminopropionate was added to the solution. Further, 40 mg of 1-hydroxybenzotriazole, 0.10 ml of N-methylmorpholine, and 80 mg of 1-ethyl-3-(3-dimethylaminopropyl)carbodiimide hydrochloride were added thereto. The mixture was stirred at room temperature for 15 hr. A saturated aqueous sodium hydrogencarbonate solution (50 ml) was added to stop the reaction, and 600 ml of methylene chloride and 200 ml of water were added thereto. The organic layer was then separated, dried over anhydrous magnesium sulfate, and concentrated under the reduced pressure. The residue was purified by column chromatography on silica gel (development system: hexane-ethyl acetate=1:2) to prepare 64 mg of the title compound.

Physicochemical properties of compound prepared in Example 54
  (1) Color and form: Colorless solid
  (2) Molecular formula: $C_{28}H_{33}N_6O_5SF$
  (3) Mass spectrum (FABMS): m/z 585 (M+H)$^+$
  (4) Specific rotation: $[\alpha]_D^{25}$+40° (c 1.0, CH$_2$Cl$_2$)
  (5) $^1$H NMR spectrum (400 MHz, CDCl$_3$) δ (ppm): 1.29 (9H, s, t-Bu), 3.42 (4H, br t, piperazine), 3.70 (1H, m, CONHC$\underline{H}_2$CH), 3.77 (1H, m, CONHC$\underline{H}_2$CH), 4.11 (5H, m, piperazine and CONHCH$_2$C$\underline{H}$), 6.54 (1H, dd, C$_6$H$_3$), 6.55 (1H, t, pyrimidine), 6.74 (1H, dd, C$_6$H$_3$), 7.45 (2H, m, C$_6$H$_5$), 7.52 (1H, m, C$_6$H$_5$), 7.83 (2H, m, C$_6$H$_5$), 7.95 (1H, t, C$_6$H$_3$), 8.35 (2H, d, pyrimidine)

Example 55

(2S)-Benzenesulfonylamino-3-[2-fluoro-4-{4-(pyrimidin-2-yl)-piperazin-1-yl}-benzoylamino]-propionic Acid Methylene chloride (3.0 ml) was added to 61 mg of the compound prepared in Example 54 to prepare a solution. Trifluoroacetic acid (1.0 ml) was added at room temperature to the solution. The mixture was stirred at that temperature for 2.5 hr before the reaction solution was concentrated under the reduced pressure to prepare 69 mg of tritrifluoroacetate of the title compound.

Physicochemical Properties of Compound Prepared in Example 55
(1) Color and form: pale yellow solid
(2) Molecular formula: $C_{24}H_{25}N_6O_5SF$
(3) Mass spectrum (TSPMS): m/z 529 (M+H)$^+$
(4) Specific rotation: $[\alpha]_D^{25}$+28° (c 1.0, MeOH)(as tritrifluoroacetate)
(5) $^1$H NMR spectrum (400 MHz, CD$_3$OD)(as tritrifluoroacetate) δ (ppm): 3.46 (1H, dd, CONHCH$_2$CH), 3.50 (4H, br t, piperazine), 3.77 (1H, dd, CONHCH$_2$CH), 3.99 (4H, br t, piperazine), 4.17 (1H, dd, CONHCH$_2$CH), 6.71 (1H, dd, C$_6$H$_3$), 6.73 (1H, t, pyrimidine), 6.84 (1H, dd, C$_6$H$_3$), 7.44 (3H, m, C$_6$H$_5$), 7.70 (1H, t, C$_6$H$_3$), 7.82 (2H, m, C$_6$H$_5$), 8.43 (2H, d, pyrimidine)

Example 56

(2S)-Benzenesulfonylamino-3-[2-fluoro-4-{4-(1,4,5,6-tetrahydropyrimidin-2-yl)-piperazin-1-yl}-benzoylamino]-propionic Acid Acetic acid (20 ml) and 2.0 ml of concentrated hydrochloric acid were added to 41 mg of the compound prepared in Example 55 to prepare a solution. 10% palladium-carbon (21 mg) was added to the solution, and the mixture was vigorously shaken at room temperature for 3.5 hr under a hydrogen pressure of 3 atm. The insolubles were collected by filtration, and then washed twice with water. The filtrate was combined with the washings, followed by concentration under the reduced pressure. The residue was purified by Sephadex G-10 (development system: 0.05 N hydrochloric acid) to prepare 22 mg of trihydrochloride of the title compound.
Physicochemical Properties of Compound Prepared in Example 56
(1) Color and form: Colorless solid
(2) Molecular formula: $C_{24}H_{29}N_6O_5SF$
(3) Mass spectrum (FABMS): m/z 533 (M+H)$^+$
(4) Specific rotation: $[\alpha]_D^{25}$+29° (c 0.54, MeOH) (as trihydrochloride)
(5) $^1$H NMR spectrum (400 MHz, CD$_3$OD)(as trihydrochloride) δ (ppm): 1.97 (2H, quintet, tetrahydropyrimidine), 3.43 (5H, dd, tetrahydropyrimidine and CONHCH$_2$CH), 3.49 (4H, m, piperazine), 3.56 (4H, m, piperazine), 3.78 (1H, dd, CONHCH$_2$CH), 4.18 (1H, dd, CONHCH$_2$CH), 6.69 (1H, dd, C$_6$H$_3$), 6.80 (1H, dd, C$_6$H$_3$), 7.44 (3H, m, C$_6$H$_5$), 7.71 (1H, t, C$_6$H$_3$), 7.82 (2H, m, C$_6$H$_5$)

Intermediate 31

Methyl 3-chloro-4-(piperazin-1-yl)-benzoate

Dimethyl sulfoxide (15 ml) was added to 4.5 g of piperazine to prepare a suspension, and 1.1 g of methyl 3-chloro-4-fluorobenzoate was added to the suspension. The mixture was heated to 80° C., and was stirred for 5 hr. The mixture was then cooled to room temperature. Ethyl acetate (1,000 ml) and 500 ml of water were added thereto. The organic layer was separated, dried over anhydrous magnesium sulfate, and concentrated under the reduced pressure. The residue was purified by column chromatography on silica gel (development system: methylene chloride-methanol=5:1) to prepare 905 mg of the title compound.
Physicochemical Properties of Intermediate 31
(1) Color and form: Colorless solid
(2) Molecular formula: $C_{12}H_{15}N_2O_2Cl$
(3) Mass spectrum (TSPMS): m/z 255 (M+H)$^+$
(4) $^1$H NMR spectrum (400 MHz, CD$_3$OD) δ (ppm): 2.89 (4H, m, piperazine), 3.01 (4H, m, piperazine), 3.78 (3H, s, CH$_3$), 7.05 (1H, d, C$_6$H$_3$), 7.79 (1H, dd, C$_6$H$_3$), 7.86 (1H, d, C$_6$H$_3$)

Intermediate 32: Methyl 3-chloro-4-{4-(pyrimidin-2-yl)-piperazin-1-yl}-benzoate

Dimethylformamide (35 ml) was added to 905 mg of intermediate 31 to prepare a solution, and 688 mg of 2-bromopyrimidine was added to the solution. Diisopropylethylamine (3.5 ml) was added to the solution. The mixture was stirred at 80° C. for 5.0 hr and was then returned to room temperature. Ethyl acetate (1,500 ml) and 1,500 ml of water were added thereto. The organic layer was separated, dried over anhydrous magnesium sulfate, and concentrated under the reduced pressure to prepare 1.0 g of the title compound.
Physicochemical Properties of Intermediate 32
(1) Color and form: Colorless solid
(2) Molecular formula: $C_{16}H_{17}N_4O_2Cl$
(3) Mass spectrum (TSPMS): m/z 333 (M+H)$^+$
(4) $^1$H NMR spectrum (400 MHz, CDCl$_3$) δ (ppm): 3.20 (4H, br t, piperazine), 3.90 (3H, s, CH$_3$), 4.01 (4H, br t, piperazine), 6.53 (1H, t, pyrimidine), 7.04 (1H, d, C$_6$H$_3$), 7.90 (1H, dd, C$_6$H$_3$), 8.05 (1H, d, C$_6$H$_3$), 8.34 (2H, d, pyrimidine)

Intermediate 33: 3-Chloro-4-{4-(pyrimidin-2-yl)-piperazin-1-yl}-benzoic Acid

Methanol (6.0 ml) and 18 ml of tetrahydrofuran were added to 1.0 g of intermediate 32 to prepare a solution, and 6.0 ml of a 1 N aqueous sodium hydroxide solution was added to the solution. The mixture was stirred at 60° C. for 6.0 hr and was then cooled to room temperature, followed by adjustment to pH 5 by the addition of 1 N hydrochloric acid. Ethyl acetate (600 ml) and 200 ml of water were added thereto. The organic layer was separated, dried over anhydrous magnesium sulfate, and concentrated under the reduced pressure to prepare 878 mg of the title compound.
Physicochemical Properties of Intermediate 33
(1) Color and form: Colorless solid
(2) Molecular formula: $C_{15}H_{15}N_4O_2Cl$
(3) Mass spectrum (TSPMS): m/z 319 (M+H)$^+$
(4) $^1$H NMR spectrum (400 MHz, CD$_3$OD) δ (ppm): 3.18 (4H, br t, piperazine), 3.97 (4H, br t, piperazine), 6.61 (1H, t, pyrimidine), 7.18 (1H, d, C$_6$H$_3$), 7.90 (1H, dd, C$_6$H$_3$), 7.98 (1H, d, C$_6$H$_3$), 8.34 (2H, d, pyrimidine)

Example 57 t-Butyl (2S)-benzenesulfonylamino-3-[3-chloro-4-{4-(pyrimidin-2-yl)-piperazin-1-yl}-benzoylamino]-propionate Dimethylformamide (70 ml) was added to 217 mg of intermediate 33 to prepare a solution, and 202 mg of t-butyl (2S)-benzenesulfonyl-2,3-diaminopropionate was added to the solution. Further, 143 mg of 1-hydroxybenzotriazole, 0.38 ml of N-methylmorpholine, and 263 mg of 1-ethyl-3-(3-dimethylaminopropyl)carbodiimide hydrochloride were added to the mixture, followed by stirring at room temperature for 17 hr. A saturated aqueous sodium hydrogencarbonate solution (100 ml) was added to stop the reaction. Ethyl acetate (1,500 ml) and 1,000 ml of water were added thereto. The organic layer was separated, dried over anhydrous magnesium sulfate, and concentrated under the reduced pressure. The residue was purified by column chromatography on silica gel (development system: hexane-ethyl acetate=2:3) to prepare 368 mg of the title compound.

Physicochemical Properties of Compound Prepared in Example 57

(1) Color and form: Colorless solid
(2) Molecular formula: $C_{28}H_{33}N_6O_5SCl$
(3) Mass spectrum (TSPMS): m/z 601 (M+H)$^+$
(4) Specific rotation: $[\alpha]_D^{25}$+58° (c 1.0, $CH_2Cl_2$)
(5) $^1$H NMR spectrum (400 MHz, $CDCl_3$) δ (ppm): 1.29 (9H, s, t-Bu), 3.18 (4H, br t, piperazine), 3.57 (1H, m, CONHC$\underline{H}_2$CH), 3.90 (2H, m, CONHC$\underline{H}_2$C$\underline{H}$), 4.02 (4H, br t, piperazine), 6.53 (1H, t, pyrimidine), 7.06 (1H, d, $C_6H_3$), 7.51 (2H, m, $C_6H_5$), 7.58 (1H, m, $C_6H_5$), 7.66 (1H, dd, $C_6H_3$), 7.86 (3H, d, $C_6H_5$ and $C_6H_3$), 8.53 (2H, d, pyrimidine)

Example 58

(2S)-Benzenesulfonylamino-3-[2-chloro-4-{4-(pyrimidin-2-yl)-piperazin-1-yl}-benzoylamino]-propionic Acid Methylene chloride (25 ml) was added to 308 mg of the compound prepared in Example 57 to prepare a solution, and 10 ml of trifluoroacetic acid was added at room temperature to the solution. The mixture was stirred at that temperature for 5 hr before the reaction solution was concentrated under the reduced pressure to prepare 340 mg of tritrifluoroacetate of the title compound.

Physicochemical Properties of Compound Prepared in Example 58

(1) Color and form: pale yellow solid
(2) Molecular formula: $C_{24}H_{25}N_6O_5SCl$
(3) Mass spectrum (TSPMS): m/z 545 (M+H)$^+$
(4) Specific rotation: $[\alpha]_D^{25}$+12° (c 0.95, MeOH)(as tritrifluoroacetate)
(5) $^1$H NMR spectrum (400 MHz, $CD_3OD$)(as tritrifluoroacetate) δ (ppm): 3.22 (4H, br t, piperazine), 3.47 (1H, dd, CONHC$\underline{H}_2$CH), 3.71 (1H, dd, CONHC$\underline{H}_2$CH), 4.00 (4H, br t, piperazine), 4.19 (1H, dd, CONHCH$_2$C$\underline{H}$), 6.74 (1H, t, pyrimidine), 7.18 (1H, d, $C_6H_3$), 7.44 (3H, m, $C_6H_5$), 7.68 (1H, dd, $C_6H_3$), 7.79 (1H, d, $C_6H_3$), 7.81 (2H, m, $C_6H_5$), 8.43 (2H, d, pyrimidine)

Example 59

(2S)-Benzenesulfonylamino-3-[3-chloro-4-{4-(1,4,5,6-tetrahydropyrimidin-2-yl)-piperazin-1-yl}-benzoylamino]-propionic Acid Acetic acid (50 ml) and 5.0 ml of concentrated hydrochloric acid were added to 99 mg of the compound prepared in Example 58 to prepare a solution, and 53 mg of 10% palladium-carbon was added to the solution. The mixture was vigorously shaken at room temperature for 4.5 hr under a hydrogen pressure of 3 atm. The insolubles were collected by filtration, and then washed twice with water. The filtrate was combined with the washings, followed by concentration under the reduced pressure. The residue was adjusted to pH 10 by the addition of aqueous ammonia, and again concentrated under the reduced pressure. The residue was purified by Sephadex LH-20 (development system: methanol) to prepare 69 mg of the title compound.

Physicochemical Properties of Compound Prepared in Example 59

(1) Color and form: Colorless solid
(2) Molecular formula: $C_{24}H_{29}N_6O_5SCl$
(3) Mass spectrum (FABMS): m/z 549 (M+H)$^+$
(4) Specific rotation: $[\alpha]_D^{25}$+66° (c 0.53, MeOH)
(5) $^1$H NMR spectrum (400 MHz, $CD_3OD$) δ (ppm): 1.97 (2H, quintet, tetrahydropyrimidine), 3.17 (4H, br t, piperazine), 3.42 (4H, br t, tetrahydropyrimidine), 3.55 (5H, dd, piperazine and CONHC$\underline{H}_2$CH), 3.70 (1H, m, CONHC$\underline{H}_2$CH), 3.76 (1H, m, CONHCH$_2$C$\underline{H}$), 7.16 (1H, d, $C_6H_3$), 7.47 (2H, m, $C_6H_5$), 7.53 (1H, m, $C_6H_5$), 7.75 (1H, dd, $C_6H_3$), 7.85 (3H, d, $C_6H_5$ and $C_6H_3$)

Intermediate 34: Methyl 2-chloro-4-(piperazin-1-yl)-benzoate

Dimethyl sulfoxide (15 ml) was added to 4.5 g of piperazine to prepare a suspension, and 3.3 g of methyl 2-chloro-4-fluorobenzoate was added to the suspension. The mixture was stirred at 80° C. for one hr. The temperature of the system was then returned to room temperature. Ethyl acetate (1,000 ml) and 500 ml of water were added thereto. The organic layer was separated, dried over anhydrous magnesium sulfate, and concentrated under the reduced pressure to prepare 3.7 g of the title compound.

Physicochemical Properties of Intermediate 34

(1) Color and form: Colorless solid
(2) Molecular formula: $C_{12}H_{15}N_2O_2Cl$
(3) Mass spectrum (TSPMS): m/z 255 (M+H)$^+$
(4) $^1$H NMR spectrum (400 MHz, $CD_3OD$) δ (ppm): 2.83 (4H, m, piperazine), 3.18 (4H, m, piperazine), 3.73 (3H, s, $CH_3$), 6.76 (1H, dd, $C_6H_3$), 6.85 (1H, d, $C_6H_3$), 7.70 (1H, d, $C_6H_3$)

Intermediate 35: Methyl 2-chloro-4-{4-(pyrimidin-2-yl)-piperazin-1-yl}-benzoate Dimethylformamide (80 ml) was added to 2.3 g of intermediate 34 to prepare a solution, and 1.8 g of 2-bromopyrimidine was added to the solution. Diisopropylethylamine (8.0 ml) was added thereto. The mixture was stirred at 80° C. for 5.0 hr and was then cooled to room temperature, followed by dropwise addition to 2,000 ml of water. The resultant precipitate was collected by filtration on a glass filter, washed with 200 ml of hexane, and dried to prepare 2.7 g of the title compound.

Physicochemical Properties of Intermediate 35

(1) Color and form: Colorless solid
(2) Molecular formula: $C_{16}H_{17}N_4O_2Cl$
(3) Mass spectrum (TSPMS): m/z 333 (M+H)$^+$
(4) $^1$H NMR spectrum (400 MHz, $CDCl_3$) δ (ppm): 3.42 (4H, br t, piperazine), 3.88 (3H, s, $CH_3$), 3.98 (4H, br t, piperazine), 6.55 (1H, t, pyrimidine), 6.77 (1H, dd, $C_6H_3$), 6.91 (1H, d, $C_6H_3$), 7.86 (1H, d, $C_6H_3$), 8.35 (2H, d, pyrimidine)

Intermediate 36: 2-Chloro-4-{4-(pyrimidin-2-yl)-piperazin-1-yl}-benzoic Acid Methanol (9.0 ml) and 27 ml of tetrahydrofuran were added to 1.5 g of intermediate 35 to prepare a solution, and 9.0 ml of a 1 N aqueous sodium hydroxide solution was added to the solution. The mixture was stirred at 60° C. for 6.0 hr and was then cooled to room temperature, followed by adjustment to pH 6 by the addition of 1 N hydrochloric acid.

The resultant precipitate was collected by filtration to prepare 1.4 g of the title compound.

Physicochemical Properties of Intermediate 36
(1) Color and form: Colorless solid
(2) Molecular formula: $C_{15}H_{15}N_4O_2Cl$
(3) Mass spectrum (TSPMS): m/z 319 (M+H)$^+$
(4) $^1$H NMR spectrum (400 MHz, DMSO-d) δ (ppm): 3.42 (4H, br t, piperazine), 3.85 (4H, br t, piperazine), 6.66 (1H, t, pyrimidine), 6.94 (1H, dd, $C_6H_3$), 6.99 (1H, d, $C_6H_3$), 7.77 (1H, d, $C_6H_3$), 8.39 (2H, d, pyrimidine)

Example 60 t-Butyl (2S)-benzenesulfonylamino-3-[2-chloro-4-{4-(pyrimidin-2-yl)-piperazin-1-yl}-benzoylamino]-propionate Dimethylformamide (70 ml) was added to 204 mg of intermediate 36 to prepare a solution, and 194 mg of t-butyl (2S)-benzenesulfonyl-2,3-diaminopropionate was added to the solution. Further, 150 mg of 1-hydroxybenzotriazole, 0.38 ml of N-methylmorpholine, and 263 mg of 1-ethyl-3-(3-dimethylaminopropyl)carbodiimide hydrochloride were added to the solution. The mixture was stirred at room temperature for 17 hr. A saturated aqueous sodium hydrogencarbonate solution (100 ml) was added to stop the reaction. Ethyl acetate (1,500 ml) and 1,000 ml of water were added thereto. The organic layer was separated, dried over anhydrous magnesium sulfate, and concentrated under the reduced pressure. The residue was purified by column chromatography on silica gel (development system: hexane-ethyl acetate=2:3) to prepare 355 mg of the title compound.

Physicochemical Properties of Compound Prepared in Example 60
(1) Color and form: Colorless solid
(2) Molecular formula: $C_{28}H_{33}N_6O_5SCl$
(3) Mass spectrum (TSPMS): m/z 601 (M+H)$^+$
(4) Specific rotation: $[α]_D^{25}$+38° (c 1.0, $CH_2Cl_2$)
(5) $^1$H NMR spectrum (400 MHz, CDCl$_3$) δ (ppm): 1.29 (9H, s, t-Bu), 3.37 (4H, br t, piperazine), 3.73 (1H, dd, CONHC$\underline{H}_2$CH), 3.81 (1H, ddd, CONHC$\underline{H}_2$CH), 3.98 (5H, m, piperazine and CONHCH$_2$C$\underline{H}$), 6.55 (1H, t, pyrimidine), 6.85 (2H, m, $C_6H_3$), 7.49 (2H, m, $C_6H_5$), 7.57 (1H, m, $C_6H_5$), 7.73 (1H, d, $C_6H_3$), 7.86 (2H, m, $C_6H_5$), 8.35 (2H, d, pyrimidine)

Example 61

(2S)-Benzenesulfonylamino-3-[2-chloro-4-{4-(pyrimidin-2-yl)-piperazin-1-yl}-benzoylamino]-propionic Acid Methylene chloride (25 ml) was added to 289 mg of the compound prepared in Example 60 to prepare a solution, and 10 ml of trifluoroacetic acid was added at room temperature to the solution. The mixture was stirred at that temperature for 6 hr before the reaction solution was concentrated under the reduced pressure to prepare 321 mg of tritrifluoroacetate of the title compound.

Physicochemical Properties of Compound Prepared in Example 61
(1) Color and form: Pale yellow solid
(2) Molecular formula: $C_{24}H_{25}N_6O_5SCl$
(3) Mass spectrum (TSPMS): m/z 545 (M+H)$^+$
(4) Specific rotation: $[α]_D^{25}$+18° (c 0.56, DMSO)(as tritrifluoroacetate)
(5) $^1$H NMR spectrum (400 MHz, CD$_3$OD)(as tritrifluoroacetate) δ (ppm): 3.41 (4H, br t, piperazine), 3.48 (1H, dd, CONHC$\underline{H}_2$CH), 3.71 (1H, dd, CONHC$\underline{H}_2$CH), 3.97 (4H, m, piperazine), 4.18 (1H, dd, CONHCH$_2$C$\underline{H}$), 6.72 (1H, t, pyrimidine), 6.94 (1H, dd, $C_6H_3$), 7.00 (1H, d, $C_6H_3$), 7.45 (1H, d, $C_6H_3$), 7.50 (2H, m, $C_6H_5$), 7.57 (1H, m, $C_6H_5$), 7.86 (2H, m, $C_6H_5$), 8.41 (2H, d, pyrimidine)

Example 62

(2S)-Benzenesulfonylamino-3-[2-chloro-4-{4-(1,4,5,6-tetrahydropyrimidin-2-yl)-piperazin-1-yl}-benzoylamino]-propionic Acid Acetic acid (50 ml) and 5.0 ml of concentrated hydrochloric acid were added to 103 mg of the compound prepared in Example 61 to prepare a solution, and 56 mg of 10% palladium-carbon was added to the solution. The mixture was vigorously stirred at room temperature for 3.5 hr under a hydrogen pressure of 3 atm. The insolubles were colleted by filtration, and then washed twice with water. The filtrate was combined with the washings, followed by concentration under the reduced pressure. The residue was adjusted to pH 10 by the addition of aqueous ammonia, and again concentrated under the reduced pressure. The residue was purified by Sephadex LH-20 (development system: methanol) to prepare 58 mg of the title compound.

Physicochemical Properties of Compound Prepared in Example 62
(1) Color and form: Colorless solid
(2) Molecular formula: $C_{24}H_{29}N_6O_5SCl$
(3) Mass spectrum (FABMS): m/z 549 (M+H)$^+$
(4) Specific rotation: $[α]_D^{25}$+68° (c 0.37, MeOH)
(5) $^1$H NMR spectrum (400 MHz, CD$_3$OD) δ (ppm): 1.97 (2H, quintet, tetrahydropyrimidine), 3.41 (8H, br t, piperazine and tetrahydropyrimidine), 3.54 (4H, m, piperazine), 3.59 (1H, dd, CONHC$\underline{H}_2$CH), 3.68 (1H, dd, CONHC$\underline{H}_2$CH), 3.75 (1H, dd, CONHCH$_2$C$\underline{H}$), 6.90 (1H, dd, $C_6H_3$), 6.96 (1H, d, $C_6H_3$), 7.55 (4H, d, $C_6H_5$ and $C_6H_3$), 7.87 (2H, m, $C_6H_5$)

Intermediate 37: 3-Nitro-4-{4-(pyrimidin-2-yl)-piperazin-1-yl}-benzoic Acid

Dimethyl sulfoxide (10 ml) was added to 2.3 g of 1-(2-pyrimidyl)piperazine dihydrochloride to prepare a suspension. 4-Fluoro-3-nitrobenzoic acid (1.9 g) was added to the suspension. Diisopropylethylamine (1.0 ml) was added thereto. The mixture was stirred at 120° C. for 17 hr and was then cooled to room temperature. Ethyl acetate (3,000 ml) and 1,000 ml of water were added thereto. The organic layer was separated, dried over anhydrous magnesium sulfate, and concentrated under the reduced pressure to prepare 570 mg of the title compound.

Physicochemical Properties of Intermediate 37
(1) Color and form: Yellow solid
(2) Molecular formula: $C_{15}H_{15}N_5O_4$
(3) Mass spectrum (FABMS): m/z 330 (M+H)$^+$
(4) $^1$H NMR spectrum (400 MHz, CD$_3$OD) δ (ppm): 3.27 (4H, br t, piperazine), 3.96 (4H, br t, piperazine), 6.63 (1H, t, pyrimidine), 7.32 (1H, d, $C_6H_3$), 8.11 (1H, dd, $C_6H_3$), 8.35 (2H, d, pyrimidine), 8.39 (1H, d, $C_6H_3$), Example 63 t-Butyl (2S)-benzenesulfonylamino-3-[3-nitro-4-{4-(pyrimidin-2-yl)-piperazin-1-yl}-benzoylamino]-propionate Dimethylformamide (100 ml) was added to 299 mg of intermediate 37 to prepare a solution, and 272 mg of t-butyl (2S)-benzenesulfonyl-2,3-diaminopropionate was added to the solution. Further, 199 mg of 1-hydroxybenzotriazole, 0.50 ml of N-methylmorpholine, and 352 mg of 1-ethyl-3-(3-dimethylaminopropyl)carbodiimide hydrochloride were added to the solution. The mixture was stirred at room temperature for 14 hr. A saturated aqueous sodium hydrogencarbonate solution (100 ml) was added to stop the reaction. Ethyl acetate (1,500 ml) and 1,500 ml of water were added thereto. The organic layer was separated, dried over anhydrous magnesium sulfate, and concentrated under the reduced pressure. The residue was purified by column chromatography on silica gel (development system: hexane-ethyl acetate=1:2) to prepare 493 mg of the title compound.

Physicochemical Properties of Compound Prepared in Example 63

(1) Color and form: Yellow solid
(2) Molecular formula: $C_{28}H_{33}N_7O_7S$
(3) Mass spectrum (TSPMS): m/z 612 (M+H)$^+$
(4) Specific rotation: $[\alpha]_D^{25}$+58° (c 1.0, $CH_2Cl_2$)
(5) $^1$H NMR spectrum (400 MHz, $CDCl_3$) δ (ppm): 1.30 (9H, s, t-Bu), 3.26 (4H, br t, piperazine), 3.53 (1H, m, CONHC$\underline{H}_2$CH), 3.91 (1H, m, CONHC$\underline{H}_2$CH), 3.96 (1H, d, CONHCH$_2$C$\underline{H}$), 4.01 (4H, br t, piperazine), 6.55 (1H, t, pyrimidine), 7.15 (1H, d, $C_6H_3$), 7.51 (2H, m, $C_6H_5$), 7.59 (1H, m, $C_6H_5$), 7.86 (2H, m, $C_6H_5$), 7.93 (1H, dd, $C_6H_3$), 8.31 (1H, d, $C_6H_3$), 8.34 (2H, d, pyrimidine)

Example 64

(2S)-Benzenesulfonylamino-3-[2-nitro-4-{4-(pyrimidin-2-yl)-piperazin-1-yl}-benzoylamino]-propionic Acid Methylene chloride (25 ml) was added to 233 mg of the compound prepared in Example 63 to prepare a solution, and 10 ml of trifluoroacetic acid was added at room temperature to the solution. The mixture was stirred at that temperature for 5.5 hr before the reaction solution was concentrated under the reduced pressure to prepare 259 mg of tritrifluoroacetate of the title compound.

Physicochemical Properties of Compound Prepared in Example 64

(1) Color and form: Yellow solid
(2) Molecular formula: $C_{24}H_{25}N_7O_7S$
(3) Mass spectrum (TSPMS): m/z 556 (M+H)$^+$
(4) Specific rotation: $[\alpha]_D^{25}$+25° (c 1.1, MeOH)(as tritrifluoroacetate)
(5) $^1$H NMR spectrum (400 MHz, $CD_3OD$)(as tritrifluoroacetate) δ (ppm): 3.29 (4H, br t, piperazine), 3.47 (1H, dd, CONHC$\underline{H}_2$CH), 3.73 (1H, dd, CONHC$\underline{H}_2$CH), 3.98 (4H, br t, piperazine), 4.20 (1H, d, CONHCH$_2$C$\underline{H}$), 6.72 (1H, t, pyrimidine), 7.32 (1H, d, $C_6H_3$), 7.43 (3H, m, $C_6H_5$), 7.81 (2H, m, $C_6H_5$), 7.92 (1H, dd, $C_6H_3$), 8.18 (1H, d, $C_6H_3$), 8.41 (2H, d, pyrimidine)

Example 65

3-[3-Amino-2-chloro-4-{4-(1,4,5,6-tetrahydropyrimidin-2-yl)-piperazin-1-yl}-benzoylamino]-(2S)-benzenesulfonylamino-propionic Acid Acetic acid (30 ml) and 3.0 ml of concentrated hydrochloric acid were added to 60 mg of the compound prepared in Example 64 to prepare a solution, and 31 mg of 10% palladium-carbon was added to the solution. The mixture was vigorously stirred at room temperature for 3.5 hr under a hydrogen pressure of 3 atm. The insolubles were collected by filtration, and then washed twice with water. The filtrate was combined with the washings, followed by concentration under the reduced pressure. The residue was purified by column chromatography on silica gel (development system: methylene chloride-ethanol-water-concentrated aqueous ammonia=8:8:1:1), and then purified by Sephadex LH-20 (development system: methanol) to prepare 19 mg of the title compound.

Physicochemical Properties of Compound Prepared in Example 65

(1) Color and form: Colorless solid
(2) Molecular formula: $C_{24}H_{30}N_7O_5SCl$
(3) Mass spectrum (ESIMS): m/z 564 (M+H)$^+$
(4) Specific rotation: $[\alpha]_D^{25}$+45° (c 0.52, MeOH)
(5) $^1$H NMR spectrum (400 MHz, $CD_3OD$) δ (ppm): 1.97 (2H, quintet, tetrahydropyrimidine), 2.93 (4H, m, piperazine), 3.42 (4H, br t, tetrahydropyrimidine), 3.54 (4H, m, piperazine), 3.57 (1H, dd, CONHC$\underline{H}_2$CH), 3.67 (1H, dd, CONHC$\underline{H}_2$CH), 3.78 (1H, dd, CONHCH$_2$C$\underline{H}$), 6.91 (1H, d, $C_6H_2$), 6.96 (1H, d, $C_6H_2$), 7.53 (2H, m, $C_6H_5$), 7.58 (1H, m, $C_6H_5$), 7.88 (2H, d, $C_6H_5$)

Example 66 t-Butyl (2S)-benzyloxycarbonylamino-3-[4-{(3S)-methyl-4-(pyrimidin-2-yl)-piperazin-1-yl}-benzoylamino]-propionate Dimethylformamide (6.0 ml) was added to 44 mg of intermediate 15 to prepare a solution, and 45 mg of t-butyl (2S)-benzyloxycarbonyl-2,3-diaminopropionate was added to the solution. Further, 29 mg of 1-hydroxybenzotriazole, 0.10 ml of N-methylmorpholine, and 53 mg of 1-ethyl-3-(3-dimethylaminopropyl)carbodiimide hydrochloride were added thereto. The mixture was stirred at room temperature for 24 hr. A saturated aqueous sodium hydrogencarbonate solution (50 ml) was added to stop the reaction, and 300 ml of methylene chloride was added thereto. The organic layer was separated, dried over anhydrous magnesium sulfate, and concentrated under the reduced pressure. The residue was purified by column chromatography on silica gel (development system: hexane-ethyl acetate=1:2) to prepare 66 mg of the title compound.

Physicochemical Properties of Compound Prepared in Example 66

(1) Color and form: Colorless solid
(2) Molecular formula: $C_{30}H_{38}N_6O_5$
(3) Mass spectrum (TSPMS): m/z 575 (M+H)$^+$
(4) Specific rotation: $[\alpha]_D^{25}$+24° (c 1.0, $CH_2Cl_2$)
(5) $^1$H NMR spectrum (400 MHz, $CDCl_3$) δ (ppm): 1.32 (3H, d, $CH_3$), 1.46 (9H, s, t-Bu), 3.03 (1H, dt, piperazine), 3.23 (1H, dd, piperazine), 3.47 (1H, ddd, piperazine), 3.64 (1H, br d, piperazine), 3.80 (3H, m, piperazine and CONHC$\underline{H}_2$CH), 4.45 (1H, m, CONHCH$_2$C$\underline{H}$), 4.54 (1H, dt, piperazine), 4.96 (1H, m, piperazine), 5.12 (2H, br s, C$\underline{H}_2C_6\underline{H}_5$), 6.53 (1H, t, pyrimidine), 6.79 (2H, d, $C_6H_4$), 7.33 (5H, m, $CH_2C_6H_5$), 7.68 (2H, d, $C_6H_4$), 8.35 (2d, pyrimidine)

Example 67

(2S)-Benzyloxycarbonylamino-3-[4-{(3S)-methyl-4-(pyrimidin-2-yl)-piperazin-1-yl}-benzoylamino]-propionic Acid Methylene chloride (4.0 ml) was added to 62 mg of the compound prepared in Example 66 to prepare a solution, and 2.0 ml of trifluoroacetic acid was added at room temperature to the solution. The mixture was stirred at that temperature for 3.5 hr before the reaction solution was concentrated under the reduced pressure to prepare 59 mg of tritrifluoroacetate of the title compound.

Physicochemical Properties of Compound Prepared in Example 67

(1) Color and form: Pale yellow solid
(2) Molecular formula: $C_{27}H_{30}N_6O_5$
(3) Mass spectrum (TSPMS): m/z 519 (M+H)$^+$
(4) Specific rotation: $[\alpha]_D^{25}$+24° (c 1.0, MeOH)(as tritrifluoroacetate)
(5) 1H NMR spectrum (400 MHz, $CD_3OD$)(as tritrifluoroacetate) δ (ppm): 1.32 (3H, d, $CH_3$), 3.02 (1H, dt, piperazine), 3.22 (1H, dd, piperazine), 3.50 (1H, dt, piperazine), 3.70 (1H, dd, CONH$CH_2$CH), 3.80 (2H, m, piperazine and CONH$CH_2$CH), 3.86 (1H, br d, piperazine), 4.58 (2H, m, piperazine and CONHCH$_2$C$H$), 4.90 (1H, m, piperazine), 5.07 (2H, dd, $CH_2$C$_6$H$_5$), 6.68 (1H, t, pyrimidine), 6.97 (2H, d, $C_6H_4$), 7.28 (5H, m, CH$_2$C$_6$$H_5$), 7.71 (2H, d, $C_6H_4$), 8.40 (2H, d, pyrimidine)

Example 68

(2S)-Amino-3-[4-{(3S)-methyl-4-(1,4,5,6-tetrahydropyrimidin-2-yl)-piperazin-1-yl}-benzoylamino]-propionic Acid Acetic acid (25 ml) and 2.5 ml of concentrated hydrochloric acid were added to 53 mg of the compound prepared in Example 67 to prepare a solution, and 27 mg of 10% palladium-carbon was added to the solution. The mixture was vigorously shaken at room temperature for 4 hr under a hydrogen pressure of 3 atm. The insolubles were collected by filtration, and then washed twice with water. The filtrate was combined with the washings, followed by concentration under the reduced pressure. The residue was purified by Sephadex G-10 (development system: 0.05 N hydrochloric acid) to prepare 33 mg of trihydrochloride of the title compound.

Physicochemical Properties of Compound Prepared in Example 68

(1) Color and form: Brown solid
(2) Molecular formula: $C_{19}H_{28}N_6O_3$
(3) Mass spectrum (FABMS): m/z 389 (M+H)$^+$
(4) Specific rotation: $[\alpha]_D^{25}$+7.80° (c 1.1, $H_2O$)(as trihydrochloride)
(5) $^1$H NMR spectrum (400 MHz, $CD_3OD$)(as trihydrochloride) δ (ppm): 1.34 (3H, d, $CH_3$), 1.97 (2H, quintet, tetrahydropyrimidine), 3.04 (1H, m, piperazine), 3.22 (1H, m, piperazine), 3.42 (4H, br t, tetrahydropyrimidine), 3.48 (1H, m, piperazine), 3.65 (1H, m, piperazine), 3.77 (1H, m, piperazine), 3.82 (1H, dd, CONH$CH_2$CH), 3.86 (1H, m, piperazine), 3.95 (1H, dd, CONH$CH_2$CH), 4.12 (1H, m, piperazine), 4.22 (1H, dd, CONHCH$_2$C$H$), 7.00 (2H, d, $C_6H_4$), 7.80 (2H, d, $C_6H_4$)

Example 69

(2S)-Benzyloxycarbonylamino-3-[4-{(3S)-methyl-4-(1,4,5,6-tetrahydropyrimidin-2-yl)-piperazin-1-yl}-benzoylamino]-propionic Acid Acetone (2.0 ml) and 2.0 ml of water were added to 21 mg of the compound prepared in Example 68 to prepare a solution, and 30 mg of potassium carbonate was added to the solution. Benzyloxycarbonyl chloride (0.016 ml) was added thereto, and the mixture was stirred for 30 min and concentrated under the reduced pressure. The residue was purified by Sephadex G-10(development system: 0.05 N hydrochloric acid) to prepare 4.8 mg of trihydrochloride of the title compound.

Physicochemical Properties of Compound Prepared in Example 69

(1) Color and form: Colorless solid
(2) Molecular formula: $C_{27}H_{34}N_6O_5$
(3) Mass spectrum (TSPMS): m/z 523 (M+H)$^+$
(4) Specific rotation: $[\alpha]_D^{25}$+23° (c 0.14, MeOH)(as trihydrochloride)
(5) $^1$H NMR spectrum (400 MHz, $CD_3OD$)(as trihydrochloride) δ (ppm): 1.34 (3H, d, $CH_3$), 1.97 (2H, quintet, tetrahydropyrimidine), 3.00 (1H, m, piperazine), 3.20 (1H, br d, piperazine), 3.42 (4H, br t, tetrahydropyrimidine), 3.48 (1H, m, piperazine), 3.72 (5H, m, piperazine and CONH$CH_2$CH), 4.10 (1H, m, CONHCH$_2$C$H$), 4.46 (1H, dd, piperazine), 5.07 (2H, dd, $CH_2$C$_6$H$_5$), 6.96 (2H, d, $C_6H_4$), 7.30 (5H, m, CH$_2$C$_6$$H_5$), 7.72 (2H, d, $C_6H_4$)

Intermediate 38: Methyl 3-fluoro-4-{(3S)-methyl-(piperazin-1-yl)}-benzoate

Dimethyl sulfoxide (10 ml) was added to 2.0 g of (2S)-methylpiperazine to prepare a suspension, and 1.1 g of methyl 3,4-difluorobenzoate was added to the suspension. The mixture was stirred at 80° C. for 6.5 hr and was then cooled to room temperature. Ethyl acetate and water were added thereto. The organic layer was separated, dried over anhydrous magnesium sulfate, and concentrated under the reduced pressure to prepare 807 mg of the title compound.

Physicochemical Properties of Intermediate 38

(1) Color and form: Colorless solid
(2) Molecular formula: $C_{13}H_{17}N_2O_2F$
(3) Mass spectrum (TSPMS): m/z 253 (M+H)$^+$
(4) $^1$H NMR spectrum (400 MHz, $CD_3OD$) δ (ppm): 1.12 (3H, t, $CH_3$), 2.46 (1H, dd, piperazine), 2.80 (1H, dt, piperazine), 3.00 (3H, m, piperazine), 3.46 (2H, m, piperazine), 3.86 (3H, S, $CO_2CH_3$), 7.03 (1H, t, $C_6H_3$), 7.60 (1H, dd, $C_6H_3$), 7.74 (1H, dd, $C_6H_3$)

Intermediate 39: Methyl 3-fluoro-4-{(3S)-methyl-4-(pyrimidin-2-yl)-piperazin-1-yl}-benzoate Dimethylformamide (30 ml) was added to 804 mg of intermediate 38 to prepare a solution, and 505 mg of 2-bromopyrimidine was added to the solution. Diisopropylethylamine (3.0 ml) was added thereto. The mixture was stirred at 80° C. for 24 hr and was then cooled to room temperature. Ethyl acetate (1,000 ml) and 1,500 ml of water were added thereto. The organic layer was separated, dried over anhydrous magnesium sulfate, and concentrated under the reduced pressure. The residue was purified by column chromatography on silica gel (development system: hexane-ethyl acetate=1:1) to prepare 561 mg of the title compound.

Physicochemical Properties of Intermediate 39

(1) Color and form: Colorless solid
(2) Molecular formula: $C_{17}H_{19}N_4O_2F$
(3) Mass spectrum (TSPMS): m/z 331 (M+H)$^+$
(4) $^1$H NMR spectrum (400 MHz, $CDCl_3$) δ (ppm): 1.39 (3H, t, $CH_3$), 2.94 (1H, dt, piperazine), 3.05 (1H, dd, piperazine), 3.41 (1H, ddd, piperazine), 3.55 (2H, m, piperazine), 3.89 (3H, s, $CO_2CH_3$), 4.60 (1H, br d, piperazine), 4.99 (1H, m, piperazine), 6.52 (1H, t, pyrimidine), 6.92 (1H, t, $C_6H_3$), 7.68 (1H, dd, $C_6H_3$), 7.76 (1H, dd, $C_6H_3$), 8.34 (2H, d, pyrimidine)

Intermediate 40: 3-Fluoro-4-{(3S)-methyl-4-(pyrimidin-2-yl)-piperazin-1-yl}-benzoic Acid Methanol (3.0 ml) and 9.0 ml of tetrahydrofuran were added to 554 mg of intermediate 39 to prepare a solution, and 3.0 ml of a 1 N aqueous sodium hydroxide solution was added to the solution. The mixture was stirred at 60° C. for 7.0 hr and was then cooled to room temperature, followed by adjustment to pH 4 by the addition of 1 N hydrochloric acid. Water (50 ml) was then added thereto. The resultant precipitate was collected by filtration on a glass filter, and then dissolved in 300 ml of ethyl acetate, followed by washing with 100 ml of water. The organic layer was separated, dried over anhydrous magnesium sulfate, and concentrated under the reduced pressure to prepare 413 mg of the title compound.

Physicochemical Properties of Intermediate 40
(1) Color and form: Colorless solid
(2) Molecular formula: $C_{16}H_{17}N_4O_2F$
(3) Mass spectrum (TSPMS): m/z 317 (M+H)$^+$
(4) $^1$H NMR spectrum (400 MHz, $CD_3OD$) δ (ppm): 1.36 (3H, t, $CH_3$), 2.90 (1H, dt, piperazine), 3.02 (1H, dd, piperazine), 3.38 (1H, ddd, piperazine), 3.57 (2H, m, piperazine), 4.58 (1H, br d, piperazine), 4.97 (1H, m, piperazine), 6.60 (1H, t, pyrimidine), 7.07 (1H, t, $C_6H_3$), 7.64 (1H, dd, $C_6H_3$), 7.76 (1H, dd, $C_6H_3$), 8.34 (2H, d, pyrimidine)

Example 70 t-Butyl (2S)-benzenesulfonylamino-3-[3-fluoro-4-{(3S)-methyl-4-(pyrimidin-2-yl)-piperazin-1-yl}-benzoylamino]-propionate Dimethylformamide (20 ml) was added to 52 mg of intermediate 40 to prepare a solution, and 51 mg of t-butyl (2S)-benzenesulfonyl-2,3-diaminopropionate was added to the solution. Further, 36 mg of 1-hydroxybenzotriazole, 0.20 ml of N-methylmorpholine, and 66 mg of 1-ethyl-3-(3-dimethylaminopropyl)carbodiimide hydrochloride were added thereto, and the mixture was stirred at room temperature for 16 hr. A saturated aqueous sodium hydrogencarbonate solution (50 ml) was added to stop the reaction. Ethyl acetate (900 ml) and 500 ml of water were added thereto. The organic layer was separated, dried over anhydrous magnesium sulfate, and concentrated under the reduced pressure. The residue was purified by column chromatography on silica gel (development system: hexane-ethyl acetate=1:2) to prepare 100 mg of the title compound.

Physicochemical Properties of Compound Prepared in Example 70
(1) Color and form: Colorless solid
(2) Molecular formula: $C_{29}H_{35}N_6O_5SF$
(3) Mass spectrum (ESIMS): m/z 599 (M+H)$^+$
(4) Specific rotation: $[\alpha]_D^{25}$+85° (c 0.86, $CH_2Cl_2$)
(5) $^1$H NMR spectrum (400 MHz, $CDCl_3$) δ (ppm): 1.29 (9H, s, t-Bu), 1.40 (3H, t, $CH_3$), 2.92 (1H, dt, piperazine), 3.03 (1H, dd, piperazine), 3.41 (1H, ddd, piperazine), 3.51 (3H, m, piperazine and CONHC$\underline{H}_2$CH), 3.90 (2H, m, CONHC$\underline{H}_2$C$\underline{H}$), 4.62 (1H, br d, piperazine), 4.99 (1H, m, piperazine), 6.52 (1H, t, pyrimidine), 6.97 (1H, t, $C_6H_3$), 7.56 (5H, m, $C_6H_5$ and $C_6H_3$), 7.86 (2H, m, $C_6H_5$), 8.34 (2H, d, pyrimidine)

Example 71

(2S)-Benzenesulfonylamino-3-[3-fluoro-4-{(3S)-methyl-4-(pyrimidin-2-yl)-piperazin-1-yl}-benzoylamino]-propionic Acid Methylene chloride (4.0 ml) was added to 89 mg of the compound prepared in Example 70 to prepare a solution, and 5.0 ml of trifluoroacetic acid was added at room temperature to the solution. The mixture was stirred at that temperature for 4 hr before the reaction solution was concentrated under the reduced pressure to prepare 96 mg of tritrifluoroacetate of the title compound.

Physicochemical Properties of Compound Prepared in Example 71
(1) Color and form: Pale yellow solid
(2) Molecular formula: $C_{25}H_{27}N_6O_5SF$
(3) Mass spectrum (FABMS): m/z 543 (M+H)$^+$
(4) Specific rotation: $[\alpha]_D^{25}$+50° (c 1.8, MeOH) (as tritrifluoroacetate)
(5) $^1$H NMR spectrum (400 MHz, $CD_3OD$)(as tritrifluoroacetate) δ (ppm): 1.43 (3H, t, $CH_3$), 2.95 (1H, dt, piperazine), 3.06 (1H, dd, piperazine), 3.48 (2H, m, piperazine and CONHC$\underline{H}_2$CH), 3.56 (1H, dt, piperazine), 3.61 (1H, br d, piperazine), 3.71 (1H, dd, CONHC$\underline{H}_2$CH), 4.19 (1H, dd, CONHCH$_2$C$\underline{H}$), 4.56 (1H, br d, piperazine), 4.93 (1H, m, piperazine), 6.74 (1H, t, pyrimidine), 7.07 (1H, t, $C_6H_3$), 7.47 (4H, m, $C_6H_5$ and $C_6H_3$), 7.55 (1H, dd, $C_6H_3$), 7.82 (2H, m, $C_6H_5$), 8.44 (2H, d, pyrimidine)

Example 72

(2S)-Benzenesulfonylamino-3-[3-fluoro-4-{(3S)-methyl-4-(1,4,5,6-tetrahydropyrimidin-2-yl)-piperazin-1-yl}-benzoylamino]-propionic Acid Acetic acid (30 ml) and 3.0 ml of concentrated hydrochloric acid were added to 61 mg of the compound prepared in Example 71 to prepare a solution, and 35 mg of 10% palladium-carbon was added to the solution. The mixture was vigorously shaken at room temperature for 3.5 hr under a hydrogen pressure of 3 atm. The insolubles were collected by filtration, and then washed twice with water. The filtrate was combined with the washings, followed by concentration under the reduced pressure. The residue was purified by column chromatography on silica gel (development system: methylene chloride-ethanol-water-concentrated aqueous ammonia=8:8:1:1), and then purified by Sephadex LH-20 (development system: methanol) to prepare 30 mg of the title compound.

Physicochemical Properties of Compound Prepared in Example 72
(1) Color and form: Colorless solid
(2) Molecular formula: $C_{25}H_{31}N_6O_5SF$
(3) Mass spectrum (FABMS): m/z 547 (M+H)$^+$
(4) Specific rotation: $[\alpha]_D^{25}$+53° (c 0.51, MeOH)
(5) $^1$H NMR spectrum (400 MHz, $CD_3OD$) δ (ppm): 1.44 (3H, t, $CH_3$), 1.98 (2H, quintet, tetrahydropyrimidine), 2.93 (1H, dt, piperazine), 3.04 (1H, dd, piperazine), 3.43 (4H, m, tetrahydropyrimidine), 3.55 (5H, m, piperazine and CONHC$\underline{H}_2$CH), 3.70 (1H, dd, CONHC$\underline{H}_2$CH), 3.91 (1H, dd, CONHCH$_2$C$\underline{H}$), 4.07 (1H, m, piperazine), 7.06 (1H, t, $C_6H_3$), 7.50 (4H, m, $C_6H_5$ and $C_6H_3$), 7.60 (1H, dd, $C_6H_3$), 7.85 (2H, m, $C_6H_5$)

Example 73 t-Butyl (2S)-benzyloxycarbonylamino-3-[3-fluoro-4-{4-(pyrimidin-2-yl)-piperazin-1-yl}-benzoylamino]-propionate Dimethylformamide (100 ml) was added to 302 mg of intermediate 27 to prepare a solution, and 317 mg of t-butyl (2S)-benzyloxycarbonyl-2,3-diaminopropionate was added to the solution. Further, 212 mg of 1-hydroxybenzotriazole, 0.60 ml of N-methylmorpholine, and 382 mg of 1-ethyl-3-(3-dimethylaminopropyl)carbodiimide hydrochloride were added thereto. The mixture was stirred at room temperature for 17 hr. A saturated aqueous sodium hydrogencarbonate solution (100 ml) was added to stop the reaction, and 2,000 ml of water was added thereto. The resultant precipitate was collected by filtration on a glass filter to prepare 420 mg of the title compound.

Physicochemical Properties of Compound Prepared in Example 73

(1) Color and form: Colorless solid
(2) Molecular formula: $C_{30}H_{35}N_6O_5F$
(3) Mass spectrum (TSPMS): m/z 579 (M+H)$^+$
(4) Specific rotation: $[\alpha]_D^{25}$ –12° (c 0.98, $CH_2Cl_2$)
(5) $^1$H NMR spectrum (400 MHz, $CDCl_3$) δ (ppm): 1.46 (9H, s, t-Bu), 3.22 (4H, br t, piperazine), 3.78 (2H, m, CONHC$\underline{H}_2$CH), 4.00 (4H, br t, piperazine), 4.45 (1H, m, CONHCH$_2$C$\underline{H}$), 5.12 (2H, d, C$\underline{H}_2$C$_6$H$_5$), 6.53 (1H, t, pyrimidine), 6.92 (1H, t, C$_6$H$_3$), 7.32 (5H, m, CH$_2$C$_6$$\underline{H}_5$), 7.45 (1H, d, C$_6$H$_3$), 7.50 (1H, d, C$_6$H$_3$), 8.34 (2H, d, pyrimidine)

Example 74

(2S)-Benzyloxycarbonylamino-3-[3-fluoro-4-{4-(pyrimidin-2-yl)-piperazin-1-yl}-benzoylamino]-propionic Acid Methylene chloride (5.0 ml) was added to 96 mg of the compound prepared in Example 73 to prepare a solution, and 5.0 ml of trifluoroacetic acid was added at room temperature to the solution. The mixture was stirred at that temperature for 2 hr before the reaction solution was concentrated under the reduced pressure to prepare 98 mg of tritrifluoroacetate of the title compound.

Physicochemical Properties of Compound Prepared in Example 74

(1) Color and form: pale yellow solid
(2) Molecular formula: $C_{26}H_{27}N_6O_5F$
(3) Mass spectrum (TSPMS): m/z 523 (M+H)$^+$
(4) Specific rotation: $[\alpha]_D^{25}$ –5.2° (c 0.58, DMSO)(as tritrifluoroacetate)
(5) $^1$H NMR spectrum (400 MHz, $CD_3OD$)(as tritrifluoroacetate) δ (ppm): 3.27 (4H, br t, piperazine), 3.69 (1H, dd, CONHC$\underline{H}_2$CH), 3.81 (1H, dd, CONHC$\underline{H}_2$CH), 4.00 (4H, br t, piperazine), 4.48 (1H, dd, CONHCH$_2$C$\underline{H}$), 5.07 (2H, d, C$\underline{H}_2$C$_6$H$_5$), 6.73 (1H, t, pyrimidine), 7.08 (1H, t, C$_6$H$_3$), 7.28 (5H, m, CH$_2$C$_6$$\underline{H}_5$), 7.54 (1H, dd, C$_6$H$_3$), 7.57 (1H, dd, C$_6$H$_3$), 8.43 (2H, d, pyrimidine)

Example 75

(2S)-Amino-3-[3-fluoro-4-{4-(1,4,5,6-tetrahydropyrimidin-2-yl)-piperazin-1-yl}-benzoylamino]-propionic Acid Acetic acid (40 ml) and 4.0 ml of concentrated hydrochloric acid were added to 81 mg of the compound prepared in Example 74 to prepare a solution, and 42 mg of 10% palladium-carbon was added to the solution. The mixture was vigorously shaken at room temperature for 3.5 hr under a hydrogen pressure of 3 atm. The insolubles were collected by filtration, and then washed twice with water. The filtrate was combined with the washings, followed by concentration under the reduced pressure to prepare 88 mg of trihydrochloride of the title compound.

Physicochemical Properties of Compound Prepared in Example 75

(1) Color and form: Colorless solid
(2) Molecular formula: $C_{18}H_{25}N_6O_3F$
(3) Mass spectrum (FABMS): m/z 393 (M+H)$^+$
(4) Specific rotation: $[\alpha]_D^{25}$ +3.6° (c 0.59, MeOH) (as trihydrochloride)
(5) $^1$H NMR spectrum (400 MHz, $CD_3OD$)(as trihydrochloride) δ (ppm): 1.98 (2H, quintet, tetrahydropyrimidine), 3.13 (4H, br s, piperazine), 3.42 (4H, m, tetrahydropyrimidine), 3.59 (4H, br s, piperazine), 3.81 (1H, dd, CONHC$\underline{H}_2$CH), 3.96 (1H, dd, CONHC$\underline{H}_2$CH), 4.23 (1H, dd, CONHC$\underline{H}_2$CH), 7.11 (1H, t, C$_6$H$_3$), 7.62 (1H, dd, C$_6$H$_3$), 7.67 (1H, dd, C$_6$H$_3$)

Example 76

(2S)-Benzyloxycarbonylamino-3-[3-fluoro-4-{4-(1,4,5,6-tetrahydropyrimidin-2-yl)-piperazin-1-yl}-benzoylamino]-propionic Acid Acetone (4.0 ml) and 4.0 ml of water were added to 43 mg of the compound prepared in Example 75 to prepare a solution, and 59 mg of potassium carbonate was added to the solution. Benzyloxycarbonyl chloride (0.12 ml) was added thereto. The mixture was stirred for 30 min, and then concentrated under the reduced pressure. The residue was purified by preparative thin-layer chromatography on silica gel (development system: methylene chloride-ethanol-water-concentrated aqueous ammonia=8:8:1:1), and then purified by Sephadex LH-20(development system: methanol) to prepare 13 mg of the title compound.

Physicochemical Properties of Compound Prepared in Example 76

(1) Color and form: Colorless solid
(2) Molecular formula: $C_{26}H_{31}N_6O_5F$
(3) Mass spectrum (FABMS): m/z 527 (M+H)$^+$
(4) Specific rotation: $[\alpha]_D^{25}$ –2.1° (c 0.45, MeOH)
(5) $^1$H NMR spectrum (400 MHz, $CD_3OD$) δ (ppm): 1.96 (2H, quintet, tetrahydropyrimidine), 3.21 (4H, br t, piperazine), 3.41 (4H, br t, tetrahydropyrimidine), 3.53 (4H, br t, piperazine), 3.67 (1H, dd, CONHC$\underline{H}_{12}$CH), 3.75 (1H, dd, CONHC$\underline{H}_{12}$CH), 4.26 (1H, dd, CONHCH$_2$C$\underline{H}$), 5.05 (2H, d, C$\underline{H}_2$C$_6$H$_5$), 7.01 (1H, t, C$_6$H$_3$), 7.28 (5H, m, CH$_2$C$_6$$\underline{H}_5$), 7.53 (1H, dd, C$_6$H$_3$), 7.56 (1H, dd, C$_6$H$_3$)

Example 77 t-Butyl (2S)-ethylamino-3-[3-fluoro-4-{4-(pyrimidin-2-yl)-piperazin-1-yl}-benzoylamino]-propionate Tetrahydrofuran (60 ml) and 30 ml of ethanol were added to 206 mg of the compound prepared in Example 73 to prepare a solution, and 207 mg of 10% palladium-carbon was added to the solution. The mixture was vigorously stirred in a hydrogen atmosphere at room temperature for 24 hr. The insolubles were collected by filtration, and then washed twice with tetrahydrofuran. The filtrate was combined with the washings, followed by concentration under the reduced pressure. The residue was purified by preparative thin-layer chromatography on silica gel (development system: methylene chloride-methanol=9:1) to prepare 56 mg of the title compound.

Physicochemical Properties of Compound Prepared in Example 77
(1) Color and form: Colorless solid
(2) Molecular formula: $C_{24}H_{33}N_6O_3F$
(3) Mass spectrum (FABMS): m/z 473 (M+H)$^+$
(4) Specific rotation: $[\alpha]_D^{25}$ +7.3° (c 1.0, $CH_2Cl_2$)
(5) $^1$H NMR spectrum (400 MHz, $CDCl_3$) δ (ppm): 1.12 (3H, t, $CH_2C\underline{H}_3$), 1.47 (9H, s, t-Bu), 2.59 (1H, dq, $C\underline{H}_2CH_3$), 2.71 (1H, dq, $C\underline{H}_2CH_3$), 3.22 (4H, br t, piperazine), 3.34 (1H, dd, $CONHCH_2C\underline{H}$), 3.44 (1H, ddd, $CONHC\underline{H}_2CH$), 3.77 (1H, ddd, $CONHC\underline{H}_2CH$), 4.00 (4H, br t, piperazine), 6.53 (1H, t, pyrimidine), 6.95 (1H, t, $C_6H_3$), 7.50 (2H, m, $C_6H_3$), 8.34 (2H, d, pyrimidine)

Example 78

(2S)-Ethylamino-3-[3-fluoro-4-{4-(pyrimidin-2-yl)-piperazin-1-yl}-benzoylamino]-propionic Acid Methylene chloride (5.0 ml) was added to 55 mg of the compound prepared in Example 77 to prepare a solution, and 5.0 ml of trifluoroacetic acid was added to the solution at room temperature. The mixture was stirred at that temperature for 5 hr before the reaction solution was concentrated under the reduced pressure to prepare 64 mg of tritrifluoroacetate of the title compound.
Physicochemical Properties of Compound Prepared in Example 78
(1) Color and form: pale yellow solid
(2) Molecular formula: $C_{20}H_{25}N_6O_3F$
(3) Mass spectrum (TSPMS): m/z 417 (M+H)$^+$
(4) Specific rotation: $[\alpha]_D^{25}$ +1.9° (c 0.84, MeOH)(as tritrifluoroacetate)
(5) $^1$H NMR spectrum (400 MHz, $CD_3OD$)(as tritrifluoroacetate) δ (ppm): 1.36 (3H, t, $CH_2C\underline{H}_3$), 3.25 (6H, m, piperazine and $C\underline{H}_2CH_3$), 3.83 (1H, dd, $CONHC\underline{H}_2CH$), 3.98 (4H, br t, piperazine), 4.07 (1H, dd, $CONHC\underline{H}_2CH$), 4.20 (1H, dd, $CONHCH_2C\underline{H}$), 6.66 (1H, t, pyrimidine), 7.11 (1H, t, $C_6H_3$), 7.61 (1H, dd, $C_6H_3$), 7.65 (1H, dd, $C_6H_3$), 8.37 (2H, d, pyrimidine)

Example 79

(2S)-Ethylamino-3-[3-fluoro-4-{4-(1,4,5,6-tetrahydropyrimidin-2-yl)-piperazin-1-yl}-benzoylamino]-propionic Acid 1,4-Dioxane (10 ml) and 5.0 ml of water were added to 64 mg of the compound prepared in Example 78 to prepare a solution, and 52 mg of 10% palladium-carbon was added to the solution. The mixture was vigorously stirred in a hydrogen atmosphere at room temperature for 8.0 hr. The insolubles were collected by filtration, and then washed twice with 1,4-dioxane. The filtrate was combined with the washings, followed by concentration under the reduced pressure to prepare 50 mg of the title compound.
Physicochemical Properties of Compound Prepared in Example 79
(1) Color and form: Colorless solid
(2) Molecular formula: $C_{20}H_{29}N_6O_3F$
(3) Mass spectrum (TSPMS): m/z 421 (M+H)$^+$
(4) Specific rotation: $[\alpha]_D^{25}$ −23° (c 1.0, MeOH)
(5) $^1$H NMR spectrum (400 MHz, $CD_3OD$) δ (ppm): 1.29 (3H, t, $CH_2C\underline{H}_3$), 1.97 (2H, quintet, tetrahydropyrimidine), 3.06 (2H, q, $C\underline{H}_2CH_3$), 3.25 (4H, m, piperazine), 3.42 (4H, br t, tetrahydropyrimidine), 3.55 (4H, br t, piperazine), 3.60 (1H, dd, $CONHCH_2C\underline{H}$), 3.74 (1H, dd, $CONHC\underline{H}_2CH$), 3.84 (1H, dd, $CONHC\underline{H}_2CH$), 7.08 (1H, t, $C_6H_3$), 7.60 (1H, d, $C_6H_3$), 7.64 (1H, d, $C_6H_3$)

Example 80 t-Butyl (2S)-amino-3-[3-fluoro-4-{4-(pyrimidin-2-yl)-piperazin-1-yl}-benzoylamino]-propionate Tetrahydrofuran (120 ml) was added to 288 mg of the compound prepared in Example 73 to prepare a solution, and 293 mg of 10% palladium-carbon was added to the solution. The mixture was vigorously stirred in a hydrogen atmosphere at room temperature for 1.5 hr. The insolubles were collected by filtration, and then washed twice with tetrahydrofuran. The filtrate was combined with the washings, followed by concentration under the reduced pressure to prepare 56 mg of the title compound.
Physicochemical Properties of Compound Prepared in Example 80
(1) Color and form: Colorless solid
(2) Molecular formula: $C_{22}H_{29}N_6O_3F$
(3) Mass spectrum (FABMS): m/z 445 (M+H)$^+$
(4) Specific rotation: $[\alpha]_D^{25}$ +4.2° (c 1.5, $CH_2Cl_2$)
(5) $^1$H NMR spectrum (400 MHz, $CDCl_3$) δ (ppm): 1.48 (9H, s, t-Bu), 3.23 (4H, br t, piperazine), 3.46 (1H, ddd, $CONHC\underline{H}_2CH$), 3.58 (1H, dd, $CONHCH_2C\underline{H}$), 3.80 (1H, ddd, $CONHC\underline{H}_2CH$), 4.00 (4H, br t, piperazine), 6.53 (1H, t, pyrimidine), 6.95 (1H, t, $C_6H_3$), 7.49 (1H, dd, $C_6H_3$), 7.52 (1H, dd, $C_6H_3$), 8.34 (2H, d, pyrimidine)

Example 81 t-Butyl 3-[3-fluoro-4-{4-(pyrimidin-2-yl)-piperazin-1-yl}-benzoylamino]-(2S)-(2,4,6-trimethyl-benzenesulfonylamino)-propionate Dimethylformamide (10 ml) was added to 243 mg of the compound prepared in Example 80 to prepare a solution. 2,4,6-Trimethylbenzenesulfonyl chloride (111 mg) and 0.18 ml of diisopropylethylamine were added to the solution, and the mixture was stirred for 2 hr. Sodium hydrogencarbonate (10 mg) was added to stop the reaction. Ethyl acetate (500 ml) and 500 ml of water were added thereto. The organic layer was then separated, dried over anhydrous magnesium sulfate, and concentrated under the reduced pressure. The residue was purified by column chromatography on silica gel (development system: hexane-ethyl acetate=1:2) to prepare 140 mg of the title compound.
Physicochemical Properties of Compound Prepared in Example 81
(1) Color and form: Colorless solid
(2) Molecular formula: $C_{31}H_{39}N_6O_5SF$
(3) Mass spectrum (TSPMS): m/z 627 (M+H)$^+$
(4) Specific rotation: $[\alpha]_D^{25}$ +56° (c 0.95, $CH_2Cl_2$)
(5) $^1$H NMR spectrum (400 MHz, $CDCl_3$) δ (ppm): 1.31 (9H, s, t-Bu), 2.28 (3H, s, $CH_3$), 2.64 (6H, S, $CH_3$), 3.28 (4H, br t, piperazine), 3.58 (1H, ddd, $CONHC\underline{H}_2CH$), 3.83 (2H, m, $CONHC\underline{H}_2CH$), 4.11 (4H, m, piperazine), 6.65 (1H, br t, pyrimidine), 6.94 (2H, s, $C_6H_2$), 6.96 (1H, t, $C_6H_3$), 7.55 (2H, m, $C_6H_3$), 8.44 (2H, d, pyrimidine)

Example 82

3-[3-Fluoro-4-{4-(pyrimidin-2-yl)-piperazin-1-yl}-benzoylamino]-(2S)-(2,4,6-trimethyl-benzenesulfonylamino)-propionic Acid Methylene chloride (6.0 ml) was added to 107 mg of the compound prepared in Example 81 to prepare a solution, and 6.0 ml of trifluoroacetic acid was added at room temperature to the solution. The mixture was stirred at that temperature for 6 hr before the reaction solution was concentrated under the reduced pressure to prepare 118 mg of tritrifluoroacetate of the title compound.

Physicochemical Properties of Compound Prepared in Example 82

(1) Color and form: pale yellow solid
(2) Molecular formula: $C_{27}H_{31}N_6O_5SF$
(3) Mass spectrum (TSPMS): m/z 571 (M+H)$^+$
(4) Specific rotation: $[\alpha]_D^{25}$ +80° (c 0.56, MeOH)(as tritrifluoroacetate)
(5) $^1$H NMR spectrum (400 MHz, CD$_3$OD) (as tritrifluoroacetate) δ (ppm): 2.17 (3H, s, CH$_3$), 2.58 (6H, s, CH$_3$), 3.28 (4H, br t, piperazine), 3.44 (1H, dd, CONHC$\underline{H}_2$CH), 3.70 (1H, dd, CONHC$\underline{H}_2$CH), 4.00 (4H, br t, piperazine), 4.11 (1H, dd, CONHCH$_2$C$\underline{H}$), 6.73 (1H, t, pyrimidine), 6.83 (2H, S, C$_6$H$_2$), 7.07 (1H, t, C$_6$H$_3$), 7.40 (1H, dd, C$_6$H$_3$), 7.49 (1H, dd, C$_6$H$_3$), 8.43 (2H, d, pyrimidine)

Example 83

3-[3-Fluoro-4-{4-(1,4,5,6-tetrahydropyrimidin-2-yl)-piperazin-1-yl}-benzoylamino]-(2S)-(2,4,6-trimethyl-benzenesulfonylamino)-propionic Acid Acetic acid (25 ml) and 2.5 ml of concentrated hydrochloric acid were added to 53 mg of the compound prepared in Example 82 to prepare a solution, and 28 mg of 10% palladium-carbon was added to the solution. The mixture was vigorously shaken at room temperature for 3.5 hr under a hydrogen pressure of 3 atm. The insolubles were collected by filtration, and then washed twice with water. The filtrate was combined with the washings, followed by concentration under the reduced pressure. The reside was purified by preparative thin-layer chromatography on silica gel (development system: methylene chloride-ethanol-water-concentrated aqueous ammonia=8:8:1:1), and then purified by Sephadex LH-20 (development system: methanol) to prepare 9.2 mg of the title compound.

Physicochemical Properties of Compound Prepared in Example 83

(1) Color and form: Colorless solid
(2) Molecular formula: $C_{27}H_{31}N_6O_5SF$
(3) Mass spectrum (FABMS): m/z 575 (M+H)$^+$
(4) Specific rotation: $[\alpha]_D^{25}$ +165° (c 0.32, MeOH)
(5) $^1$H NMR spectrum (400 MHz, CD$_3$OD) δ (ppm): 1.97 (2H, quintet, tetrahydropyrimidine), 2.22 (3H, s, CH$_3$), 2.62 (6H, s, CH$_3$), 3.24 (4H, br t, piperazine), 3.41 (4H, br t, tetrahydropyrimidine), 3.54 (5H, m, piperazine and CONHC$\underline{H}_2$CH), 3.64 (2H, m, CONHC$\underline{H}_2$C$\underline{H}$), 6.91 (2H, S, C$_6$H$_2$), 7.05 (1H, t, C$_6$H$_3$), 7.50 (1H, dd, C$_6$H$_3$), 7.57 (1H, dd, C$_6$H$_3$ )

Example 84 t-Butyl (2S)-amino-3-[4-{4-(pyrimidin-2-yl)-piperazin-1-yl}-benzoylamino]-propionate Tetrahydrofuran (20 ml) was added to 51 mg of the compound prepared in Example 27 to prepare a solution, and 54 mg of 10% palladium-carbon was added to the solution. The mixture was vigorously stirred in a hydrogen atmosphere at room temperature for 2.0 hr. The insolubles were collected by filtration, and then washed twice with tetrahydrofuran. The filtrate was combined with the washings, followed by concentration under the reduced pressure. The residue was purified by column chromatography on silica gel (development system: methylene chloride-methanol=10:1) to prepare 31 mg of the title compound.

Physicochemical Properties of Compound Prepared in Example 84

(1) Color and form: Colorless solid
(2) Molecular formula: $C_{22}H_{30}N_6O_3$
(3) Mass spectrum (TSPMS): m/z 427 (M+H)$^+$
(4) Specific rotation: $[\alpha]_D^{25}$ +5.0° (c 1.3, CH$_2$Cl$_2$)
(5) $^1$H NMR spectrum (400 MHz, CDCl$_3$) δ (ppm): 1.47 (9H, s, t-Bu), 3.38 (4H, br t, piperazine), 3.47 (1H, ddd, CONHC$\underline{H}_2$CH), 3.61 (1H, dd, CONHCH$_2$C$\underline{H}$), 3.82 (1H, ddd, CONHC$\underline{H}_2$CH), 3.99 (4H, br t, piperazine), 6.54 (1H, t, pyrimidine), 6.93 (2H, d, C$_6$H$_4$), 7.72 (2H, d, C$_6$H$_4$), 8.34 (2H, d, pyrimidine)

Example 85

(2S)-Amino-3-[4-{4-(pyrimidin-2-yl)-piperazin-1-yl}-benzoylamino]-propionic Acid Methylene chloride (2.0 ml) was added to 29 mg of the compound prepared in Example 84 to prepare a solution, and 2.0 ml of trifluoroacetic acid was added at room temperature to the solution. The mixture was stirred at that temperature for 4 hr before the reaction solution was concentrated under the reduced pressure to prepare 33 mg of tritrifluoroacetate of the title compound.

Physicochemical Properties of Compound Prepared in Example 85

(1) Color and form: Pale yellow solid
(2) Molecular formula: $C_{18}H_{22}N_6O_3$
(3) Mass spectrum (TSPMS): m/z 371 (M+H)$^+$
(4) Specific rotation: $[\alpha]_D^{25}$ +7.5° (c 0.69, DMSO)(as tritrifluoroacetate)
(5) $^1$H NMR spectrum (400 MHz, CD$_3$OD)(as tritrifluoroacetate) δ (ppm): 3.48 (4H, br t, piperazine), 3.82 (1H, dd, CONHC$\underline{H}_2$CH), 3.94 (1H, dd, CONHC$\underline{H}_2$CH), 3.96 (4H, br t, piperazine), 4.18 (1H, dd, CONHCH$_2$C$\underline{H}$), 6.63 (1H, t, pyrimidine), 7.02 (2H, d, C$_6$H$_4$), 7.78 (2H, d, C$_6$H$_4$), 8.35 (2H, d, pyrimidine)

Example 86

Ethyl 3-[4-{4-(pyrimidin-2-yl)-piperazin-1-yl}-benzoylamino]-propionate

Dimethylformamide (10 ml) was added to 97 mg of intermediate 3 to prepare a solution, and 176 mg of—alanine ethyl ester hydrochloride was added to the solution. Further, 72 mg of 1-hydroxybenzotriazole, 0.18 ml of N-methylmorpholine, and 148 mg of 1-ethyl-3-(3-dimethylaminopropyl)carbodiimide hydrochloride were added thereto, and the mixture was stirred at room temperature for 24 hr. A saturated aqueous sodium hydrogencarbonate solution (30 ml) was added to stop the reaction. Ethyl acetate (300 ml) and 100 ml of water were added thereto. The organic layer was then separated, dried over anhydrous magnesium sulfate, and concentrated under the reduced pressure. The residue was purified by column chromatography on silica gel (development system: methylene chloride-methanol=15:1) to prepare 110 mg of the title compound.

Physicochemical Properties of Compound Prepared in Example 86

(1) Color and form: Colorless solid (2) Molecular formula: $C_{20}H_{25}N_5O_3$
(3) Mass spectrum (TSPMS): m/z 384 (M+H)$^+$
(4) $^1$H NMR spectrum (400 MHz, CDCl$_3$) δ (ppm): 1.27 (3H, t, CH$_2$CH$\underline{H}_3$), 2.64 (2H, t, CONHCH$_2$C$\underline{H}_2$), 3.38 (4H, br t, piperazine), 3.71 (2H, q, CONHC$\underline{H}_2$CH$_2$), 3.99 (4H, m, piperazine), 4.17 (2H, q, C$\underline{H}_2$CH$_3$), 6.54 (1H, t, pyrimidine), 6.93 (2H, d, C$_6$H$_4$), 7.70 (2H, d, C$_6$H$_4$), 8.34 (2H, d, pyrimidine)

Example 87

3-[4-{4-(Pyrimidin-2-yl)-piperazin-1-yl}-benzoylamino]-propionic Acid

Methanol (0.20 ml) and 0.60 ml of tetrahydrofuran were added to 40 mg of the compound prepared in Example 86 to prepare a solution, and 0.20 ml of a 1 N aqueous sodium hydroxide solution was added to the solution. The mixture was stirred at 60° C. for 5.0 hr and was then cooled to room temperature, and the system was adjusted to pH 7 by the addition of 1 N hydrochloric acid. The resultant precipitate was collected by filtration on a glass filter, and then dried to prepare 21 mg of the title compound.

Physicochemical Properties of Compound Prepared in Example 87
(1) Color and form: Colorless solid
(2) Molecular formula: $C_{18}H_{21}N_5O_3$
(3) Mass spectrum (TSPMS): m/z 356 (M+H)$^+$
(4) $^1$H NMR spectrum (400 MHz, CD$_3$OD) δ (ppm): 2.60 (2H, t, CONHCH$_2$C$\underline{H}_2$), 3.38 (4H, br t, piperazine), 3.60 (2H, t, CONHC$\underline{H}_2$CH$_2$), 3.95 (4H, m, piperazine), 6.62 (1H, t, pyrimidine), 7.02 (2H, d, C$_6$H$_4$), 7.73 (2H, d, C$_6$H$_4$), 8.34 (2H, d, pyrimidine)

Pharmacological Test Example 1

α$_v$β$_3$ Binding Assay

Integrin α$_v$β$_3$ antagonistic activity was measured for the compounds according to the present invention in a vitronectin-vitronectin receptor binding assay system in accordance with the method of Kouns et al. (W. C. Kouns, D. Kirchhofer, P. Hadvary, A. Edenhofer, T. Weller, G. Pfenninger, H. R. Baumgartner, L. K. Jennings and B. Steiner, Blood, 8, 2539–2547 (1992)).

Specifically, a vitronectin receptor (protein content: 118 μg/ml) purified from the human placenta in accordance with the method of Pytela et al. (R. Pytela, M. D. Pierschbacher, S. Argraves, S. Suzuki, and E. Ruoslahti, Method in Enzymology, 144, 475–489 (1987)) was diluted 50 times with TBS (20 mM Tris-HCl, 150 mM NaCl, 1 mM CaCl$_2$, 1 mM MgCl$_2$, pH 7.4), and distributed and coated on wells (50 μl/well) of a plate (Maxisorp, Nunc, 96 well Immuno Plate). The plate was then allowed to stand at 4° C. for 1 day, washed twice with TBS (200 μl/well), and then subjected to blocking with TBS (150 μl/well) containing 1% bovine serum albumin (SIGMA) at 4° C. overnight. After washing twice with TBS (200 μl/well), 50 μl of vitronectin (CALBIOCHEM) adjusted to 0.2 μg/ml by the addition of TBS (TBS-Tween) containing 0.01% Tween-20 was mixed with 50 μl of each test compound adjusted to each concentration in wells, and a reaction was allowed to proceed at room temperature for 4 hr. After the completion of the reaction, the wells were washed five times with TBS-Tween. A solution prepared by diluting anti-vitronectin rabbit antiserum (CHEMICON) 500 times with TBS-Tween was added as a primary antibody in an amount of 50 μl per well, and a reaction was allowed to proceed at room temperature for 1.5 hr. After washing five times with 200 μl/well of TBS-Tween, a peroxidase (POD)-labeled anti-rabbit IgG antibody solution (CAPPEL) diluted 500 times with TBS-Tween was added as a secondary antibody in an amount of 50 μl/well, and a reaction was allowed to proceed at room temperature for 1.5 hr. After washing five times with TBS-Tween (200 μl /well), ABTS (2,2'-azino-bis(3-ethylbenzthiazoline-6-sulfonic acid), SIGMA) was adjusted to 1 mg/ml by the addition of a ten-fold diluted POD-buffer (ZYMED), and added in an amount of 50 μl/well, and a reaction was allowed to proceed for 5 to 10 min. A 0.1 M citric acid buffer (pH 4.3) containing 0.05% NaN$_3$ was added in an amount of 50 μl/well to stop the reaction, followed by the measurement of the absorbance at 415 nm with a microplate reader (MTP 32, Corona Electric) (reference: 675 nm). The total binding was defined as the absorbance after a reaction using 50 μl of TBS-Tween instead of the test compound, and the non-specific binding (100% inhibition) was defined as the absorbance after a reaction using 50 μl of TBS-Tween containing 2×10$^{-3}$ M RGDS. The inhibition was calculated by the following equation:

$$\text{Inhibition}(\%) = 100 - \frac{(\text{absorbance in the presence of test compound} - \text{non-specific binding})}{(\text{total binding} - \text{non-specific binding})} \times 100$$

IC$_{50}$ was determined from a primary regression line of the logarithm of each concentration of the test compound and the logarithm of (100−inhibition)/inhibition.

As a result, all the compounds of Examples 56, 59, 62, 65, 72, and 83 among the phenylpiperazine compounds represented by formula (I) had high integrin α$_v$β$_3$ antagonistic activity. In particular, the compounds of Examples 59, 65, and 83 strongly inhibited binding between vitronectin and vitronectin receptor, and respectively had IC$_{50}$ values of 3.5 nM, 6.3 nM, and 5.8 nM.

Pharmacological Test Example 2

GP IIb/IIIa Antagonistic Activity and Human Platelet Aggregation Inhibitory Activity GP IIb/IIIa antagonistic activity was measured for the compounds according to the present invention. The measurement of the GP IIb/IIIa antagonistic activity was carried out according to the method described in Pharmacological Test 2 in WO 94/21599. As a result, the compounds of Examples 3, 56, 59, 62, 65, 72, 82, and 83 had extremely high GP IIb/IIIa antagonistic activity. In particular, all the compounds of Examples 56, 59, 62, and 72 had an IC$_{50}$ value of not more than 0.2 nM.

Human platelet aggregation inhibitory activity was measured for the compounds according to the present invention. The measurement of the human platelet aggregation activity was carried out according to the method described in Pharmacological Test 1 in WO 94/21599. As a result, the compounds of Examples 3, 6, 9, 12, 34, and 83 very strongly inhibited human platelet aggregation. In particular, the compounds of Examples 3, 6, 9, and 34 strongly inhibited human platelet aggregation, and respectively had IC$_{50}$ values of 34 nM, 50 nM, 50 nM, and 38 nM.

Pharmacological Test Example 3
Inhibitory Activity Against Adhesion of Human Vascular Smooth Muscle Cells to Vitronectin The adhesion of human vascular smooth muscle cells to immobilized human vitronectin was measured in accordance with the method of Liaw et al. (Liaw L, Almeida M, Hart C E, Schwartz S M, and Giachelli C M, Circulation Research, 74 (2), 214–224 (1994)).

A Dulbecco's phosphate buffer (Dulbecco's PBS(−), Nissui Pharmaceutical Co., Ltd.) solution of human plasma-derived vitronectin (CALBIOCHEM) adjusted to a concentration of 4 μg/ml was first added to wells (50 μl/well) of a microplate (Maxisorp, Nunc), and a reaction for immobilization was allowed to proceed at 4° C. overnight. After washing twice with 150 μl of Dulbecco's phosphate buffer, a Dulbecco's phosphate buffer containing 10 mg/ml of bovine serum albumin (SIGMA) was added, followed by blocking at 37° C. for one hr. The assay plate was washed twice with 150 μl of Dulbecco's phosphate buffer.

Separately, human vascular smooth muscle cells cultivated at 37° C. under 5% carbon dioxide in a medium for vascular smooth muscle cells (Clonetics) were separated using a Dulbecco's phosphate buffer containing trypsin-EDTA (GIBCO BRL), washed with Dulbecco's phosphate buffer, and then suspended in a Dulbeccols modified Eagle's basal medium (Nissui Pharmaceutical Co., Ltd.) containing 0.1% bovine serum albumin to a concentration of $5 \times 10^5$/ml.

Next, 50 μl of a Dulbecco's modified Eagle's basal medium containing 10 mg/ml of bovine serum albumin with a medicament added thereto was added to the wells of the human vitronectin-coated assay microplate, followed by pre-cultivation under 5% carbon dioxide at 37° C. for 10 min. Thereafter, 50 μl of the medium with human vascular smooth muscle cells suspended therein was added thereto, and the plate was thoroughly stirred. A reaction was allowed to proceed under 5% carbon dioxide at 37° C. for 90 min. The reaction solution containing non-adherent cells were removed, followed by washing three times with Dulbecco's phosphate buffer. For the adhered cells, 100 ml of a Dulbecco's phosphate buffer containing 4% paraformaldehyde (Wako Pure Chemical Industries, Ltd.) was added, and immobilization was allowed to proceed at room temperature for 10 min. Next, 100 ml of a Dulbecco's phosphate buffer containing 0.5% Toluidine Blue (Croma) and 4% paraformaldehyde was added, and staining was allowed to proceed at room temperature for 5 min, followed by thorough washing with distilled water. The inside of the wells was then air-dried, and 1% aqueous sodium dodecylsulfate solution was added to perfom cytolysis. The absorbance of the microplate thus obtained was measured at 595 nm. The total binding was defined as the absorbance of the well not containing the test compound, and the non-specific binding (100% inhibition) was defined as the absorbance of the well which does not contain vitronectin and has been subjected to blocking with bovine serum albumin. The inhibition was calculated by the following equation. $IC_{50}$ was determined from a primary regression line of the logarithm of each concentration of the test compound and the logarithm of (100−inhibition)/inhibition.

As a result, for the compound of Example 30, the $IC_{50}$ value on the $\alpha_v\beta_3$ binding inhibitory activity (Pharmacological Test Example 1) was 31 nM, while for this compound, the $IC_{50}$ value on the inhibitory activity against the adhesion of human vascular smooth muscle cells to vitronectin was 750 nM. This demonstrates that the compound according to the present invention has potent cell adhesion inhibitory activity in human blood vessels.

Pharmacological Test Example 4
$\alpha_5\beta_1$ Binding Assay

Integrin $\alpha_5\beta_1$ antagonistic activity (lethality) was measured for the compounds according to the present invention in a fibronectin-fibronectin receptor binding assay system in accordance with the method of Kouns et al. (W. C. Kouns, D. Kirchhofer, P. Hadvary, A. Edenhofer, T. Weller, G. Pfenninger, H. R. Baumgartner, L. K. Jennings and B. Steiner, Blood, 80, 2539–2547 (1992)).

Specifically, a fibronectin receptor (protein content: 52.1 μg/ml) purified from the human placenta by the method of Pytela et al. (R. Pytela, M. D. Pierschbacher, S. Argraves, S. Suzuki, and E. Ruoslahti, Method in Enzymology, 144, 475–489 (1987)) was diluted 25 times with TBS (20 mM Tris-HCl, 150 mM NaCl, 1 mM $CaCl_2$, 1 mM $MgCl_2$, pH 7.4), and distributed and coated on wells (50 μl/well) of a plate (Maxisorp, Nunc, 96 well Immuno Plate). The plate was then allowed to stand at 4° C. for one day, washed twice with TBS (200 μl/well), and then subjected to blocking with TBS (150 μl/well) containing 3% skim milk (DIFCO) at 4° C. overnight. After washing twice with TBS (200 μl/well) containing 0.05% Tween-20 and then washing twice with TBS (200 μl/well), purification was carried out according to the method of E. Engvall et al. (E. Engvall, E. Ruoslahti and E. J. Miller, J. Exp. Med., 147, 1584–1595 (1978)), and 50 μl of fibronectin adjusted to 0.2 μg/ml by the addition of TBS (TBS-Tween) containing 0.01% Tween-20 was mixed with 50 μl of each test compound adjusted to each concentration in the wells, and a reaction was allowed to proceed at room temperature for 3 hr. After the completion of the reaction, the wells were washed five times with TBS-Tween. A solution prepared by diluting a peroxidase-labeled fibronectin antibody (CAPPEL) 500 times with TBS-Tween was added in an amount of 50 μl per well, and a reaction was allowed to proceed at room temperature for 1.5 hr. After washing five times with TBS-Tween (200 μl/well), ABTS (SIGMA) adjusted to 1 mg/ml by the addition of a ten-fold diluted POD-buffer (ZYMED) was added in an amount of 50 μl/well, and a reaction was allowed to proceed for 5 to 10 min. A 0.1 M citric acid buffer (pH 4.3) containing 0.05% $NaN_3$ was added in an amount of 50 μl/well to stop the reaction, followed by the measurement of the absorbance at 415 nm with a microplate reader (MTP 32, Corona Electric) (reference: 675 nm). The total binding was defined as the absorbance after a reaction using 50 μl of TBS-Tween instead of the test compound, and the non-specific binding (100% inhibition) was defined as the absorbance after a reaction using 50 μl of TBS-Tween containing $2 \times 10^{-3}$ M RGDS. The inhibition was calculated by the following equation:

$$\text{Inhibitation}(\%) = 100 - \frac{(\text{absorbance in the presence of test compound} - \text{non-specific binding})}{(\text{total binding} - \text{non-specific binding})} \times 100$$

$$\text{Inhibition}(\%) = 100 - \frac{(\text{absorbance in the presence of test compound} - \text{non-specific binding})}{(\text{total binding} - \text{non-specific binding})} \times 100$$

IC$_{50}$ was determined from a primary regression line of the logarithm of each concentration of the test compound and the logarithm of (100−inhibition)/inhibition.

As a result, the compound (L-748, 415) described in WO 95/32710 had an IC$_{50}$ value of 120 nM, whereas the compounds of Examples 59 and 83 respectively had IC$_{50}$ values of 63,000 nM and 13,000 nM. This demonstrates that the compounds according to the present invention can function as medicaments having very low side effect.

Acute Toxicity Test

The compound of Example 3 was intravenously administered to mice. As a result, no special symptom was developed at a dose of 12.5 mg/kg, indicating that the compound has low toxicity.

The compounds of Examples 1 to 87 have the following structures.

| # | A | X | Z | p | R⁴ | R⁵ | Q | R⁶ | R⁷ | q | R⁸ | R⁹ |
|---|---|---|---|---|---|---|---|---|---|---|---|---|
| 1 | pyrimidinyl | N | N | 2 | m = 0 | n = 0 | >C=O | H | H | 1 | —NHSO₂Ph* | t-Bu |
| 2 | pyrimidinyl | N | N | 2 | m = 0 | n = 0 | >C=O | H | H | 1 | —NHSO₂Ph | H |
| 3 | tetrahydropyrimidinyl | N | N | 2 | m = 0 | n = 0 | >C=O | H | H | 1 | —NHSO₂Ph | H |
| 4 | pyrimidinyl | N | N | 3 | m = 0 | n = 0 | >C=O | H | H | 1 | —NHSO₂Ph | t-Bu |
| 5 | pyrimidinyl | N | N | 3 | m = 0 | n = 0 | >C=O | H | H | 1 | —NHSO₂Ph | H |
| 6 | tetrahydropyrimidinyl | N | N | 3 | m = 0 | n = 0 | >C=O | H | H | 1 | —NHSO₂Ph | H |
| 7 | pyrimidinyl | N | N | 2 | m = 1; 3-Me | n = 0 | >C=O | H | H | 1 | —NHSO₂Ph | t-Bu |
| 8 | pyrimidinyl | N | N | 2 | m = 1; 3-Me | n = 0 | >C=O | H | H | 1 | —NHSO₂Ph | H |
| 9 | tetrahydropyrimidinyl | N | N | 2 | m = 1; 3-Me | n = 0 | >C=O | H | H | 1 | —NHSO₂Ph | H |
| 10 | pyrimidinyl | N | N | 2 | m = 1; 3R-Me | n = 0 | >C=O | H | H | 1 | —NHSO₂Ph | t-Bu |

-continued
| | A | X | Z | p | R⁴ | R⁵ | Q | R⁶ | R⁷ | q | R⁸ | R⁹ |
|---|---|---|---|---|---|---|---|---|---|---|---|---|
| 11 | 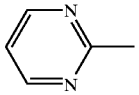 | N | N | 2 | m = 1; 3R-Me | n = 0 | >C=O | H | H | 1 | —NHSO₂Ph | H |
| 12 |  | N | N | 2 | m = 1; 3R-Me | n = 0 | >C=O | H | H | 1 | —NHSO₂Ph | H |
| 13 | 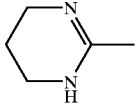 | N | N | 2 | m = 1; 3S-Me | n = 0 | >C=O | H | H | 1 | —NHSO₂Ph | t-Bu |
| 14 |  | N | N | 2 | m = 1; 3S-Me | n = 0 | >C=O | H | H | 1 | —NHSO₂Ph | H |
| 15 | 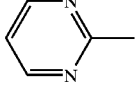 | N | N | 2 | m = 1; 3S-Me | n = 0 | >C=O | H | H | 1 | —NHSO₂Ph | H |
| 16 |  | N | N | 2 | m = 0 | n = 0 | >C=O | H | H | 1 | —NHSO₂Ph | t-Bu |
| 17 | 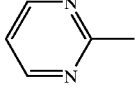 | N | N | 2 | m = 0 | n = 0 | >C=O | H | H | 1 | —NHSO₂Ph | H |
| 18 |  | N | N | 2 | m = 0 | n = 0 | >C=O | H | —C≡CH | 1 | H | Et |
| 19 | 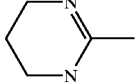 | N | N | 2 | m = 0 | n = 0 | >C=O | H | —C≡CH | 1 | H | H |
| 20 |  | N | N | 2 | m = 0 | n = 0 | >CH₂ | H | H | 1 | —NHSO₂Ph | t-Bu |
| 21 | 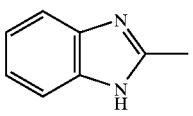 | N | N | 2 | m = 0 | n = 0 | >CH₂ | H | H | 1 | —NHSO₂Ph | H |
| 22 |  | N | N | 2 | m = 0 | n = 0 | >CH₂ | H | H | 1 | —NHSO₂Ph | H |
| 23 | 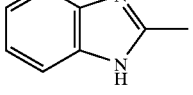 | N | N | 2 | m = 0 | n = 0 | >CH₂ | Me | H | 1 | —NHSO₂Ph | H |

-continued

| | A | X | Z | p | R⁴ | R⁵ | Q | R⁶ | R⁷ | q | R⁸ | R⁹ |
|---|---|---|---|---|---|---|---|---|---|---|---|---|
| 24 | 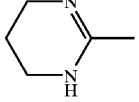 | N | N | 2 | m = 0 | n = 0 | CH₂ | Me | H | 1 | —NHSO₂Ph | H |
| 25 | 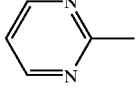 | N | N | 2 | m = 0 | n = 0 | CH₂ | Bn | H | 1 | —NHSO₂Ph | H |
| 26 | 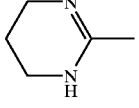 | N | N | 2 | m = 0 | n = 0 | CH₂ | Bn | H | 1 | —NHSO₂Ph | H |
| 27 | 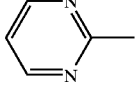 | N | N | 2 | m = 0 | n = 0 | C=O | H | H | 1 | —NHCO₂CH₂Ph | t-Bu |
| 28 | 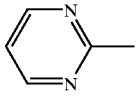 | N | N | 2 | m = 0 | n = 0 | C=O | H | H | 1 | —NHCO₂CH₂Ph | H |
| 29 | 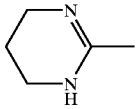 | N | N | 2 | m = 0 | n = 0 | C=O | H | H | 1 | —NH₂ | H |
| 30 | 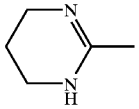 | N | N | 2 | m = 0 | n = 0 | C=O | H | H | 1 | —NHCO₂CH₂Ph | H |
| 31 | 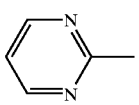 | N | N | 2 | m = 0 | n = 0 | C=O 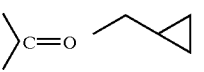 | H | H | 1 | —NHSO₂Ph | t-Bu |
| 32 | 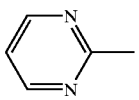 | N | N | 2 | m = 0 | n = 0 | C=O 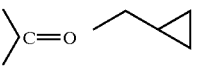 | H | H | 1 | —NHSO₂Ph | H |
| 33 | 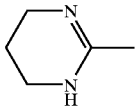 | N | N | 2 | m = 0 | n = 0 | C=O 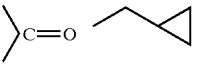 | H | H | 1 | —NHSO₂Ph | H |
| 34 | 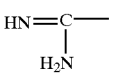 | N | N | 2 | m = 0 | n = 0 | C=O | H | H | 1 | —NHSO₂Ph | H |
| 35 | 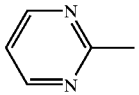 | N | N | 2 | m = 2;<br>3R-Me,<br>5S-Me | n = 0 | C=O | H | H | 1 | —NHSO₂Ph | t-Bu |
| 36 | 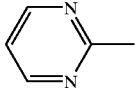 | N | N | 2 | m = 2;<br>3R-Me,<br>5S-Me | n = 0 | C=O | H | H | 1 | —NHSO₂Ph | H |

-continued

| | A | X | Z | p | R⁴ | R⁵ | Q | R⁶ | R⁷ | q | R⁸ | R⁹ |
|---|---|---|---|---|---|---|---|---|---|---|---|---|
| 37 | 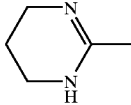 | N | N | 2 | m = 2;<br>3R-Me,<br>5S-Me | n = 0 | >C=O | H | H | 1 | —NHSO₂Ph | H |
| 38 |  | N | N | 2 | m = 0 | n = 0 | >C=O | H | H | 1 | —NHCO₂CH₂Ph | t-Bu |
| 39 | 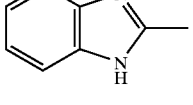 | N | N | 2 | m = 0 | n = 0 | >C=O | H | H | 1 | —NHCO₂CH₂Ph | H |
| 40 |  | N | N | 2 | m = 0 | n = 0 | >C=O | n-Pr | H | 1 | —NHSO₂Ph | t-Bu |
| 41 | 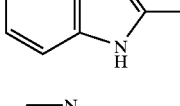 | N | N | 2 | m = 0 | n = 0 | >C=O | n-Pr | H | 1 | —NHSO₂Ph | H |
| 42 |  | N | N | 2 | m = 0 | n = 0 | >C=O | n-Pr | H | 1 | —NHSO₂Ph | H |
| 43 | 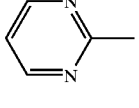 | N | N | 2 | m = 0 | n = 0 | >C=O | H | H | 1 | —NHBoc | H |
| 44 |  | N | N | 2 | m = 0 | n = 0 | >C=O | H | H | 1 | —N(Me)SO₂Ph | t-Bu |
| 45 | 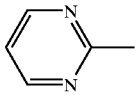 | N | N | 2 | m = 0 | n = 0 | >C=O | H | H | 1 | —N(Me)SO₂Ph | H |
| 46 |  | N | N | 2 | m = 0 | n = 0 | >C=O | H | H | 1 | —N(Me)SO₂Ph | H |
| 47 | 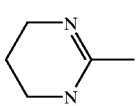 | N | N | 2 | m = 0 | n = 0 | >C=O | H | H | 1 | —N(Hex)SO₂Ph | t-Bu |
| 48 |  | N | N | 2 | m = 0 | n = 0 | >C=O | H | H | 1 | —N(Hex)SO₂Ph | H |
| 49 | 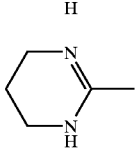 | N | N | 2 | m = 0 | n = 0 | >C=O | H | H | 1 | —N(Hex)SO₂Ph | H |

-continued

| | A | X | Z | p | R⁴ | R⁵ | Q | R⁶ | R⁷ | q | R⁸ | R⁹ |
|---|---|---|---|---|---|---|---|---|---|---|---|---|
| 50 | 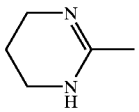 | N | N | 2 | m = 0 | n = 0 | C=O | H | H | 1 | —NHCO(CH$_2$)$_2$CONHOH | H |
| 51 | 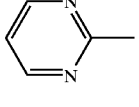 | N | N | 2 | m = 0 | n = 1; 3-F | C=O | H | H | 1 | —NHSO$_2$Ph | t-Bu |
| 52 | 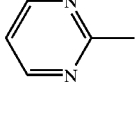 | N | N | 2 | m = 0 | n = 1; 3-F | C=O | H | H | 1 | —NHSO$_2$Ph | H |
| 53 | 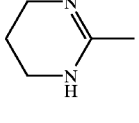 | N | N | 2 | m = 0 | n = 1; 3-F | C=O | H | H | 1 | —NHSO$_2$Ph | H |
| 54 | 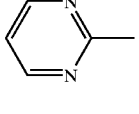 | N | N | 2 | m = 0 | n = 1; 2-F | C=O | H | H | 1 | —NHSO$_2$Ph | t-Bu |
| 55 | 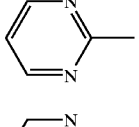 | N | N | 2 | m = 0 | n = 1; 2-F | C=O | H | H | 1 | —NHSO$_2$Ph | H |
| 56 | 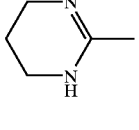 | N | N | 2 | m = 0 | n = 1; 2-F | C=O | H | H | 1 | —NHSO$_2$Ph | H |
| 57 | 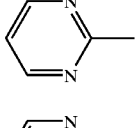 | N | N | 2 | m = 0 | n = 1; 3-Cl | C=O | H | H | 1 | —NHSO$_2$Ph | t-Bu |
| 58 | 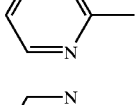 | N | N | 2 | m = 0 | n = 1; 3-Cl | C=O | H | H | 1 | —NHSO$_2$Ph | H |
| 59 | 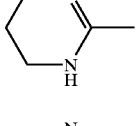 | N | N | 2 | m = 0 | n = 1; 3-Cl | C=O | H | H | 1 | —NHSO$_2$Ph | H |
| 60 | 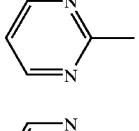 | N | N | 2 | m = 0 | n = 1; 2-Cl | C=O | H | H | 1 | —NHSO$_2$Ph | t-Bu |
| 61 | 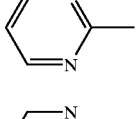 | N | N | 2 | m = 0 | n = 1; 2-Cl | C=O | H | H | 1 | —NHSO$_2$Ph | H |
| 62 | 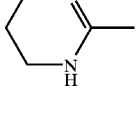 | N | N | 2 | m = 0 | n = 1; 2-Cl | C=O | H | H | 1 | —NHSO$_2$Ph | H |

-continued
| | A | X | Z | p | R4 | R5 | Q | R6 | R7 | q | R8 | R9 |
|---|---|---|---|---|---|---|---|---|---|---|---|---|
| 63 | 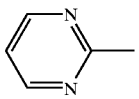 | N | N | 2 | m = 0 | n = 1; 3-NO2 |  | H | H | 1 | —NHSO2Ph | t-Bu |
| 64 | 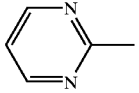 | N | N | 2 | m = 0 | n = 1; 3-NO2 |  | H | H | 1 | —NHSO2Ph | H |
| 65 | 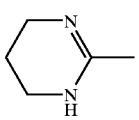 | N | N | 2 | m = 0 | n = 2; 2-Cl, 3-NH2 |  | H | H | 1 | —NHSO2Ph | H |
| 66 | 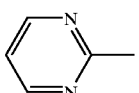 | N | N | 2 | m = 1; 3S-Me | n = 0 |  | H | H | 1 | —NHCO2CH2Ph | t-Bu |
| 67 | 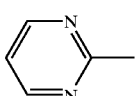 | N | N | 2 | m = 1; 3S-Me | n = 0 |  | H | H | 1 | —NHCO2CH2Ph | H |
| 68 | 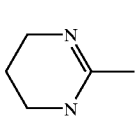 | N | N | 2 | m = 1; 3S-Me | n = 0 |  | H | H | 1 | —NH2 | H |
| 69 | 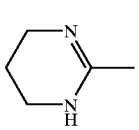 | N | N | 2 | m = 1; 3S-Me | n = 0 |  | H | H | 1 | —NHCO2CH2Ph | H |
| 70 | 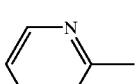 | N | N | 2 | m = 1; 3S-Me | n = 1; 3-F |  | H | H | 1 | —NHSO2Ph | t-Bu |
| 71 | 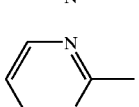 | N | N | 2 | m = 1; 3S-Me | n = 1; 3-F |  | H | H | 1 | —NHSO2Ph | H |
| 72 | 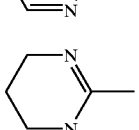 | N | N | 2 | m = 1; 3S-Me | n = 1; 3-F |  | H | H | 1 | —NHSO2Ph | H |
| 73 | 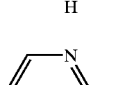 | N | N | 2 | m = 0 | n = 1; 3-F |  | H | H | 1 | —NHCO2CH2Ph | t-Bu |
| 74 | 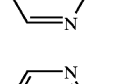 | N | N | 2 | m = 0 | n = 1; 3-F |  | H | H | 1 | —NHCO2CH2Ph | H |
| 75 | 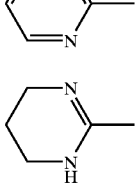 | N | N | 2 | m = 0 | n = 1; 3-F |  | H | H | 1 | —NH2 | H |

-continued

| | A | X | Z | p | R⁴ | R⁵ | Q | R⁶ | R⁷ | q | R⁸ | R⁹ |
|---|---|---|---|---|---|---|---|---|---|---|---|---|
| 76 | 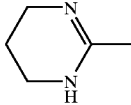 | N | N | 2 | m = 0 | n = 1; 3-F | >C=O | H | H | 1 | —NHCO₂CH₂Ph | H |
| 77 |  | N | N | 2 | m = 0 | n = 1; 3-F | >C=O | H | H | 1 | —NHEt | t-Bu |
| 78 | 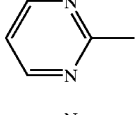 | N | N | 2 | m = 0 | n = 1; 3-F | >C=O | H | H | 1 | —NHEt | H |
| 79 |  | N | N | 2 | m = 0 | n = 1; 3-F | >C=O | H | H | 1 | —NHEt | H |
| 80 | 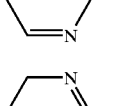 | N | N | 2 | m = 0 | n = 1; 3-F | >C=O | H | H | 1 | —NH₂ | t-Bu |
| 81 |  | N | N | 2 | m = 0 | n = 1; 3-F | >C=O | H | H | 1 | —NHSO₂Ph* | t-Bu |
| 82 | 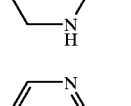 | N | N | 2 | m = 0 | n = 1; 3-F | >C=O | H | H | 1 | —NHSO₂Ph* | H |
| 83 |  | N | N | 2 | m = 0 | n = 1; 3-F | >C=O | H | H | 1 | —NHSO₂Ph* | H |
| 84 | 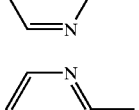 | N | N | 2 | m = 0 | n = 0 | >C=O | H | H | 1 | —NH₂ | t-Bu |
| 85 |  | N | N | 2 | m = 0 | n = 0 | >C=O | H | H | 1 | —NH₂ | H |
| 86 | 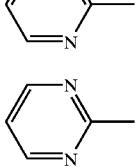 | N | N | 2 | m = 0 | n = 0 | >C=O | H | H | 1 | H | Et |
| 87 |  | N | N | 2 | m = 0 | n = 0 | >C=O | H | H | 1 | H | H |

Me: methyl,
Et: ethyl,
Pr: propyl,
Bu: butyl,
Hex: Hexyl,
Ph: phenyl,
Ph*: 2,4,6-trimethylphenyl,
Bn: benzyl,
Boc: t-butoxycarbonyl

What is claimed is:

1. A compound represented by formula (I) or a pharmaceutically acceptable salt or solvate thereof:

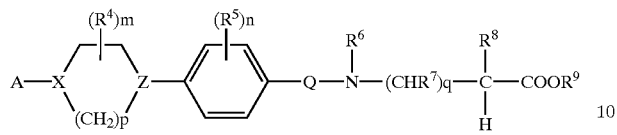   (I)

wherein

A represents (i) a saturated or unsaturated heterocyclic group represented by the following formula:

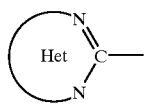

wherein Het represents pyrimidine, tetrahydropyrimidine, imidazole, or benzimidazole, which is optionally substituted by $C_{1-6}$ alkyl or amino optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group, or (ii) a group represented by formula

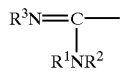

wherein $R^1$, $R^2$, and $R^3$, which may be the same or different, represent a hydrogen atom, $C_{1-6}$ alkyl, $C_{2-6}$ alkenyl or $C_{1-6}$ alkyl substituted by an unsaturated five- to seven-membered carbocyclic group, X and Z represent N;

$R^4$ represents $C_{1-6}$ alkyl or an oxygen atom;

$R^5$ represents $C_{1-6}$ alkyl, $C_{1-6}$ alkoxy, a halogen atom, amino or nitro, wherein $C_{1-6}$ alkyl is optionally substituted by $C_{1-6}$ alkoxy or hydroxyl;

Q represents >C=O or >$CH_2$;

$R^6$ represents a hydrogen atom, $C_{1-6}$ alkyl, $C_{2-6}$ alkenyl, or $C_{1-6}$ alkyl substituted by an unsaturated five- to seven-membered carbocyclic group;

$R^7$ represents a hydrogen atom, $C_{1-6}$ alkyl, $C_{2-6}$ alkenyl, $C_{2-6}$ alkynyl, or $C_{1-6}$ alkyl substituted by an unsaturated five- to seven-membered carbocyclic group;

$R^8$ represents a hydrogen atom, $C_{1-6}$ alkyl, $C_{2-6}$ alkenyl, $C_{1-6}$ alkyl substituted by an unsaturated five- to seven-membered carbocyclic group, or amino, wherein amino is optionally substituted by $C_{1-6}$ alkyl, $C_{1-6}$ alkoxycarbonyl, alkylsulfonyl, benzenesulfonyl in which the phenyl portion is optionally substituted by $C_{1-6}$ alkyl, phenyl optionally condensed with the phenyl portion, carboxyl, hydroxyl, nitro, amino, saturated or unsaturated five- to seven-membered carbocyclic group, $C_{1-6}$ alkylamino or a halogen atom, aralkyloxycarbonyl, or group —C(=O)—$(CH_2)_s$—C(=O)—$NHR^{11}$ wherein s is an integer of 0 to 4 and $R^{11}$ represents a hydrogen atom or hydroxyl;

$R^9$ represents a hydrogen atom or $C_{1-6}$ alkyl;

m is an integer of 0 to 2;

n is an integer of 0 or 1;

p is 2; and q is 1.

2. The compound according to claim 1, wherein A represents a group of formula

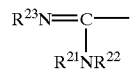

wherein $R^{21}$, $R^{22}$, and $R^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or $R^{21}$ and $R^{23}$ may together form group —$(CH_2)_3$—, group —$CHR^{24}CH_2CH_2$— wherein $R^{24}$ represents $C_{1-6}$ alkyl or amino optionally substituted by $C_{1-6}$ alkyl, $C_{1-6}$ alkoxycarbonyl, aralkyl, or aralkyloxycarbonyl, group —$CH_2CHR^{24}CH_2$— wherein $R^{24}$ is as defined above, group —$CH_2CH_2$—, group —$CHR^{24}CH_2$— wherein $R^{24}$ is as defined above, group —$CR^{25}$=$CR^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, or when $R^{21}$ and $R^{23}$ may together form group =CH—CH=CH—, then $R^{22}$ does not exist.

3. The compound according to claim 1, wherein

X and Z both represent N;

A represents a group of formula

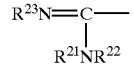

wherein $R^{21}$, $R^{22}$, and $R^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or $R^{21}$ and $R^{23}$ may together form group —$(CH_2)_3$—, group —$CHR^{24}CH_2CH_2$— wherein $R^{24}$ represents $C_{1-6}$ alkyl or amino optionally substituted by $C_{1-6}$ alkyl, $C_{1-6}$ alkoxycarbonyl, aralkyl, or aralkyloxycarbonyl, group —$CH_2CHR^{24}CH_2$— wherein $R^{24}$ is as defined above, group —$CH_2CH_2$—, group —$CHR^{24}CH_2$— wherein $R^{24}$ is as defined above, group —$CR^{25}$=$CR^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, or when $R^{21}$ and $R^{23}$ may together form group =CH—CH=CH—, then $R^{22}$ does not exist;

Q represents >C=O or >$CH_2$,

R⁶ represents a hydrogen atom, $C_{1-6}$ alkyl, or $C_{1-6}$ alkyl substituted by an unsaturated five- to seven-membered carbocyclic group, R⁷ represents a hydrogen atom or $C_{2-6}$ alkynyl;

R⁸ represents a hydrogen atom or amino, wherein amino is optionally substituted by $C_{1-6}$ alkyl, $C_{1-6}$ alkoxycarbonyl, benzenesulfonyl in which the phenyl portion is optionally substituted by $C_{1-6}$ alkyl; aralkyl, aralkyloxycarbonyl, or group —C(=O)—(CH₂)ₛ—C(=O)—NHR¹¹ wherein s is an integer of 0 to 4 and R¹¹ represents a hydrogen atom or hydroxyl;

m is an integer of 0 to 2;

n is an integer of 0 or 1; and q is 1.

4. The compound according to claim 1, which is selected from the group consisting of the following compounds, or a pharmaceutically acceptable salt or solvate thereof:

(1) t-butyl (2S)-benzenesulfonylamino-3-[4-{4-(pyrimidin-2-yl)-piperazin-1-yl}-benzoylamino]-propionate;

(2) (2S)-benzenesulfonylamino-3-[4-{4-(pyrimidin-2-yl)-piperazin-1-yl}-benzoylamino]-propionic acid;

(3) (2S)-benzenesulfonylamino-3-[4-{4-(1,4,5,6-tetrahydropyrimidin-2-yl)-piperazin-1-yl}-benzoyl-amino]-propionic acid;

(4) t-butyl (2S)-benzenesulfonylamino-3-[4-{3-methyl-4-(pyrimidin-2-yl)-piperazin-1-yl}-benzoylamino]-propionate;

(5) (2S)-benzenesulfonylamino-3-[4-{3-methyl-4-(pyrimidin-2-yl)-piperazin-1-yl}-benzoylamino]-propionic acid;

(6) (2S)-benzenesulfonylamino-3-[4-{3-methyl-4-(1,4,5,6-tetrahydropyrimidin-2-yl)-piperazin-1-yl}-benzoylamino]-propionic acid;

(7) t-butyl (2S)-benzenesulfonylamino-3-[4-{(3R)-methyl-4-(pyrimidin-2-yl)-piperazin-1-yl} -benzoylamino]-propionate;

(8) (2S)-benzenesulfonylamino-3-[4-{(3R)-methyl-4-(pyrimidin-2-yl)-piperazin-1-yl}-benzoylamino]-propionic acid;

(9) (2S)-benzenesulfonylamino-3-[4-{(3R)-methyl-4-(1,4,5,6-tetrahydropyrimidin-2-yl)-piperazin-1-yl}-benzoylamino]-propionic acid;

(10) t-butyl (2S)-benzenesulfonylamino-3-[4-{(3S)-methyl-4-(pyrimidin-2-yl)-piperazin-1-yl }-benzoylamino]-propionate;

(11) (2S)-benzenesulfonylamino-3-[4-{(3S)-methyl-4-(pyrimidin-2-yl)-piperazin-1-yl}-benzoylamino]-propionic acid;

(12) (2S)-benzenesulfonylamino-3-[4-{(3S)-methyl-4-(1,4,5,6-tetrahydropyrimidin-2-yl)-piperazin-1-yl}-benzoylamino]-propionic acid;

(13) t-butyl (2S)-benzenesulfonylamino-3-[4-{4-(1H-benzimidazol-2-yl)-piperazin-1-yl}-benzoylamino]-propionate;

(14) (2S)-benzenesulfonylamino-3-[4-{4-(1H-benzimidazol-2-yl)-piperazin-1-yl}-benzoylamino]-propionic acid;

(15) ethyl (3S)-[4-{4-(pyrimidin-2-yl)-piperazin-1-yl}-benzoylamino]-pent-4-ynate; (19) (3S)-[4-{4-(pyrimidin-2-yl)-piperazin-1-yl}-benzoylamino]-pent-4-ynic acid; (20) t-butyl (2S)-benzenesulfonylamino-3-[4-{4-(pyrimidin-2-yl)-piperazin-1-yl}-benzylamino]-propionate;

(16) (2S)-benzenesulfonylamino-3-[4-{4-(pyrimidin-2-yl)-piperazin-1-yl}-benzylamino]-propionic acid;

(17) t-butyl (2S)-benzenesulfonylamino-3-[4-{4-(pyrimidin-2-yl)-piperazin-1-yl}-benzylamino]-propionate;

(18) (2S)-benzenesulfonylamino-3-[4{4-(pyrimidin-2-yl)-piperazin-1-yl}-benzylamino]-propionic acid;

(19) (2S)-benzenesulfonylamino-3-{4-[4-(1,4,5,6-tetrahydropyrimidin-2-yl)-piperazin-1-yl]-benzylamino}-propionic acid;

(20) (2S)-benzenesulfonylamino-3-[methyl-[4-{4-(pyrimidin-2-yl)-piperazin-1-yl}-benzyl]-amino]-propionic acid;

(21) (2S)-benzenesulfonylamino-3-[methyl-[4-{4-(1,4,5,6-tetrahydropyrimidin-2-yl)-piperazin-1-yl}-benzyl]-amino]-propionic acid;

(22) (2S)-benzenesulfonylamino-3-[benzyl-[4-{4-(pyrimidin-2-yl)-piperazin-1-yl}-benzyl]-amino]-propionic acid;

(23) (2S)-benzenesulfonylamino-3-[benzyl-[4-{4-(1,4,5,6-tetrahydropyrimidin-2-yl)-piperazin-1-yl}-benzyl]-amino]-propionic acid;

(24) t-butyl (2S)-benzyloxycarbonylamino-3-[4-{4-(pyrimidin-2-yl)-piperazin-1-yl}-benzoylamino]-propionate;

(25) (2S)-benzyloxycarbonylamino-3-[4{4-(pyrimidin-2-yl)-piperazin-1-yl}-benzoylamino]-propionic acid;

(26) (2S)-amino-3-[4-{4-(1,4,5,6-tetrahydropyrimidin-2-yl)-piperazin-1-yl}-benzoylamino]-propionic acid;

(27) (2S)-benzyloxycarbonylamino-3-[4-{4-(1,4,5,6-tetrahydropyrimidin-2-yl)-piperazin-1-yl}-benzoylamino]-propionic acid;

(28) t-butyl (2S)-benzenesulfonylamino-3-[cyclopropylmethyl-[4-{4-(pyrimidin-2-yl)-piperazin-1-yl}-benzoyl]-amino]-propionate;

(29) (2S)-benzenesulfonylamino-3-[cyclopropylmethyl-[4-{4-(pyrimidin-2-yl)-piperazin-1-yl}-benzoyl]-amino]-propionic acid;

(30) (2S)-benzenesulfonylamino-3-[cyclopropylmethyl-[4-{4-(1,4,5,6-tetrahydropyrimidin-2-yl)-piperazin-1-yl}-benzoyl]-amino]-propionic acid;

(31) (2S)-benzenesulfonylamino-3-[4-{4-(carbamimidoyl)-piperazin-1-yl}-benzoylamino]-propionic acid;

(32) t-butyl (2S)-benzenesulfonylamino-3-[4-{cis-3,5-dimethyl-4-(pyrimidin-2-yl)-piperazin-1-yl}-benzoylamino]-propionate;

(33) (2S)-benzenesulfonylamino-3-[4-{cis-3,5-dimethyl-4-(pyrimidin-2-yl)-piperazin-1-yl}-benzoylamino]-propionic acid;

(34) (2S)-benzenesulfonylamino-3-[4-{cis-3,5-dimethyl-4-(1,4,5,6-tetrahydropyrimidin-2-yl)-piperazin-1-yl}-benzoylamino]-propionic acid;

(35) t-butyl 3-[4-{4-(1H-benzimidazol-2-yl)-piperazin-1-yl}-benzoylamino]-(2S)-benzyloxycarbonylamino-propionate;

(36) 3-[4-{4-(1H-benzimidazol-2-yl)-piperazin-1-yl}-benzoylamino]-(2S)-benzyloxycarbonylamino-propionic acid;

(37) t-butyl (2S)-benzenesulfonylamino-3-[propyl-[4-{4-(pyrimidin-2-yl)-piperazin-1-yl}-benzoyl]-amino]-propionate;

(38) (2S)-benzenesulfonylamino-3-[propyl-[4-{4-(pyrimidin-2-yl)-piperazin-1-yl}-benzoyl]-amino]-propionic acid;

(39) (2S)-benzenesulfonylamino-3-[propyl-[4-{4-(1,4,5,6-tetrahydropyrimidin-2-yl)-piperazin-1-yl}-benzoyl]-amino]-propionic acid;

(40) (2S)-t-butoxycarbonylamino-3-[4-{4-(1,4,5,6-tetrahydropyrimidin-2-yl)-piperazin-1-yl}-benzoylamino]-propionic acid;

(41) t-butyl 2-(benzenesulfonyl-methyl-amino)-3-[4-{4-(pyrimidin-2-yl)-piperazin-1-yl}-benzoylamino]-propionate;
(42) 2-(benzenesulfonyl-methyl-amino)-3-[4-{4-(pyrimidin-2-yl)-piperazin-1-yl}-benzoylamino]-propionic acid;
(43) 2-(benzenesulfonyl-methyl-amino)-3-[4-{4-(1,4,5,6-tetrahydropyrimidin-2-yl)-piperazin-1-yl}-benzoylamino]-propionic acid;
(44) t-butyl 2-(benzenesulfonyl-hexyl-amino)-3-[4-{4-(pyrimidin-2-yl)-piperazin-1-yl}-benzoylamino]-propionate;
(45) 2-(benzenesulfonyl-hexyl-amino)-3-[4-{4-(pyrimidin-2-yl)-piperazin-1-yl}-benzoylamino]-propionic acid;
(46) 2-(benzenesulfonyl-hexyl-amino)-3-[4-{4-(1,4,5,6-tetrahydropyrimidin-2-yl)-piperazin-1-yl}-benzoylamino]-propionic acid;
(47) (2S)-(3-hydroxycarbamoyl-propionylamino)-3-[4-{4-(1,4,5,6-tetrahydropyrimidin-2-yl)-piperazin-1-yl}-benzoylamino]-propionic acid;
(48) t-butyl (2S)-benzenesulfonylamino-3-[3-fluoro-4-{4-(pyrimidin-2-yl)-piperazin-1-yl}-benzoylamino]-propionate;
(49) (2S)-benzenesulfonylamino-3-[3-fluoro-4-{4-(pyrimidin-2-yl)-piperazin-1-yl}-benzoylamino]-propionic acid;
(50) (2S)-benzenesulfonylamino-3-[3-fluoro-4-{4-(1,4,5,6-tetrahydropyrimidin-2-yl)-piperazin-1-yl}-benzoylamino]-propionic acid;
(51) t-butyl (2S)-benzenesulfonylamino-3-[2-fluoro-4-{4-(pyrimidin-2-yl)-piperazin-1-yl}-benzoylamino]-propionate;
(52) (2S)-benzenesulfonylamino-3-[2-fluoro-4-{4-(pyrimidin-2-yl)-piperazin-1-yl}-benzoylamino]-propionic acid;
(53) (2S)-benzenesulfonylamino-3-[2-fluoro-4-{4-(1,4,5,6-tetrahydropyrimidin-2-yl)-piperazin-1-yl}-benzoylamino]-propionic acid;
(54) t-butyl (2S)-benzenesulfonylamino-3-[3-chloro-4-{4-(pyrimidin-2-yl)-piperazin-1-yl}-benzoylamino]-propionate;
(55) (2S)-benzenesulfonylamino-3-[2-chloro-4-{4-(pyrimidin-2-yl)-piperazin-1-yl}-benzoylamino]-propionic acid;
(56) (2S)-benzenesulfonylamino-3-[3-chloro-4-{4-(1,4,5,6-tetrahydropyrimidin-2-yl)-piperazin-1-yl}-benzoylamino]-propionic acid;
(57) t-butyl (2S)-benzenesulfonylamino-3-[2-chloro-4-{4-(pyrimidin-2-yl)-piperazin-1-yl}-benzoylamino]-propionate;
(58) (2S)-benzenesulfonylamino-3-[2-chloro-4-{4-(pyrimidin-2-yl)-piperazin-1-yl}-benzoylamino]-propionic acid;
(59) (2S)-benzenesulfonylamino-3-[2-chloro-4-{4-(1,4,5,6-tetrahydropyrimidin-2-yl)-piperazin-1-yl}-benzoylamino]-propionic acid;
(60) t-butyl (2S)-benzenesulfonylamino-3-[3-nitro-4-{4-(pyrimidin-2-yl)-piperazin-1-yl}-benzoylamino]-propionate;
(61) (2S)-benzenesulfonylamino-3-[2-nitro-4-{4-(pyrimidin-2-yl)-piperazin-1-yl}-benzoylamino]-propionic acid;
(62) t-butyl (2S)-benzyloxycarbonylamino-3-[4-{(3S)-methyl-4-(pyrimidin-2-yl)-piperazin-1-yl}-benzoylamino]-propionate;
(63) (2S)-benzyloxycarbonylamino-3-[4-{(3S)-methyl-4-(pyrimidin-2-yl)-piperazin-1yl}-benzoylamino]-propionic acid;
(64) (2S)-amino-3-[4-{(3S)-methyl-4-(1,4,5,6-tetrahydropyrimidin-2-yl)-piperazin-1-yl}-benzoylamino]-propionic acid;
(65) (2S)-benzyloxycarbonylamino-3-[4-{(3S)-methyl-4-(1,4,5,6-tetrahydropyrimidin-2-yl)-piperazin-1-yl}-benzoylamino]-propionic acid;
(66) t-butyl (2S)-benzenesulfonylamino-3-[3-fluoro-4-{(3S)-methyl-4-(pyrimidin-2-yl)-piperazin-1-yl}-benzoylamino]-propionate;
(67) (2S)-benzenesulfonylamino-3-[3-fluoro-4-{(3S)-methyl-4-(pyrimidin-2-yl)-piperazin-1-yl}-benzoylamino]-propionic acid;
(68) (2S)-benzenesulfonylamino-3-[3-fluoro-4-{(3S)-methyl-4-(1,4,5,6-tetrahydropyrimidin-2-yl)-piperazin-1-yl}-benzoylamino]-propionic acid;
(69) t-butyl (2S)-benzyloxycarbonylamino-3-[3-fluoro-4-{4-(pyrimidin-2-yl)-piperazin-1-yl}-benzoylamino]-propionate;
(70) (2S)-benzyloxycarbonylamino-3-[3-fluoro-4-{4-(pyrimidin-2-yl)-piperazin-1-yl}-benzoylamino]-propionic acid;
(71) (2S)-amino-3-[3-fluoro-4-{4-(1,4,5,6-tetrahydropyrimidin-2-yl)-piperazin-1-yl}-benzoylamino]-propionic acid;
(72) (2S)-benzyloxycarbonylamino-3-[3-fluoro-4-{4-(1,4,5,6-tetrahydropyrimidin-2-yl)-piperazin-1-yl}-benzoylamino]-propionic acid;
(73) t-butyl (2S)-ethylamino-3-[3-fluoro-4-{4-(pyrimidin-2-yl)-piperazin-1-yl}-benzoylamino]-propionate;
(74) (2S)-ethylamino-3-[3-fluoro-4-{4-(pyrimidin-2-yl)-piperazin-1-yl}-benzoylamino]-propionic acid;
(75) (2S)-ethylamino-3-[3-fluoro-4-{4-(1,4,5,6-tetrahydropyrimidin-2-yl)-piperazin-1-yl}-benzoylamino]-propionic acid;
(76) t-butyl (2S)-amino-3-[3-fluoro-4-{4-(pyrimidin-2-yl)-piperazin-1-yl}-benzoylamino]-propionate;
(77) t-butyl 3-[3-fluoro-4-{4-(pyrimidin-2-yl)-piperazin-1-yl}-benzoylamino](S2S)-(2,4,6-trimethyl-benzenesulfonylamino)-propionate;
(78) 3-[3-fluoro-4-{4-(pyrimidin-2-yl)-piperazin-1-yl}-benzoylamino]-(2S)-(2,4,6-trimethyl-benzenesulfonylamino)-propionic acid;
(79) 3-[3-fluoro-4-{4-(1,4,5,6-tetrahydropyrimidin-2-yl)-piperazin-1-yl}-benzoylamino]-(2S)-(2,4,6-trimethyl-benzenesulfonylamino)-propionic acid;
(80) t-butyl (2S)-amino-3-[4-{4-(pyrimidin-2-yl)-piperazin-1-yl}-benzoylamino]-propionate;
(81) (2S)-amino-3-[4-{4-(pyrimidin-2-yl)-piperazin-1-yl}-benzoylamino]-propionic acid;
(82) ethyl 3-[4-{4-(pyrimidin-2-yl)-piperazin-1-yl}-benzoylamino]-propionate; and
(83) 3-[4-{4-(pyrimidin-2-yl)-piperazin-1-yl}-benzoylamino]-propionic acid.

5. A pharmaceutical composition comprising as active ingredient the compound according to any one of claims 1 to 3 or a pharmaceutically acceptable salt or solvate thereof.

6. A method for treating an integrin $\alpha_v\beta_3$-mediated disease selected from the group consisting of cardiovascular diseases, angiogenesis-related diseases, cerebrovascular diseases, cancers and metastasis thereof, immunological diseases, and osteopathy, comprising the step of administering an effective amount of a compound represented by formula (I) or a pharmaceutically acceptable salt or solvate thereof:

(I)

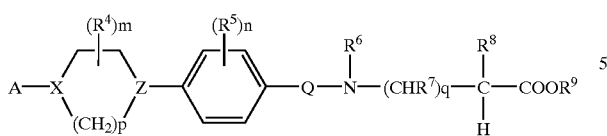

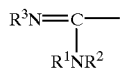

wherein

A represents (i) a saturated or unsaturated heterocyclic group selected from the group consisting of pyrimidine, tetrahydropyrimidine, imidazole, and benzimidazole, which is optionally substituted by $C_{1-6}$ alkyl or amino optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group, or (ii) a group represented by formula $$R^3N=C-\underset{R^1NR^2}{|}$$

wherein
R$^1$, R$^2$, and R$^3$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, X and Z represent N;

R$^4$ represents $C_{1-6}$ alkyl or an oxygen atom;

R$^5$ represents $C_{1-6}$ alkyl, $C_{1-6}$ alkoxy, a halogen atom, amino, or nitro, wherein $C_{1-6}$ alkyl is optionally substituted by $C_{1-6}$ alkoxy, or hydroxyl;

Q represents >C=O, or >CH$_2$;

R$^6$ represents a hydrogen atom, $C_{1-6}$ alkyl, $C_{2-6}$ alkenyl, or $C_{1-6}$ alkyl substituted by an unsaturated five- to seven-membered carbocyclic group;

R$^7$ represents a hydrogen atom, $C_{1-6}$ alkyl, $C_{2-6}$ alkenyl, $C_{2-6}$ alkynyl, or $C_{1-6}$ alkyl substituted by an unsaturated five- to seven-membered carbocyclic group;

R$^8$ represents a hydrogen atom, $C_{1-6}$ alkyl, $C_{2-6}$ alkenyl, $C_{1-6}$ alkyl substituted by an unsaturated five- to seven-membered carbocyclic group, or amino, wherein amino is optionally substituted by $C_{1-6}$ alkyl, $C_{1-6}$ alkoxycarbonyl, alkylsulfonyl, benzenesulfonyl in which the phenyl portion is optionally substituted by $C_{1-6}$ alkyl, phenyl optionally condensed with the phenyl portion, carboxyl, hydroxyl, nitro, amino, saturated or unsaturated five- to seven-membered carbocyclic group, $C_{1-6}$ alkylamino or a halogen atom, aralkyloxycarbonyl, or group —C(=O)—(CH$_2$)$_s$—C(=O)—NHR$^{11}$ wherein s is an integer of 0 to 4 and R$^{11}$ represents a hydrogen atom or hydroxyl;

R$^9$ represents a hydrogen atom or $C_{1-6}$ alkyl;

m is an integer of 0 to 2;

n is an integer of 0 or 1;

p is 2; and q is 1 together with a pharmaceutically acceptable carrier, to mammals including humans.

7. A compound represented by formula (III'):

(III')

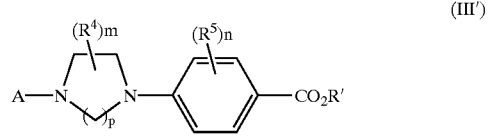

wherein
A represents (i) a saturated or unsaturated heterocyclic group represented by the following formula:

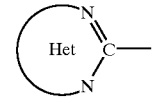

wherein Het represents pyrimidine, tetrahydropyrimidine, imidazole, or benzimidazole, which is optionally substituted by $C_{1-6}$ alkyl or amino optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxy carbonyl substituted by an unsaturated five- to seven-membered carbocyclic group, or (ii) a group represented by formula

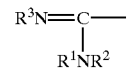

wherein
R$^1$, R$^2$, and R$^3$, which may be the same or different, represent a hydrogen atom, $C_{1-6}$ alkyl, $C_{2-6}$ alkenyl, or aralkyl;

R$^4$ represents $C_{1-6}$ alkyl, or an oxygen atom;

R$^5$ represents $C_{1-6}$ alkyl, $C_{1-6}$ alkoxy, a halogen atom, amino, or nitro, wherein $C_{1-6}$ alkyl is optionally substituted by $C_{1-6}$ alkoxy, or hydroxyl;

m is an integer of 0 to 2;

n is an integer of 0 or 1;

p is 2; and

R' represents hydrogen, methyl, ethyl, propyl, butyl, or benzyl, or —COOR' represents —CN.

8. The method according to claim 6, wherein A in formula (I) represents a group of formula

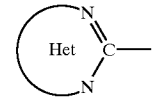

wherein
Het represents a saturated or unsaturated heterocyclic group selected from the group consisting of pyrimidine, tetrahydropyrimidine, imidazole, and benzimidazole, which is optionally substituted by $C_{1-6}$ alkyl or amino, the amino being optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group.

9. The method according to claim 6, wherein A in formula (I) represents a group of formula

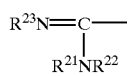

wherein
  $R^{21}$, $R^{22}$, and $R^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or
  $R^{21}$ and $R^{23}$ may together form
    group —(CH$_2$)$_3$—,
    group —CHR$^{24}$CH$_2$CH$_2$— wherein $R^{24}$ represents $C_{1-6}$ alkyl or amino optionally substituted by $C_{1-6}$ alkyl, $C_{1-6}$ alkoxycarbonyl, aralkyl, or aralkyloxycarbonyl,
    group —CH$_2$CHR$^{24}$CH$_2$— wherein $R^{24}$ is as defined above,
    group —CH$_2$CH$_2$—,
    group —CHR$^{24}$CH$_2$— wherein $R^{24}$ is as defined above,
    group —CR$^{25}$═CR$^{26}$— wherein $R^{25}$ and $R^{26}$, which may be the same or different, represent a hydrogen atom or $C_{1-6}$ alkyl, or $R^{25}$ and $R^{26}$ may together form —CH═CH—CH═CH—, or when $R^{21}$ and $R^{23}$ may together form
    group ═CH—CH═CH—, then $R^{22}$ does not exist.

10. The method according to claim 6, wherein
X and Z both represent N;
A represents a group of formula

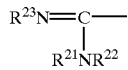

wherein
  $R^{21}$, $R^{22}$, and $R^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or
  $R^{21}$ and $R^{23}$ may together form
    group —(CH$_2$)$_3$—,
    group —CHR$^{24}$CH$_2$CH$_2$— wherein $R^{24}$ represents $C_{1-6}$ alkyl or amino optionally substituted by $C_{1-6}$ alkyl, $C_{1-6}$ alkoxycarbonyl, aralkyl, or aralkyloxycarbonyl,
    group —CH$_2$CHR$^{24}$CH$_2$— wherein $R^{24}$ is as defined above,
    group —CH$_2$CH$_2$—,
    group —CHR$^{24}$CH$_2$— wherein $R^{24}$ is as defined above,
    group —CR$^{25}$═CR$^{26}$— wherein $R^{25}$ and $R^{26}$, which may be the same or different, represent a hydrogen atom or $C_{1-6}$ alkyl, or $R^{25}$ and $R^{26}$ may together form —CH═CH—CH═CH—, or when $R^{21}$ and $R^{23}$ may together form
    group ═CH—CH═CH—, then $R^{22}$ does not exist.
Q represents >C═O or >CH$_2$;
$R^6$ represents a hydrogen atom, $C_{1-6}$ alkyl, or $C_{1-6}$ alkyl substituted by an unsaturated five- to seven-membered carbocyclic group;
$R^7$ represents a hydrogen atom or $C_{2-6}$ alkynyl;
$R^8$ represents a hydrogen atom or amino, wherein amino is optionally substituted by $C_{1-6}$ alkyl, $C_{1-6}$ alkoxycarbonyl, benzenesulfonyl in which the phenyl portion is optionally substituted by $C_{1-6}$ alkyl; aralkyl, aralkyloxycarbonyl, or group —C(═O)—(CH$_2$)$_s$—C(═O)—NHR$^{11}$ wherein s is an integer of 0 to 4 and $R^{11}$ represents a hydrogen atom or hydroxyl;
m is an integer of 0 to 2;
n is an integer of 0 or 1; and
q is 1.

11. A method for treating platelet thrombosis or thromboembolism, the improvement of peripheral circulating blood stream, the inhibition of blood clotting during extracorporeal circulation, or the treatment of thrombotic thrombocytopenic purpura or hemolytic uremic syndrome, comprising the step of administering an effective amount of a compound represented by formula (I) or a pharmaceutically acceptable salt or solvate thereof:

(I)

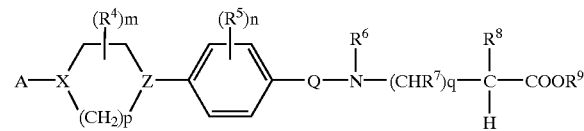

wherein
A represents (i) a saturated or unsaturated heterocyclic group selected from the group consisting of pyrimidine, tetrahydropyrimidine, imidazole, and benzimidazole, which is optionally substituted by $C_{1-6}$ alkyl or amino optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group, or (ii) a group represented by formula

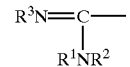

wherein
  $R^1$, $R^2$, and $R^3$, which may be the same or different, represent a hydrogen atom, $C_{1-6}$ alkyl, $C_{2-6}$ alkenyl, or aralkyl;
X and Z represent N;
$R^4$ represents $C_{1-6}$ alkyl, or an oxygen atom;
$R^5$ represents $C_{1-6}$ alkyl, $C_{1-6}$ alkoxy, a halogen atom, amino, or nitro, wherein $C_{1-6}$ alkyl is optionally substituted by $C_{1-6}$ alkoxy, or hydroxyl;
Q represents >C═O, or >CH$_2$;
$R^6$ represents a hydrogen atom, $C_{1-6}$ alkyl, $C_{2-6}$ alkenyl, or $C_{1-6}$ alkyl substituted by an unsaturated five- to seven-membered carbocyclic group;
$R^7$ represents a hydrogen atom, $C_{1-6}$ alkyl, $C_{2-6}$ alkenyl, $C_{2-6}$ alkynyl, aralkyl, or amino, wherein $C_{1-6}$ alkyl, $C_{2-6}$ alkenyl, $C_{2-6}$ alkynyl or $C_{1-6}$ alkyl substituted by an unsaturated five- to seven-membered carbocyclic group;
$R^8$ represents a hydrogen atom, $C_{1-6}$ alkyl, $C_{2-6}$ alkenyl, $C_{1-6}$ alkyl substituted by an unsaturated five- to seven-membered carbocyclic group, or amino, wherein amino is optionally substituted by $C_{1-6}$ alkyl, $C_{1-6}$ alkoxycarbonyl, alkylsulfonyl, benzenesulfonyl in which the phenyl portion is optionally substituted by $C_{1-6}$ alkyl, phenyl optionally condensed with the phenyl portion, carboxyl, hydroxyl, nitro, amino, saturated or unsaturated five- to seven-membered carbocyclic group, $C_{1-6}$ alkylamino or a halogen atom, aralkyloxycarbonyl, or group —C(=O)—(CH$_2$)$_s$—C(=O)—NHR$^{11}$ wherein s is an integer of 0 to 4 and R$^{11}$ represents a hydrogen atom or hydroxyl;

R$^9$ represents a hydrogen atom or $C_{1-6}$ alkyl;

m is an integer of 0 to 2;

n is an integer of 0 or 1;

p is 2; and q is 1 together with a pharmaceutically acceptable carrier, to mammals including humans.

12. The method according to claim 11, wherein A in formula (I) represents a group of formula

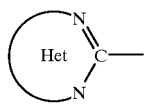

wherein

Het represents a saturated or unsaturated heterocyclic group selected from the group consisting of pyrimidine, tetrahydropyrimidine, imidazole, and benzimidazole, which is optionally substituted by $C_{1-6}$ alkyl or amino, the amino being optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group.

13. The method according to claim 11, wherein A in formula (I) represents a group of formula

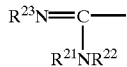

wherein

R$^{21}$, R$^{22}$, R$^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or R$^{21}$ and R$^{23}$ may together form group —(CH$_2$)$_3$—, group —CHR$^{24}$CH$_2$CH$_2$— wherein R$^{24}$ represents $C_{1-6}$ alkyl or amino optionally substituted by $C_{1-6}$ alkyl, $C_{1-6}$ alkoxycarbonyl, aralkyl, or aralkyloxycarbonyl, group —CH$_2$CHR$^{24}$C$_2$— wherein R$^{24}$ is as defined above, group —CH$_2$CH$_2$—, group —CHR$^{24}$CH$_2$— wherein R$^{24}$ is as defined above, group —CR$^{25}$=CR$^{26}$— wherein R$^{25}$ and R$^{26}$, which may be the same or different, represent a hydrogen atom or $C_{1-6}$ alkyl, or R$^{25}$ and R$^{26}$ may together form —CH=CH—CH=CH—, or when R$^{21}$ and R$^{23}$ may together form group =CH—CH=CH—, then R$^{22}$ does not exist.

14. The method according to claim 11, wherein X and Z both represent N;

A represents a group of formula

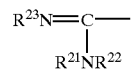

wherein

R$^{21}$, R$^{22}$, and R$^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or R$^{21}$ and R$^{23}$ may together form group —(CH$_2$)$_3$—, group —CHR$^{24}$CH$_2$CH$_2$— wherein R$^{24}$ represents $C_{1-6}$ alkyl or amino optionally substituted by $C_{1-6}$ alkyl, $C_{1-6}$ alkoxycarbonyl, aralkyl, or aralkyloxycarbonyl, group —CH$_2$CHR$^{24}$CH$_2$— wherein R$^{24}$ is as defined above, group —CH$_2$CH$_2$—, group —CHR$^{24}$CH$_2$— wherein R$^{24}$ is as defined above, group —CR$^{25}$=CR$^{26}$— wherein R$^{25}$ and R$^{26}$, which may be the same or different, represent a hydrogen atom or $C_{1-6}$ alkyl, or R$^{25}$ and R$^{26}$ may together form —CH=CH—CH=CH—, or when R$^{21}$ and R$^{23}$ may together form group =CH—CH=CH—, then R$^{22}$ does not exist, Q represents >C=O or >CH$_2$;

R$^6$ represents a hydrogen atom, $C_{1-6}$ alkyl, or $C_{1-6}$ alkyl substituted by an unsaturated five- to seven-membered carbocyclic group;

R$^7$ represents a hydrogen atom or $C_{2-6}$ alkynyl;

R$^8$ represents a hydrogen atom or amino, wherein amino is optionally substituted by $C_{1-6}$ alkyl, $C_{1-6}$ alkoxycarbonyl, benzenesulfonyl in which the phenyl portion is optionally substituted by $C_{1-6}$ alkyl; aralkyl, aralkyloxycarbonyl, or group —C(=O)—(CH$_2$)$_s$—C(=O)—NHR$^{11}$ wherein s is an integer of 0 to 4 and R$^{11}$ represents a hydrogen atom or hydroxyl;

m is an integer of 0 to 2;

n is an integer of 0 or 1; and q is 1.

15. A method for inhibiting platelet aggregation, comprising the step of administering an effective amount of a compound represented by formula (I) or a pharmaceutically acceptable salt or solvate thereof:

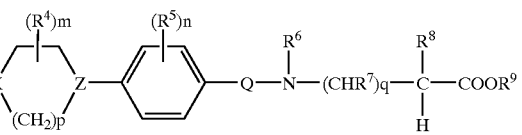

(I)

wherein

A represents (i) a saturated or unsaturated heterocyclic group selected from the group consisting of pyrimidine, tetrahydropyrimidine, imidazole, and benzimidazole, which is optionally substituted by $C_{1-6}$ alkyl or amino optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group, or (ii) a group represented by formula

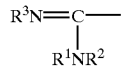

wherein
$R^1$, $R^2$, and $R^3$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group;
X and Z represent N;
$R^4$ represents $C_{1-6}$ alkyl, or an oxygen atom;
$R^5$ represents $C_{1-6}$ alkyl, $C_{1-6}$ alkoxy, a halogen atom, amino, or nitro, wherein $C_{1-6}$ alkyl is optionally substituted by $C_{1-6}$ alkoxy, or hydroxyl;
Q represents >C=O, or >$CH_2$;
$R^6$ represents a hydrogen atom, $C_{1-6}$ alkyl, $C_{2-6}$ alkenyl, or $C_{1-6}$ alkyl substituted by an unsaturated five- to seven-membered carbocyclic group;
$R^7$ represents a hydrogen atom, $C_{1-6}$ alkyl, $C_{2-6}$ alkenyl, $C_{2-6}$ alkynyl, or $C_{1-6}$ alkyl substituted by an unsaturated five- to seven-membered carbocyclic group;
$R^8$ represents a hydrogen atom, $C_{1-6}$ alkyl, $C_{2-6}$ alkenyl, $C_{1-6}$ alkyl substituted by an unsaturated five- to seven-membered carbocyclic group, or amino, wherein amino is optionally substituted by $C_{1-6}$ alkyl, $C_{1-6}$ alkoxycarbonyl, alkylsulfonyl, benzenesulfonyl in which the phenyl portion is optionally substituted by $C_{1-6}$ alkyl, phenyl optionally condensed with the phenyl portion, carboxyl, hydroxyl, nitro, amino, saturated or unsaturated five- to seven-membered carbocyclic group, $C_{1-6}$ alkylamino or a halogen atom, aralkyloxycarbonyl, or group —C(=O)—$(CH_2)_s$—C(=O)—$NHR^{11}$ wherein s is an integer of 0 to 4 and $R^{11}$ represents a hydrogen atom or hydroxyl;
$R^9$ represents a hydrogen atom or $C_{1-6}$ alkyl;
m is an integer of 0 to 2;
n is an integer of 0 or 1;
p is 2; and
q is 0 or 1
together with a pharmaceutically acceptable carrier, to mammals including humans.

16. The method according to claim 15, wherein A in formula (I) represents a group of formula

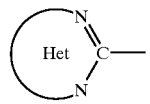

wherein
Het represents a saturated or unsaturated heterocyclic group selected from the group consisting of pyrimidine, tetrahydropyrimidine, imidazole, and benzimidazole, which is optionally substituted by $C_{1-6}$ alkyl or amino, the amino being optionally substituted by $C_{1-6}$ alkyl, $C_{1-6}$ alkyl substituted by an unsaturated five- to seven-membered carbocyclic group, $C_{1-6}$ alkoxycarbonyl, or $C_{1-6}$ alkoxycarbonyl substituted by an unsaturated five- to seven-membered carbocyclic group,.

17. The method according to claim 15, wherein A in formula (I) represents a group of formula

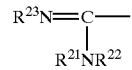

wherein
$R^{21}$, $R^{22}$, and $R^{23}$, which may be the same or different, represent a hydrogen atom, $C_{1-6}$ alkyl, $C_{2-6}$ alkenyl, or $C_{1-6}$ alkyl substituted by an unsaturated five- to seven-membered carbocyclic group, or
$R^{21}$ and $R^{23}$ may together form
group —$(CH_2)_3$—,
group —$CHR^{24}CH_2CH_2$— wherein $R^{24}$ represents $C_{1-6}$ alkyl or amino optionally substituted by $C_{1-6}$ alkyl, $C_{1-6}$ alkoxycarbonyl, aralkyl, or aralkyloxycarbonyl,
group —$CH_2CHR^{24}CH_2$— wherein $R^{24}$ is as defined above,
group —$CH_2CH_2$—,
group —$CHR^{24}CH_2$— wherein $R^{24}$ is as defined above,
group —$CR^{25}$=$CR^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, or when $R^{21}$ and $R^{23}$ may together form
group =CH—CH=CH—, then $R^{22}$ does not exist.

18. The method according to claim 15, wherein
X and Z both represent N;
A represents a group of formula

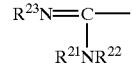

wherein
$R^{21}$, $R^{22}$, and $R^{23}$, which may be the same or different, represent a hydrogen atom, $C_{1-6}$alkyl, $C_{2-6}$ alkenyl, or $C_{1-6}$ alkyl substituted by an unsaturated five- to seven-membered carbocyclic group, or
$R^{21}$ and $R^{23}$ may together form
group —$(CH_2)_3$—,
group —$CHR^{24}CH_2CH_2$— wherein $R^{24}$ represents $C_{1-6}$ alkyl or amino optionally substituted by $C_{1-6}$ alkyl, $C_{1-6}$ alkoxycarbonyl, aralkyl, or aralkyloxycarbonyl,
group —$CH_2CHR^{24}CH_2$— wherein $R^{24}$ is as defined above,
group —$CH_2CH_2$—,
group —$CHR^{24}CH_2$— wherein $R^{24}$ is as defined above,
group —$CR^{25}$=$CR^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, or when $R^{21}$ and $R^{23}$ may together form
group =CH—CH=CH—, then $R^{22}$ does not exist;
Q represents >C=O or >$CH_2$;
$R^6$ represents a hydrogen atom, $C_{1-6}$ alkyl, or $C_{1-6}$ alkyl substituted by an unsaturated five- to seven-membered carbocyclic group;
$R^7$ represents a hydrogen atom or $C_{2-6}$ alkynyl;
$R^8$ represents a hydrogen atom or amino, wherein amino is optionally substituted by $C_{1-6}$ alkyl, $C_{1-6}$ alkoxycarbonyl, benzenesulfonyl in which the phenyl portion is optionally substituted by $C_{1-6}$ alkyl; aralkyl, aralkyloxycarbonyl, or group —C(=O)—(CH$_2$)$_s$—C(=O)—NHR$^{11}$ wherein s is an integer of 0 to 4 and R$^{11}$ represents a hydrogen atom or hydroxyl;

m is an integer of 0 to 2;

n is an integer of 0 or 1; and q is 1.

19. A method according to claim 6, wherein the integrin α$_v$β$_3$-mediated disease is selected from the group consisting of acute myocardial infarction, neointima formation hypertrophy, restenosis after PTCA/stent operation, unstable angina, acute coronary syndrome, angina pectoris after PTCA/stent operation, or arterial sclerosis, diabetic retinopathy, diabetic vascular complication, or vascular grafting; cerebral infarction; solid tumors or metastasis thereof; arthritis, and osteoporosis, hypercalcema, periodontitis, hyperparathyroidism, periarticular sore, or Paget's diseases.

20. 3-[3-amino-2-chloro-4-{4-(1,4,5,6-tetrahydropyrimidin-2-yl)-piperazin-1-yl}-benzoylamino]-(2S)benzenesulfonylamino-propionic acid, or a pharmaceutically acceptable salt or solvate thereof.

21. A method for treating an integrin α$_v$β$_3$-mediated disease selected from the group consisting of cardiovascular diseases, angiogenesis-related diseases, cerebrovascular diseases, cancers and metastasis thereof, immunological diseases, and osteopathy, comprising the step of administering an effective amount of a compound of claim 20 or a pharmaceutically acceptable salt or solvate thereof together with a pharmaceutically acceptable carrier, to mammals including humans.

22. A method for treating platelet thrombosis or thromboembolism, the improvement of peripheral circulating blood stream, the inhibition of blood clotting during extracorporeal circulation, or the treatment of thrombotic thrombocytopenic purpura or hemolytic uremic syndrome, comprising the step of administering an effective amount of a compound of claim 20 or a pharmaceutically acceptable salt or solvate thereof together with a pharmaceutically acceptable carrier, to mammals including humans.

23. A method for inhibiting platelet aggregation, comprising the step of administering an effective amount of a compound of claim 20 or a pharmaceutically acceptable salt or solvate thereof together with a pharmaceutically acceptable carrier, to mammals including humans.

24. The method according to claim 19 wherein the α$_v$β$_3$ mediated disease is atherosclerosis or rheumatic arthritis.

* * * * *